(12) United States Patent
Tao et al.

(10) Patent No.: US 11,480,580 B2
(45) Date of Patent: Oct. 25, 2022

(54) METHODS AND REAGENTS TO LABEL BACTERIA AND VIRUS AND IDENTIFY THEIR INTERACTING PROTEINS

(71) Applicant: Purdue Research Foundation, West Lafayette, IN (US)

(72) Inventors: Weiguo Andy Tao, Lafayette, IN (US); Ying Zhang, Shanghai (CN); Mayank Srivastava, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 361 days.

(21) Appl. No.: 16/851,172

(22) Filed: Apr. 17, 2020

(65) Prior Publication Data

US 2020/0333354 A1 Oct. 22, 2020

Related U.S. Application Data

(60) Provisional application No. 62/836,387, filed on Apr. 19, 2019.

(51) Int. Cl.
*G01N 33/68* (2006.01)
*G01N 33/567* (2006.01)
*G01N 33/574* (2006.01)

(52) U.S. Cl.
CPC ....... *G01N 33/6848* (2013.01); *G01N 33/567* (2013.01); *G01N 33/57469* (2013.01);
(Continued)

(58) Field of Classification Search
CPC .......... G01N 33/6848; G01N 33/6845; G01N 33/567; G01N 33/57469; G01N 33/6842;
(Continued)

(56) References Cited

U.S. PATENT DOCUMENTS 10,947,319 B2 * 3/2021 Weisser ............ A61K 47/6869
2018/0112212 A1 * 4/2018 Nicol ................ G01N 33/6845

OTHER PUBLICATIONS

Garrett, W., "Cancer and the microbiota", Science 2015, 348, p. 18.
(Continued)

*Primary Examiner* — Kiet T Nguyen
(74) *Attorney, Agent, or Firm* — Purdue Research Foundation

(57) ABSTRACT

Disclosed herein is a chemo-proteomic probe for labelling and monitoring a live microbe interacting with a host cell and for qualitative and quantitative analyses of those proteins involved during a microbe infects the host cell. This probe comprises a functional group for conjugating to a surface protein of a live microbe under a physiological condition; a photo-reactive group for covalent cross-linking to an interacting cell protein of a host; and a tag for isolating the cross-linked complex of the surface protein of said live microbe and the interacting protein of a host cell for qualitative and quantitative proteomics analyses. The probe may further comprise a visualization tag. This technology takes advantage of the high throughput feature of mass spectrometry analysis and combines it with a uniquely designed chemistry to achieve high efficient isolation and analysis of host cell proteins interacting with a pathogen at different stages of an infection.

20 Claims, 29 Drawing Sheets

Specification includes a Sequence Listing.

(52) U.S. Cl.
CPC ..... *G01N 33/6842* (2013.01); *G01N 2458/00* (2013.01); *G01N 2500/04* (2013.01); *G01N 2560/00* (2013.01)

(58) Field of Classification Search
CPC ........... G01N 2458/00; G01N 2500/04; G01N 2560/00; C07D 495/04
USPC ......................................................... 435/7.1
See application file for complete search history.

(56) References Cited

OTHER PUBLICATIONS

Beltran, P., et al., "Proteomics and integrative omic approaches for understanding host-pathogen interactions and infectious diseases", Mol. Syst. Biol. 2017, 13, 922, pp. 19.

Weekes, M., et al., "Quantitative Temporal Viromics: An Approach to Investigate Host-Pathogen Interaction", Cell 2014, 157, pp. 1460-1472.

Scaturro, P., et al., "An orthogonal proteomic survey uncovers novel Zika virus host factors", Nature 2018, 561, pp. 253-257.

Sobotzki, N., et al., "HATRIC-based identification of receptors for orphan ligands", Nat. Commun. 2018, 9, 1519, pp. 8.

Bar-Peled. L., et al., "Chemical Proteomics Identifies Druggable Vulnerabilities in a Genetically Defined Cancer", Cell 2017, 171, pp. 696-709.

He, D, et al., "Quantitative and Comparative Profiling of Protease Substrates through a Genetically Encoded Multifunctional Photocrosslinker", Angew. Chem. Int. Ed., 2017, 56, pp. 14521-14525.

Broncel, M., et al., "Multifunctional Reagents for Quantitative Proteome-Wide Analysis of Protein Modification in Human Cells and Dynamic Profiling of Protein Lipidation During Vertebrate Development", Angew. Chem. Int. Ed. 2015, 54, pp. 5948-5951.

Wang, L., et al., "Time-Resolved Proteomic Visualization of Dendrimer Cellular Entry and Trafficking", J. Am. Chem. Soc. 2015, 137, pp. 12772-12775.

Schroeder, N.,et al., "The Lipid Raft-Associated Protein CD98 is Required for Vaccinia Virus Endocytosis" J. Virol. 2012, 86, pp. 4868-4882.

\* cited by examiner

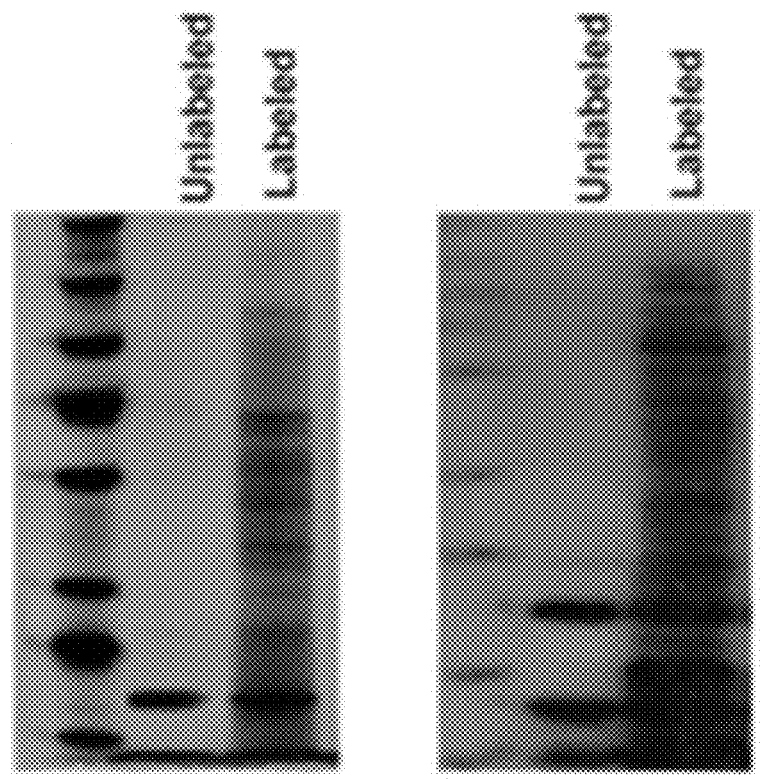
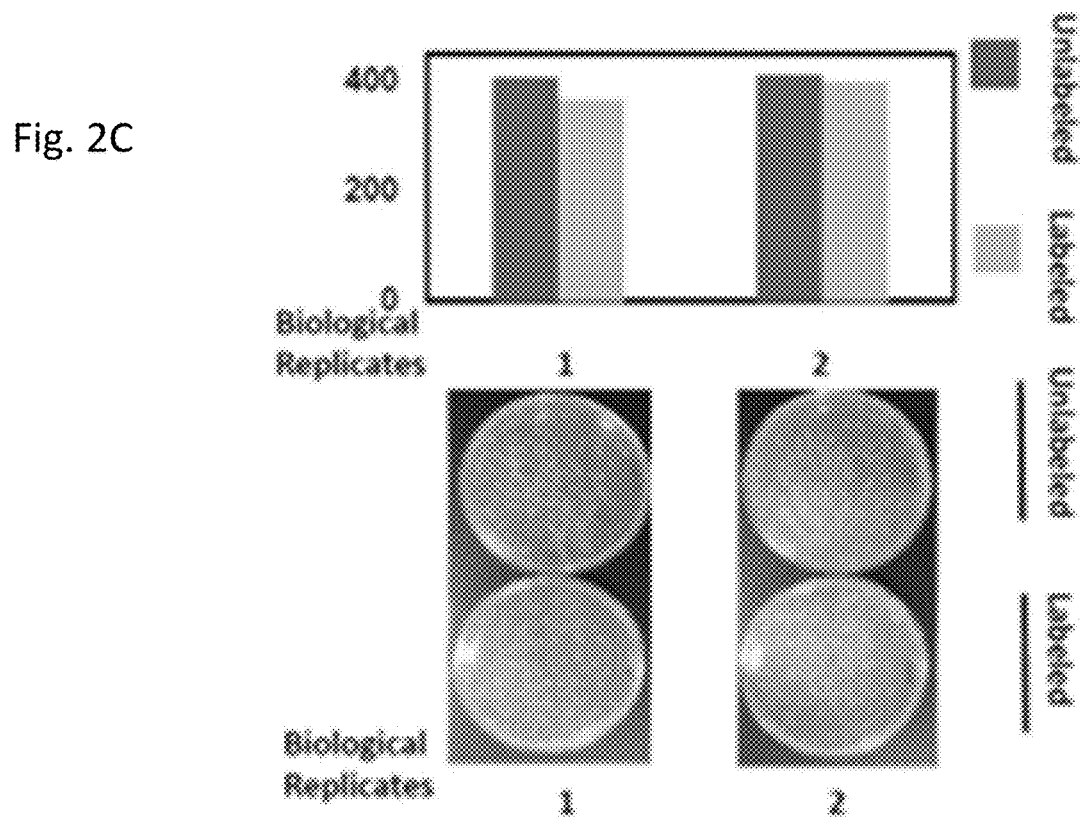
Fig. 2A      Fig. 2B
Fig. 2C

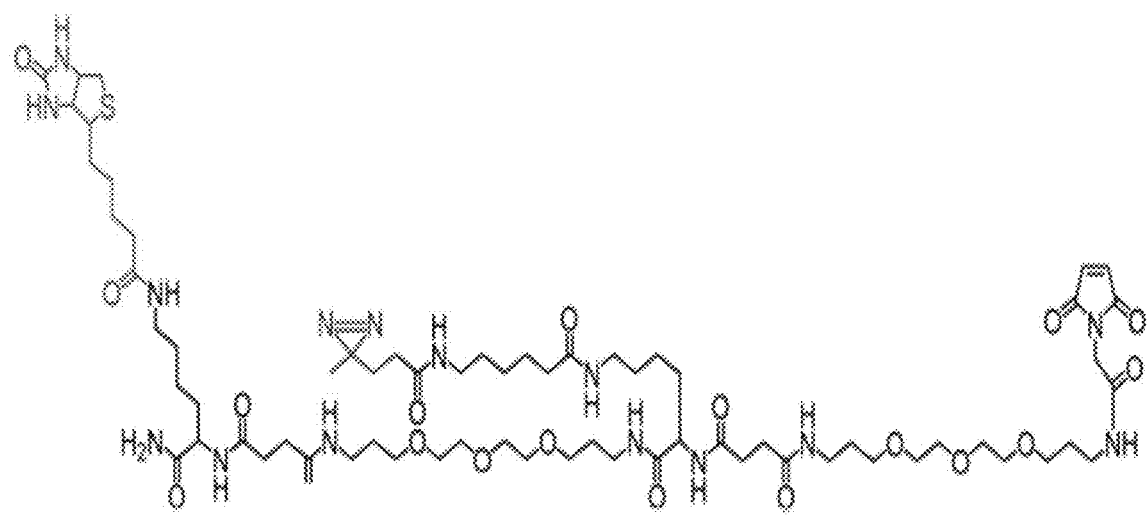
Fig. 6A
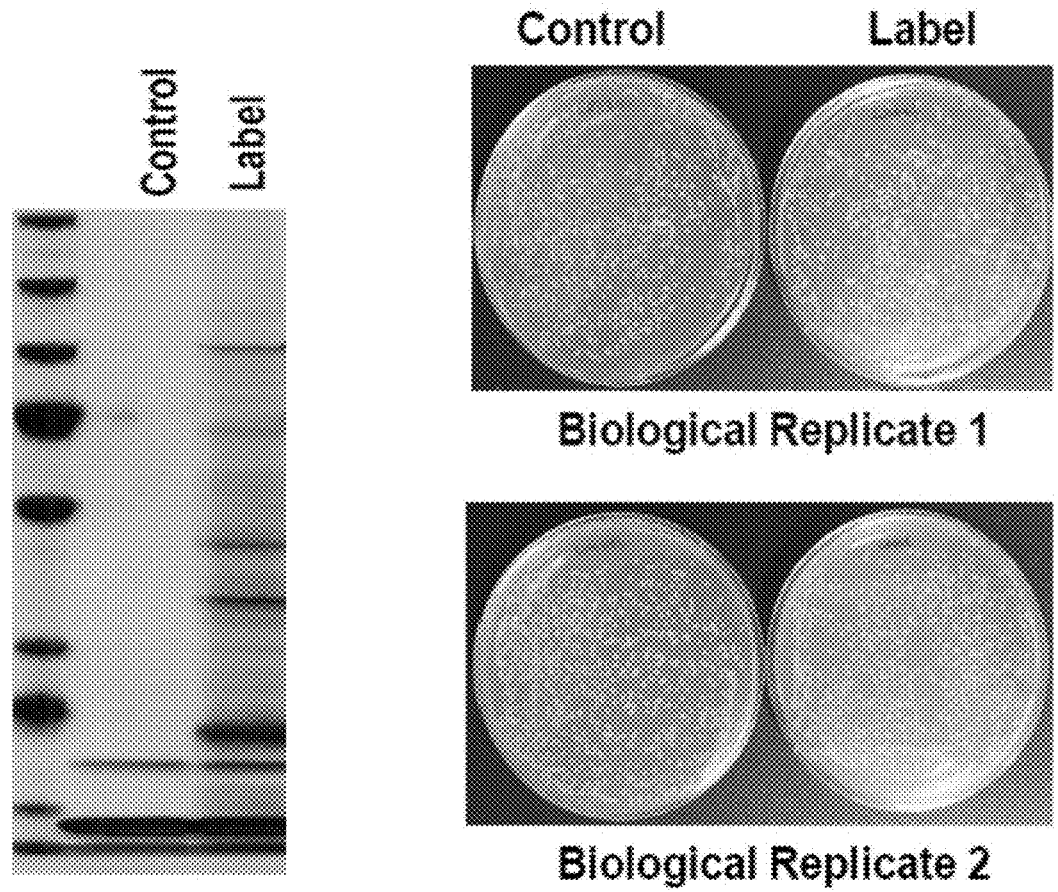
Fig. 6B
Fig. 6C

METHODS AND REAGENTS TO LABEL BACTERIA AND VIRUS AND IDENTIFY THEIR INTERACTING PROTEINS

CROSS-REFERENCE TO RELATED APPLICATIONS

This present U.S. patent application under 35 U.S.C. § 111(a) relates to and claims the benefits of the U.S. Provisional Application No. 62/836,387, filed on Apr. 19, 2019, the content of which is incorporated herein by reference in its entirety.

STATEMENT OF GOVERNMENT SUPPORT

This invention was made with government support under GM088317, GM111788, and RR025044 awarded by the National Institutes of Health (NIH), and under 1506752 awarded by the National Science Foundation. The government has certain rights in the invention.

STATEMENT OF SEQUENCE LISTING

A computer-readable form (CRF) of the Sequence Listing is submitted with this application. The file, entitled 68397-02_ST25_txt, is generated on Apr. 7, 2020. Applicant states that the content of the computer-readable form is the same and the information recorded in a computer readable form is identical to the written sequence listing.

TECHNICAL FIELD

The present disclosure generally relates to a probe for enabling a mass spectrometry based analysis, and in particular to a chemical probe developed to label a virus or a bacterium and then crosslink their interacting proteins with that of a host cell during the infection process in real time.

BACKGROUND

This section introduces aspects that may help facilitate a better understanding of the disclosure. Accordingly, these statements are to be read in this light and are not to be understood as admissions about what is or is not prior art.

The studying of interaction between hosts and pathogens, and the gaining of the proteome changes in host cells after pathogen infection is critical for understanding the biology of pathogen infection and discovering novel targets that can protect hots against pathogens. In recent years, the study of infectious diseases has benefited significantly from the contribution of proteomic approaches which can provide a global view of host-pathogen interactions and can profile the changes of the host cell proteome on a systemic level. Although proteomics has been successfully employed to study infectious diseases, there are still several questions remain challenging to be addressed. Upon pathogen entry into a host cell, host-pathogen interactions occur regularly throughout the whole pathogen replication cycle, however, most of the existing strategies for mapping of the host-pathogen interaction only focus on certain infection time point thereby fall short in providing a temporal interactions profile that covers the infection life cycle. Especially, interactions that are very transient and weak in nature are difficult to be discovered by traditional approaches. Recently, the development of chemo-proteomic reagent and approach allowed the identification of receptors for ligands, which also implies its application in finding of new putative pathogen-host interactions as receptors for recognizing the pathogen on the host cell surface. However, this approach still could not provide a temporal interaction profile because the capture of receptor through chemical reaction only occurs on the cell surface, when the pathogen goes inside the host cell, interaction information between the host and pathogen could not be revealed by this method.

Therefore, there is a need to develop a system to observe the host pathogen interactions at different stages of infection.

BRIEF DESCRIPTION OF THE FIGURES

FIG. 6A shows structure illustration of MAL probe. FIG. 6B shows SDS-PAGE of salmonella lysate captured by NeutrAvidin beads. Before lysate, salmonella was labeled with NHS-functionalized probe. Unlabeled salmonella was also lysed and captured as control. FIG. 6C shows comparison of the replication activity of salmonella before and after labeling with MAL-functionalized probe.

(FIG. 8A) Structure of virus labeling reagent. Maleimide reacts with available cysteines on the virus surface under mild conditions, diazirine enables crosslinking host proteins at fixed time points allowing tracking virus movement in 'real-time', and biotin acts as a handle for protein enrichment and identification by downstream mass spectrometric analysis. The three functionalities are separated by a membrane-impermeable polyethylene glycol (PEG)-like linkers, while offering the flexibility required for capturing interacting proteins with the aqueous solubility; (FIG. 8B) Labeling of ZIKV surface proteins. Purified Zika virions were diluted and reacted with the labeling reagent in PBS at 4° C. Reaction was quenched with three-fold excess cysteine for 1 hour. (FIG. 8C) Workflow for capturing virus receptors and tracking its cellular entry. Labeled ZIKV was diluted in DMEM and incubated with confluent cells for 1 hour at 4° C. Additionally, cells were incubated with the labeled viruses in 37° C. for fixed time points to allow virus entry. Unbound viruses were removed and cells were directly exposed to UV light. Cells were lysed and biotinylated proteins were captured on the avidin beads. Proteins were digested on beads using sequential Lys-C and trypsin digestion, and analyzed by LC-MS/MS. Label-free quantitation was performed using MaxQuant to identify the crosslinked proteins.

(FIG. 10A) Immunofluorescence demonstrating the membrane binding of anti-NCAM antibody to Vero cells; (FIG. 10B) Anti-NCAM inhibits Zika infection of Vero cells. After antibody inhibition of NCAM, about 50% reduction in internalized Zika RNAs was observed; (FIG. 10C) Membrane expression of NCAM1 in HEK293T cells. Expression plasmid with NCAM1 was transfected into HEK293T cells. After 48 hours post-transfection, immunofluorescence was performed to confirm surface expression of NCAM1; (FIG. 10D) qRT-PCR revealed an increase in viral attachment following NCAM overexpression.

(FIG. 11A) Venn diagram showing the number of proteins crosslinked at each time point, and implicated in viral process according to DAVID Biological Process enrichment; (FIG. 11B) Principal component analysis (PCA) showing the reproducibility among replicates; (FIG. 11C) Gene Ontology cellular component analysis of crosslinked proteins using DAVID, highlighting membrane and cytosolic proteins, along with p values. The crosslinked proteins were analyzed by DAVID analysis; (FIG. 11D) Heat map demonstrating log protein intensities at 0, 4, and 8 minutes of infection normalized to the control. Potential contaminants, proteins identified by only site, and in decoy database were removed, and t-test was further used to identify the proteins with significant changes (permutation based FDR 1%). Proteins with a ratio of 2.5 and above (log 2>1.32), compared to control, were only considered for analysis. Representative graphs highlighting the protein changes at different times of infection for selected proteins.

FIG. 14A shows standard protein Bovine Serum Albumin (BSA) was labeled with the chemical probe in phosphate buffer pH 7 overnight. The reaction was quenched with excess cysteine, and the labeled proteins were enriched on streptavidin beads. The chemical probe labeling efficiency was quantified by comparing the protein band intensity for labeled BSA with the amount started with. A no-chemical probe control was employed to account for non-specific binders. In parallel, the BSA was pre-reduced and alkylated prior to labeling, to confirm cysteine as the labeling site on the protein by the maleimide-diazirine-biotin reagent. FIG. 14B shows purified zika virus was labeled by the chemical probe using the same protocol as above. Silver stain (4G2, anti-E) demonstrating successful labeling of E proteins (SEQ ID NO: 1) of Zika. FIG. 14C shows purified zika virus was labeled by the chemical probe using the same protocol as above. Western blot (4G2, anti-E) demonstrating successful labeling of E proteins (SEQ ID NO: 1) of Zika. FIG. 14D shows the infectivity of labeled virus was confirmed by plaque assay. The number of plaque forming units (pfu) after virus labeling with 1 mM chemical probe were similar to the unlabeled virus.

FIG. 15D shows the overlay of all time points. The difference in interactions among time points were highlighted in circles.

FIG. 17A demonstrates that Vero cells were incubated with anti-mouse FITC to account for the non-specific binding. The overlay image with DAPI showed minimal background signal. FIG. 17B demonstrates that non-transfected HEK293T cells were fixed and treated with anti-NCAM and anti-mouse Alexa Fluor 488, followed by DAPI staining. No significant signal for NCAM was observed in the overlay.

BRIEF DESCRIPTION OF SEQUENCE LISTING

Figure 1A:
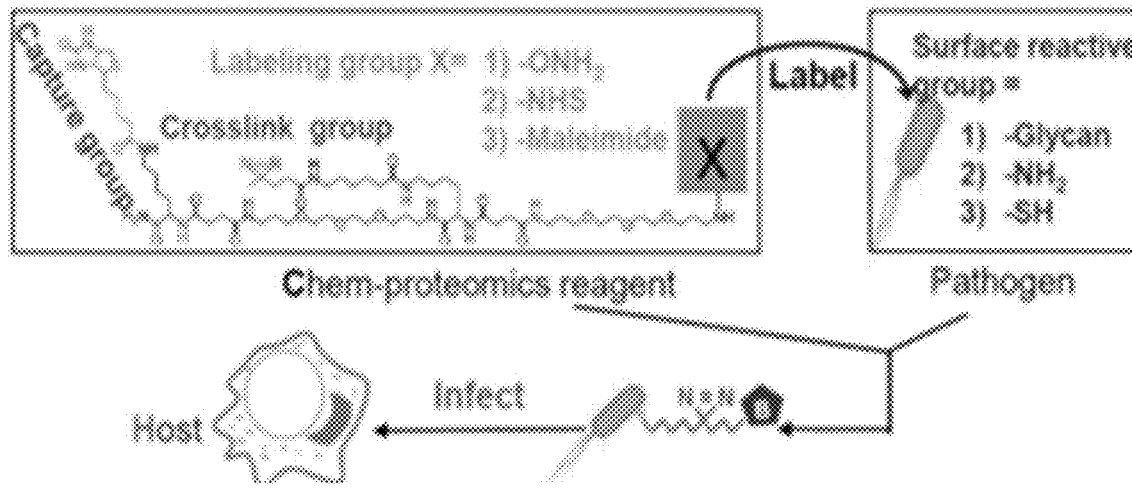
FIG. 1A shows the structure of trifunctional probe.

SEQ ID NO:1, Peptide E protein of Zika identified by mass spectrometric analysis:

IRCIGVSNRDFVEGMSGGTWVDVVLEHGGCVTVMAQDKPTVDIELVTTTV

SNMAEVRSYCYEASISDMASDSRCPTQGEAYLDKQSDTQYVCKRTLVDRG

WGNGCGLFGKGSLVTCAKFTCSKKMTGKSIQPENLEYRIMLSVHGSQHSG

MIGYETDEDRAKVEVTPNSPRAEATLGGFGSLGLDCEPRTGLDFSDLYYL

TMNNKHWLVHKEWFHDIPLPWHAGADTGTPHWNNKEALVEFKDAHAKRQT

VVVLGSQEGAVHTALAGALEAEMDGAKGRLFSGHLKCRLKMDKLRLKGVS

YSLCTAAFTFTKVPAETLHGTVTVEVQYAGTDGPCKIPVQMAVDMQTLTP

VGRLITANPVITESTENSKMMLELDPPFGDSYIVIGVGDKKITHHWHRSG

STIGKAFEATVRGAKRMAVLGDTAWDFGSVGGVFNSLGKGIHQIFGAAFK

SLFGGMSWFSQILIGTLLVWLGLNTKNGSISLTCLALGGVMIFLSTAVSA

DETAILED DESCRIPTION

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected.

As used herein, the following terms and phrases shall have the meanings set forth below. Unless defined otherwise, all technical and scientific terms used herein have the same meaning as commonly understood to one of ordinary skill in the art.

In the present disclosure the term "about" can allow for a degree of variability in a value or range, for example, within 10%, within 5%, or within 1% of a stated value or of a stated limit of a range. In the present disclosure, the term "substantially" can allow for a degree of variability in a value or range, for example, within 90%, within 95%, 99%, 99.5%, 99.9%, 99.99%, or at least about 99.999% or more of a stated value or of a stated limit of a range.

The term "substituted" as used herein refers to a functional group in which one or more hydrogen atoms contained therein are replaced by one or more non-hydrogen atoms. The term "functional group" or "substituent" as used herein refers to a group that can be or is substituted onto a molecule. Examples of substituents or functional groups include, but are not limited to, a halogen (e.g., F, Cl, Br, and I); an oxygen atom in groups such as hydroxyl groups, alkoxy groups, aryloxy groups, aralkyloxy groups, oxo (carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, azides, hydroxylamines, cyano, nitro groups, N-oxides, hydrazides, and enamines; and other heteroatoms in various other groups.

Disclosed herein is a chemo-proteomic probe for labelling and monitoring a live microbe interacting with a host cell and for qualitative and quantitative analyses of those proteins involved during a microbe infects the host cell. This probe comprises a functional group for conjugating to a surface protein of a live microbe under a physiological condition; a photo-reactive group for covalent cross-linking to an interacting cell protein of a host; and a tag for isolating the cross-linked complex of the surface protein of said live microbe and the interacting protein of a host cell for qualitative and quantitative proteomics analyses. The probe may further comprise a visualization tag. This technology takes advantage of the high throughput feature of mass spectrometry analysis and combines it with a uniquely designed chemistry to achieve high efficient isolation and analysis of host cell proteins interacting with a pathogen at different stages of an infection.

In some illustrative embodiments, the present disclosure relates to a chemo-proteomic probe comprising:
 a) a functional group for conjugating to a surface protein of a live microbe under a physiological condition;
 b) a photo-reactive group for covalent cross-linking to an interacting protein of a host cell; and
 c) a tag for isolating the cross-linked complex of the surface protein of said live microbe and the interacting protein of a host cell for qualitative and quantitative analyses.

In some illustrative embodiments, the present disclosure relates to a chemo-proteomic probe as disclosed herein, the chemo-proteomic probe further comprising a visualization tag for viewing the interactions between the microbe and a host cell in real time.

In some illustrative embodiments, the present disclosure relates to a chemo-proteomic probe as disclosed herein, wherein the live microbe is a pathogen to human or an animal comprising a bacterium or a virus.

In some illustrative embodiments, the present disclosure relates to a chemo-proteomic probe as disclosed herein, wherein the live microbe is a bacterium or a virus.

In some illustrative embodiments, the present disclosure relates to a chemo-proteomic probe as disclosed herein, wherein the probe is suitable for studying the temporal interactions between a pathogen and its host cell.

In some illustrative embodiments, the present disclosure relates to a chemo-proteomic probe as disclosed herein, wherein the photo-reactive group is a photocrosslinker or a photocleavable caging group.

In some illustrative embodiments, the present disclosure relates to a chemo-proteomic probe as disclosed herein, wherein the photocrosslinker is a diazirine or an aryl azide.

In some illustrative embodiments, the present disclosure relates to a chemo-proteomic probe as disclosed herein, wherein the probe has a formula:

a) providing a chemo-proteomic probe comprising: a functional group for conjugating to a surface protein of a live microbe under a physiological condition; a photo-reactive group for covalent cross-linking to an interacting protein of a host cell; and a tag for isolating the cross-linked complex of the surface protein of said (I)

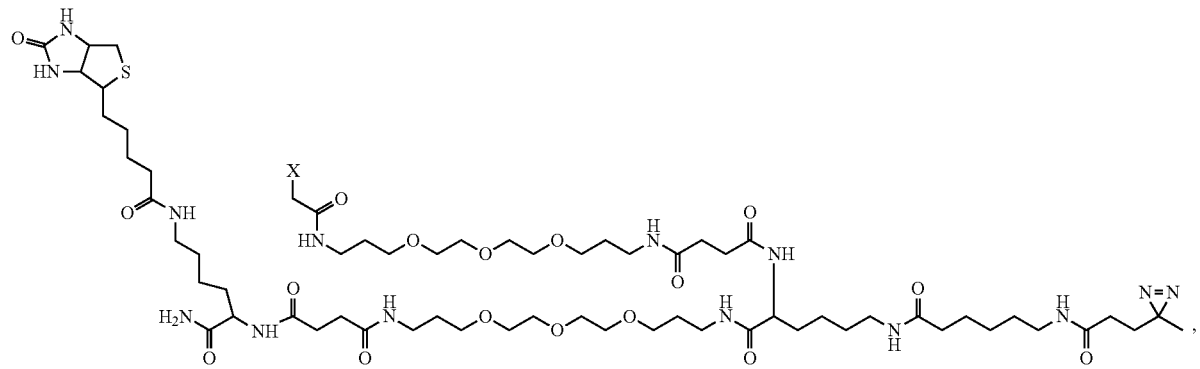

or an acceptable salt thereof, wherein X is said functional group selected from the group consisting of N-hydroxysuccinimide (NHS), maleimide (MAL), or aminooxy (ONH$_2$).

In some illustrative embodiments, the present disclosure relates to a chemo-proteomic probe as disclosed herein, wherein the probe has a formula (I) and wherein said X is

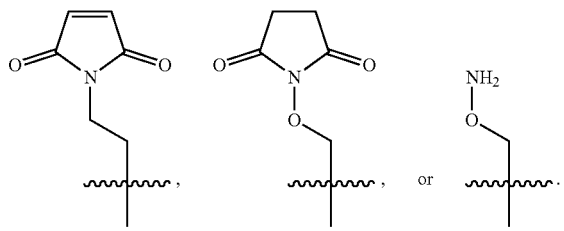

In some illustrative embodiments, the present disclosure relates to a chemo-proteomic probe as disclosed herein, wherein the tag for isolating the cross-linked complex of the surface protein of said live microbe and the interacting protein of a host cell for qualitative and quantitative analyses is selected from the group consisting of biotin, thiobiotin, azide-alkyne, aldehyde-hydrazine, aldehyde-hydroxylamine, thiol-iodoacetyl, and a thiobiotin-based affinity tag.

In some illustrative embodiments, the present disclosure relates to a chemo-proteomic probe as disclosed herein, wherein the live microbe is a bacterium or a virus and the docking surface reactive group of a host cell for covalent conjugation is a reactive group of glycan.

In some illustrative embodiments, the present disclosure relates to a chemo-proteomic probe as disclosed herein, wherein the live microbe is a bacterium or a virus and the docking surface reactive group of a host cell for covalent conjugation is a functional group selected from the group consisting of amino (NH$_2$) and thiol (SH).

In some other illustrative embodiments, the present disclosure relates to a method of identifying proteins interactions between a host and a pathogen microbe in real time, comprising the steps of:

live microbe and the interacting protein of a host cell for qualitative and quantitative analyses;

b) allowing the microbe to infect the host;

c) crosslinking at fixed time points so that the interacting proteins of the host cells have sufficiently interacted with the surface proteins of the pathogen microbe;

d) isolating the cross-linked complex of the surface proteins of said pathogen microbe and the interacting cell proteins of a host utilizing the tag; and e) performing qualitative and quantitative analyses of the isolated cross-linked protein complex.

In some other illustrative embodiments, the present disclosure relates to a method of identifying proteins interactions between a host and a pathogen microbe in real time as disclosed herein, wherein the pathogen microbe is a virus or a bacterium.

In some other illustrative embodiments, the present disclosure relates to a method of identifying proteins interactions between a host and a pathogen microbe in real time as disclosed herein, wherein the qualitative and quantitative analysis is to sequence the isolated cross-linked protein complex by mass spectroscopy.

In some other illustrative embodiments, the present disclosure relates to a method of identifying proteins interactions between a host and a pathogen microbe in real time as disclosed herein, wherein the chemo-proteomic probe further comprising a visualization tag to view the microbe-host cell interaction in real time.

In some other illustrative embodiments, the present disclosure relates to a method of identifying proteins interactions between a host and a pathogen microbe in real time as disclosed herein, wherein the photo-reactive group is a diazirine or an aryl azide.

In some other illustrative embodiments, the present disclosure relates to a method of identifying proteins interactions between a host and a pathogen microbe in real time as disclosed herein, wherein the chemo-proteomic probe has a formula:

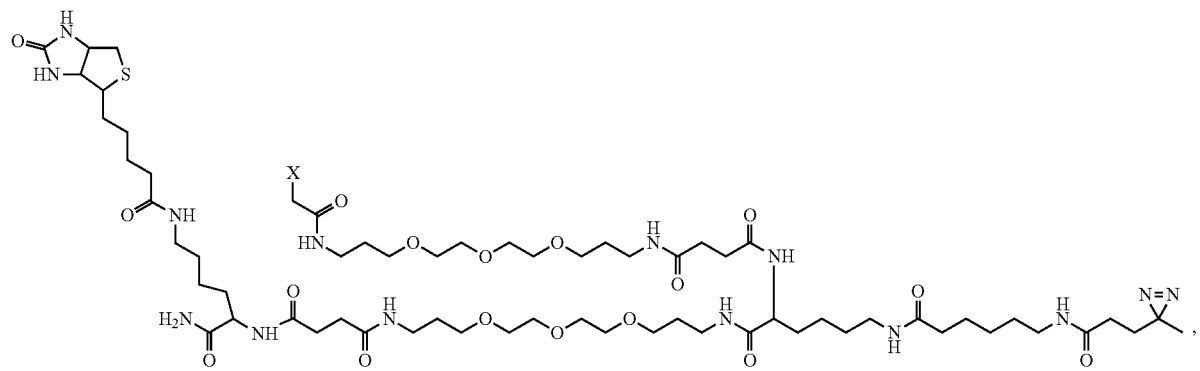

or an acceptable salt thereof, wherein X is said functional group selected from the group consisting of N-hydroxysuccinimide (NHS), maleimide (MAL), or aminooxy (ONH$_2$).

In some other illustrative embodiments, the present disclosure relates to a method of identifying proteins interactions between a host and a pathogen microbe in real time as disclosed herein, wherein the probe has a formula (I) and wherein said X is

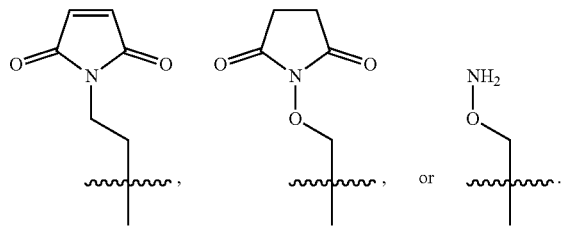

In some other illustrative embodiments, the present disclosure relates to a method of identifying proteins interactions between a host and a pathogen microbe in real time as disclosed herein, wherein the tag for isolating the cross-linked complex of the surface protein of said live microbe and the interacting cell protein of a host for qualitative and quantitative analyses is selected from the group consisting of biotin, thiobiotin, azide-alkyne, aldehyde-hydrazine/hydroxylamine, thiol-iodoacetyl, and a thiobiotin-based affinity tag.

In some other illustrative embodiments, the present disclosure relates to a kit for identifying interactions between a host cell and a pathogen microbe in real time, comprising:
a) a chemo-proteomic probe comprising: a functional group for conjugating to a surface protein of a live microbe under a physiological condition; a photo-reactive group for covalent cross-linking to an interacting cell protein of a host; and a tag for isolating the cross-linked complex of the surface protein of said live microbe and the interacting cell protein of a host for qualitative and quantitative proteomics analyses; and
b) reagents for enabling said conjugation and crosslinking.

The interaction between hosts and pathogens are complex and are still incompletely understood. Although in vivo pathogen-host cell protein interactions have been achieved through various approaches on certain time point during the infection, studying the temporal profile of interaction between pathogen and host and their dynamic regulation during infection is still challenge due to the lacking of method. Towards this goal, we developed an in-vivo cross-linking chemical proteomics strategy in this study and it is successfully demonstrated to provide a comprehensive approach for describing temporal interactions changes in pathogen and host during infection in a temporal manner. As this chemical proteomic approach is applicable to many bacteria or virus, we believe it would contribute to the discovery and understanding of host-pathogen interactions in other systems, and therefore can further help to acquire new insights into the communication between the two organisms as well as to get a better understanding of the infection process on a molecular level.

The use of photoactivatable probes offers a key advantage of light-controlled conversion of transient noncovalent interactions into covalent isolable complexes, thus enabling large-scale identification of ligand (e.g., drug, lipid or enzyme)-binding proteins by mass spectrometry. In previous study, through functionalized dendrimer with a UV cross-linking group together with a fluorescent group and an isolation group, we achieved tracing of the endocytosis of nanoparticle into cells. Therefore, we assume that taking advantage of the photo-crosslinking can be carried out in live mammalian cells where protein-protein interactions take place, and labeling the pathogen with such a tailor-made chemo-proteomics probe would be used to study the entry of pathogen into host cells.

Uncovering specific interactions between host cells and pathogens and measuring the proteome changes in host cells after pathogen infection is critical for understanding the biology of pathogen infection.[1] The study of infectious diseases has greatly benefited from the contribution of proteomic approaches which can provide a global view of host-pathogen interactions.[2] However, there are still questions to be addressed. Most of the existing strategies for mapping of the host-pathogen interaction or the changes in proteome of host only focus on certain infection time points,[3-5] and thereby fall short in providing a temporal interaction profile that can cover a more complete infection cycle. Moreover, a lot of these interactions may be weak and transient, and thus are difficult to capture by traditional approaches.

Recently, several chemical proteomic approaches were introduced to identify receptors for ligands.[6,7] These studies also imply their application in finding new putative pathogen-host interactions. As these approaches mainly aimed at capturing receptor through chemical reactions occurring on the host cell surface, they are not suitable for revealing the interactome after the pathogen enters the host cells. On the other hand, the use of photoactivatable probes offers a key advantage of light-controlled conversion of transient noncovalent interactions into covalent isolable complexes, thus enabling large-scale identification of ligands (e.g., drug, lipid)-binding proteins or substrates of enzyme within the cells by mass spectrometry (MS).[8-11]

Here, we report the development of a novel chemical proteomics strategy, termed host and pathogen temporal interaction profiling (HAPTIP), to globally map the host-pathogen interactome and demonstrate its application to the Salmonella infection process. Salmonella are Gram-negative bacterial pathogens that can infect a wide range of animals including humans, farm animals, and even plants.[12] Upon infection, Salmonella replicates within host cells in a membrane bound compartment, called the Salmonella-containing vacuole (SCV).[13] Intravacuolar bacterial replication depends on tightly controlled interactions with host cell vesicular compartments. Therefore, it is crucial albeit technically challenging to characterize the interactions involved in the Salmonella infection process. The core of the HAPTIP method is a new multifunctional chemical proteomics probe bearing a labeling group that conjugates the probe to Salmonella surface, a photo-reactive diazirine group which allows for covalent crosslinking of Salmonella proteins to their interacting host cell proteins thereby facilitating the discovery of transient or weak interactions, and an isolation group for purifying the interacting proteins for quantitative proteomics analysis. We apply the HAPTIP to study the interactome of host-pathogen in a time-resolved manner throughout the course of SCV formation. To the best of our knowledge, this is the first attempt to chemically label living bacteria for proteome profiling of host cell response.

Figure 5A:
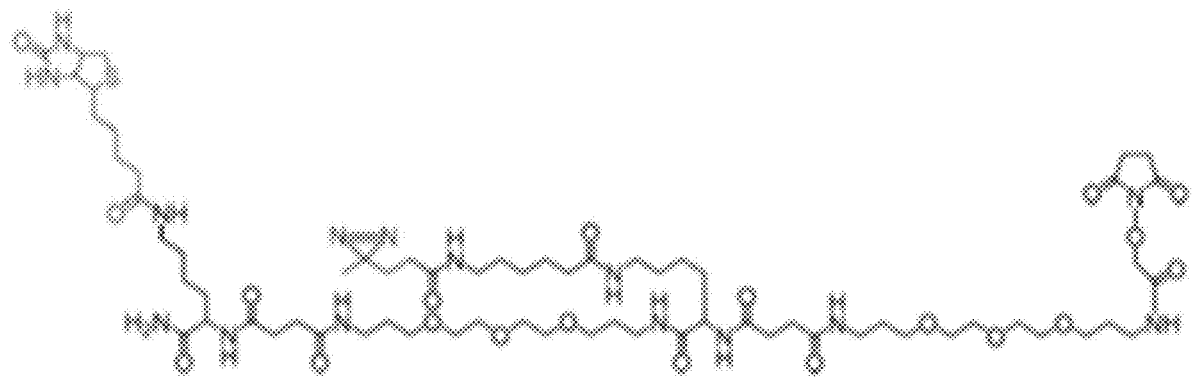
FIG. 5A shows structure illustration of NHS probe.
Figure 7A:
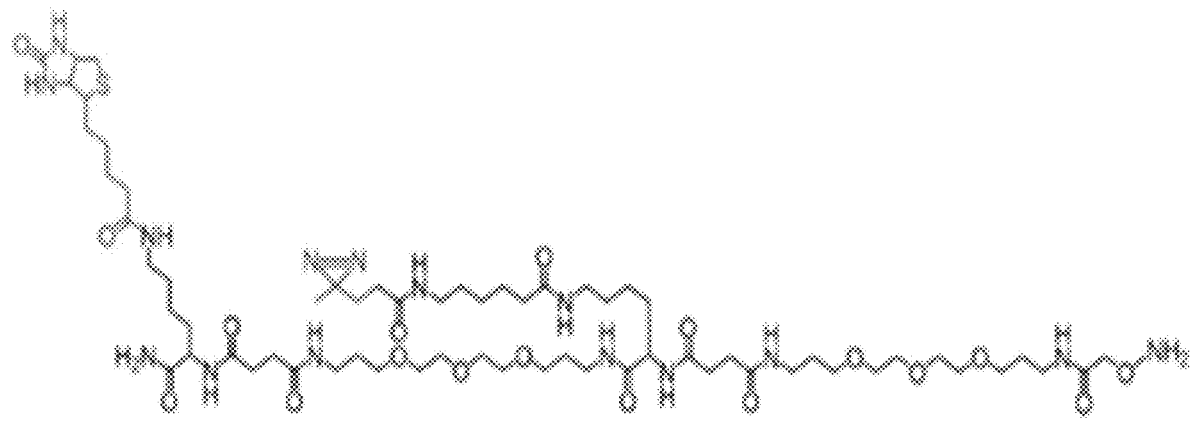
FIG. 7A shows structure illustration of $ONH_2$ probe.

Labeling living bacteria chemically requires careful considerations: The labeling reaction and resulting covalent attachment should have minimal impact on the function and activity of bacteria; and the labeling should have good efficiency for the follow-up identification of low abundance, specific interacting proteins in the host cells. Accordingly, we prepared three probes with different types of labeling group (FIG. 1A): 1) N-hydroxysuccinimide (NHS) group that reacts with the amine group on the cell surface proteins (FIGS. 5A-5C), 2) Maleimide (MAL) group that reacts with the thiol group on the cell surface proteins (FIGS. 6A-6C) and 3) Aminooxy ($ONH_2$) group that conjugates the reagent to the glycans on bacteria surface through oxime click reaction (FIG. 7A). The three probes were chosen based on the availability of corresponding surface reactive groups (amine, thiol and glycan groups) on pathogen and mild reaction conditions. Labeling on primary amine groups is expected to be most efficient, leading to potentially significant impact on bacteria activities.[14] On the other hand, sulfhydryls thiols are present in most proteins but are not as abundant as primary amines, and we expected labeling through thiols would have a minimum effect on Salmonella activity. For the $ONH_2$-probe, the oxime click reaction was chosen because it conjugates the aldehyde group generated after mildly oxidizing glycans on the Salmonella surface under physiological condition.[15,16] As the oxidation condition we utilized only oxidizes the terminal sialic acid on the cell surface and the probe was designed with a cell permeant polyethylene glycol chain, the labeling is expected to attach the probe on the outmost surface, thus facilitating capturing interacting proteins with minimum steric hindrance. Moreover, because lipopolysaccharide (LPS) present on the outer membrane of Gram negative bacteria can recognize and bind cell surface receptors during infection, we assume that labeling the glycan chain would help to identify LPS-interacting proteins as well.

Figure 2D:
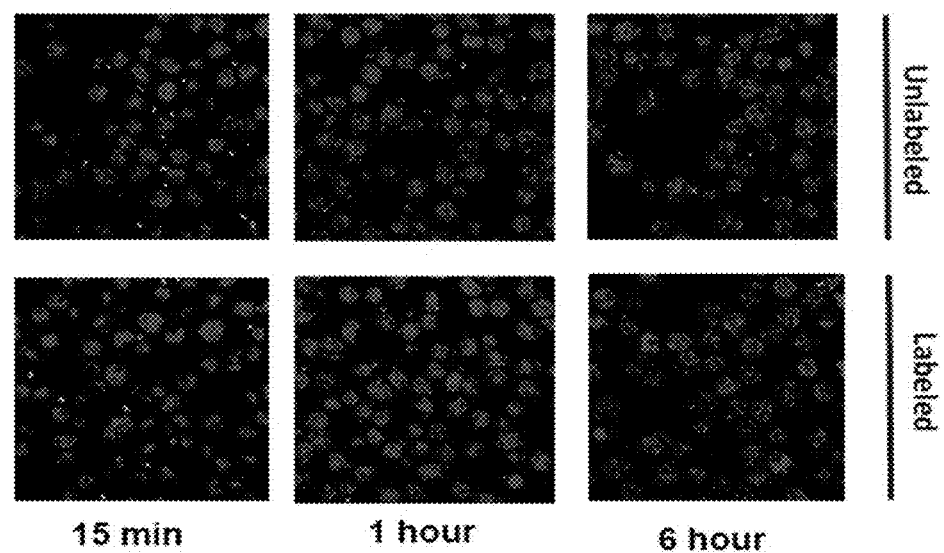
FIG. 2D shows comparison of infection ability of salmonella with and without $ONH_2$-probe labeling: labeled salmonella also showed very similar infection behavior as unlabeled bacterial.
Figure 2E:
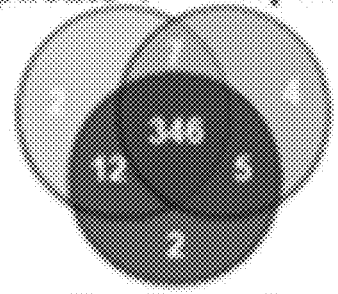
FIG. 2E demonstrates that GO analysis showed that more than 60% of the identified proteins (a total number of 376 proteins from 3 replicates are membrane proteins (FIG. 2F).
Figure 2F:
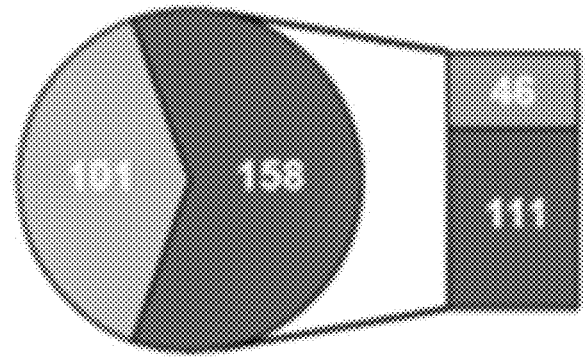
FIG. 2A shows the $ONH_2$ probe showed good labeling efficiency as revealed by SDS-PAGE and FIG. 2B shows Western blot detected by anti-biotin antibody.
FIG. 2C shows the labeling did not affect or only have little influence on the replication activity of salmonella.
Figure 2F:
Figure 5B:
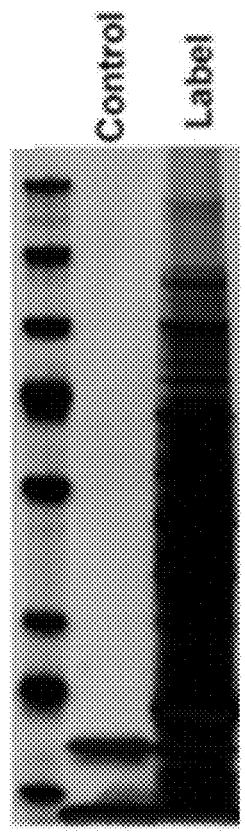
FIG. 5B shows SDS-PAGE of salmonella lysate captured by NeutrAvidin beads. Before lysate, salmonella was labeled with NHS-functionalized probe. Unlabeled salmonella was also lysed and captured as control.
Figure 5C:
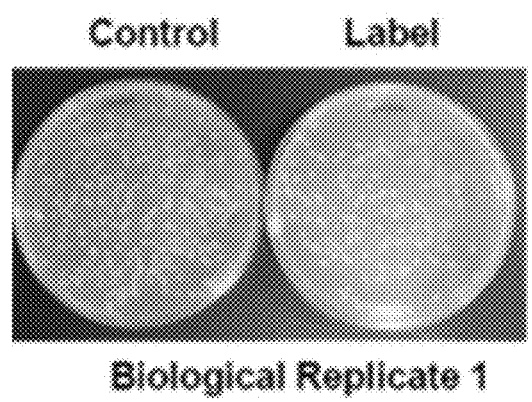
FIG. 5C shows comparison of the replication activity of salmonella before and after labeling with NHS-functionalized probe.
Figure 5C:
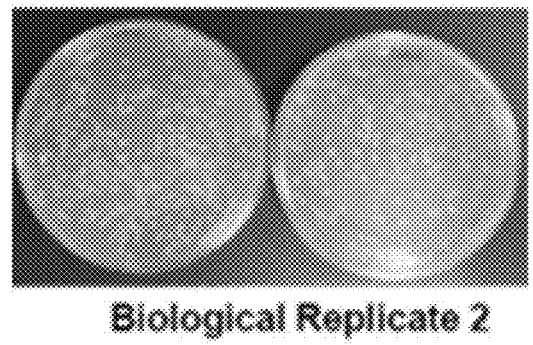
Figures 7B, 7C:
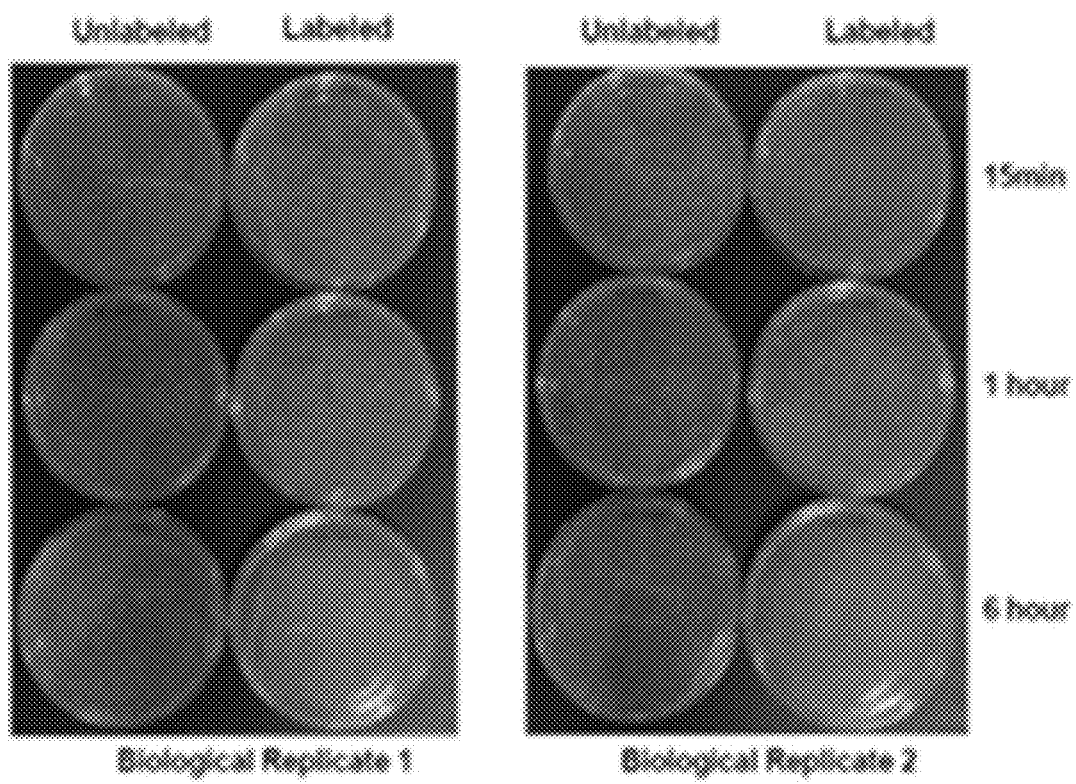
FIG. 7B shows comparison of the replication activity of salmonella before and after labeling with $ONH_2$-functionalized probe.
FIG. 7C is a repeat of FIG. 7B.

Salmonella was labeled with three distinctive probes and we examined the labeling efficiency and its effects on Salmonella growth, infection efficiency and intracellular survival. Results showed that the NHS-probe labeling affected bacterial growth (FIG. 5C) although the labeling efficiency was high (FIG. 5B). The labeling efficiency of Mal-probe was relatively low due to limited number of free thiol groups on the cell surface (FIG. 6B) and the bacterial growth was not affected (FIG. 6C). The $ONH_2$-probe showed good labeling efficiency as revealed by SDS-PAGE (FIG. 2A) and western blot detected by anti-biotin antibody (FIG. 2B). Importantly, the labeling had little influence on Salmonella growth (FIG. 2C) ect host cells with or without $ONH_2$-functionalized probe labeling. Encouragingly, the infection rate and intracellular survival in RAW264.7 macrophage cells with $ONH_2$-probe labeled Salmonella proved to be almost identical to the unlabeled Salmonella (see FIG. 2D and FIGS. 7B-7C). We further carried out mass spectrometric analysis on $ONH_2$-labeled bacteria proteins enriched by NeutrAvidin beads. Bacteria without labeling but captured by the NeutrAvidin beads was also analyzed by MS as the control. After subtracting the control hits, a total of 378 proteins were identified from three replicates (FIG. 2E). Among them, subcellular location of 259 proteins were known or predicted. Gene ontology cellular component (GOCC) analysis showed that more than 60% of these proteins were membrane proteins (FIG. 2F). Cell invasion proteins including SipB, SipD, and secreted effector protein SifA, SopD, SopE2, SseC, and SseJ, which are known to be important in Salmonella infection were identified, indicating that the labeling was primarily on the surface of Salmonella. Therefore, we finally chose the $ONH_2$-functionalized probe for all following studies. The synthesis and characterization of the multifunctional probe are outlined in Scheme 1 below.

Figure 1B:
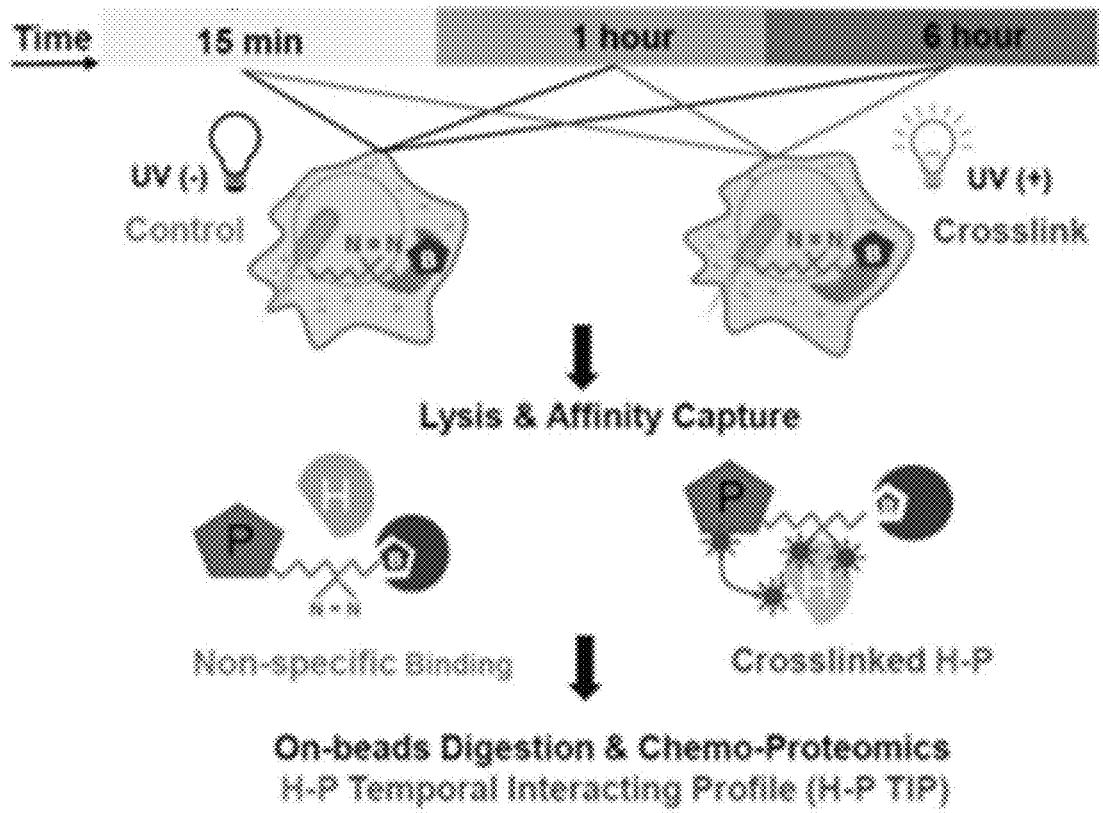
FIG. 1B shows experimental workflow for studying the entry of salmonella using chemical proteomics.

As illustrated in FIGS. 1A-1B, to temporally profile the interaction between Salmonella and host cells, labeled Salmonella were incubated with macrophage cells at the multiplicity of infection (MOI) of 50 for set intervals ranging from 15 min to 6 hours. Three time points were chosen based on the critical formation of SCV.[13] After washing away the externally attached Salmonella, macrophage samples with different infection times were irradiated with 365 nm UV light for 10 min to covalently crosslink proteins within close proximity to Salmonella. We reasoned that the probe with a photoreactive diazirine group, which is known to be specific in crosslinking molecules in close proximity, only react with proteins that are in direct contact with Salmonella, thereby minimizing crosslinking of other non-specific interacting proteins.[17] The irradiated cells were then harvested and lysed with lysis buffer, and NeutrAvidin beads were used to isolate the putative targets. The beads were subsequently washed with vigorous washing. Control isolation (without UV radiation) was also performed in the same biological context tested. The proteins enriched by NeutrAvidin beads either from samples and controls were digested on-beads sequentially with Lys-C and trypsin, and the resulting peptides were characterized and quantified by label-free LC-MS/MS.

Figure 3A:
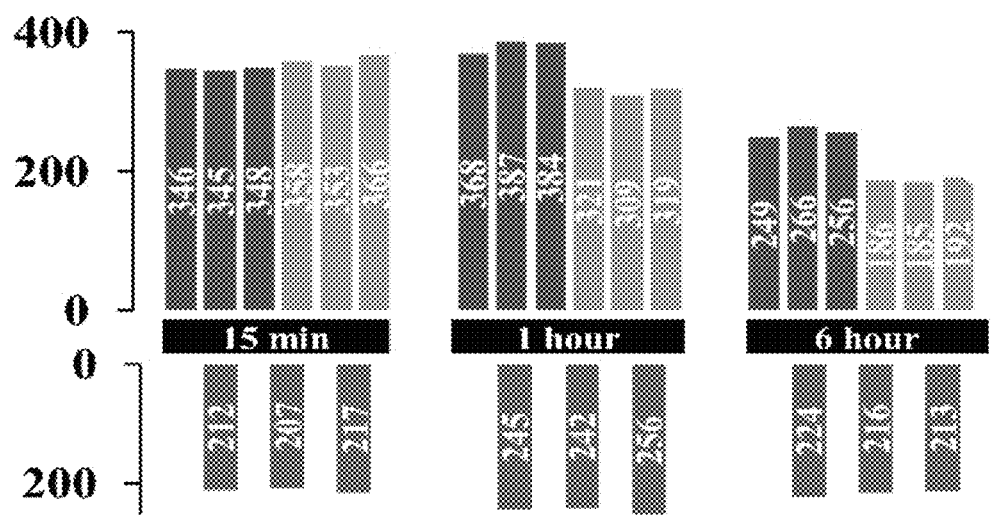
FIGS. 3A-3F. Proteins identified from samples and controls in each time point is shown in FIG. 3A. Among them, 292 (66%), 232 (52%), and 136 (31%) proteins were exclusively captured at 15 min, 1 hour, and 6 hours, respectively (FIG. 3B). Two independent biological replicates and three technique replicates correlated well for each time point, 15 min, 1 hour and 6 hour (FIG. 3C). The correlation analysis also revealed that the 15 min and 1 hour results are more closely related, as both of these two time points are within the relatively early endocytosis process. Gene ontology cellular component (GOCC) analysis shows the proteins with the highest levels of enrichment originated from extracellular regions (including vesicles, organelles, and exosomes) or from membrane-bound vesicles or organelles, especially at 0.5 and 1 h (FIG. 3D). The function analysis indicates many of proteins identified in these three time points are related to biological processes implicated in endocytosis, salmonella infection, regulation of actin cytoskeleton as well as focal adhesion (FIG. 3E), and pathway analysis shows that these proteins are involved in a number of biological processes linked to Vacuolar transport, Cell-cell signaling, and Vesicle mediated transport (FIG. 3F).
Figure 3B:
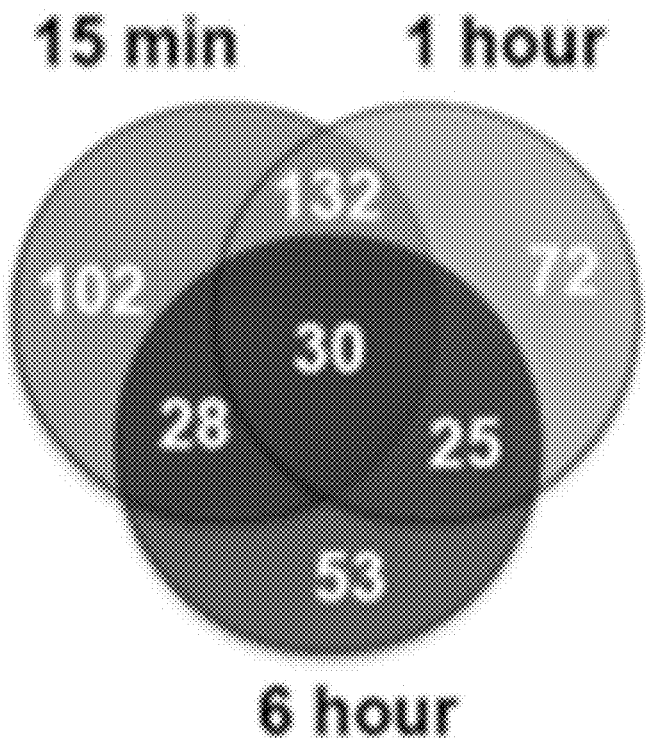
Figure 3C:
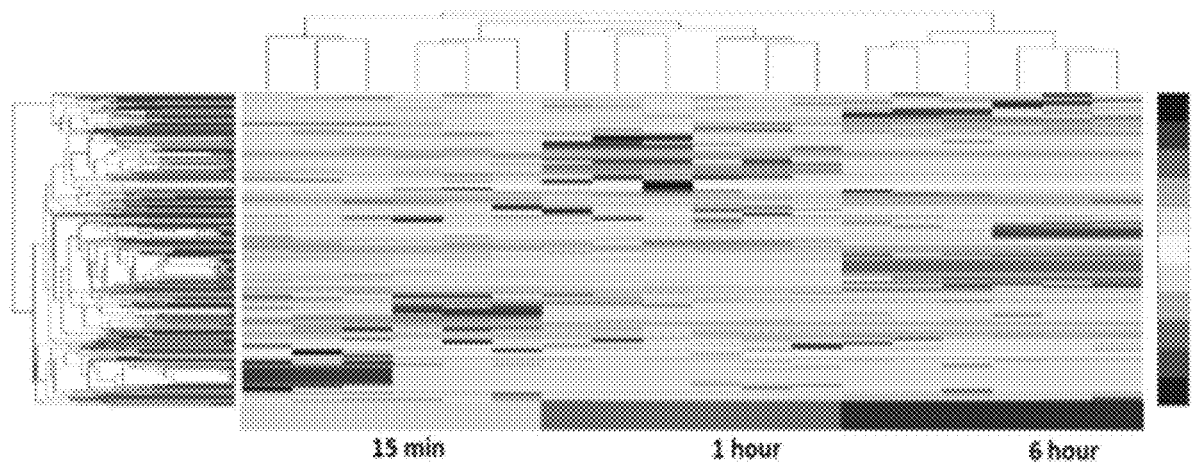
Figure 3D:
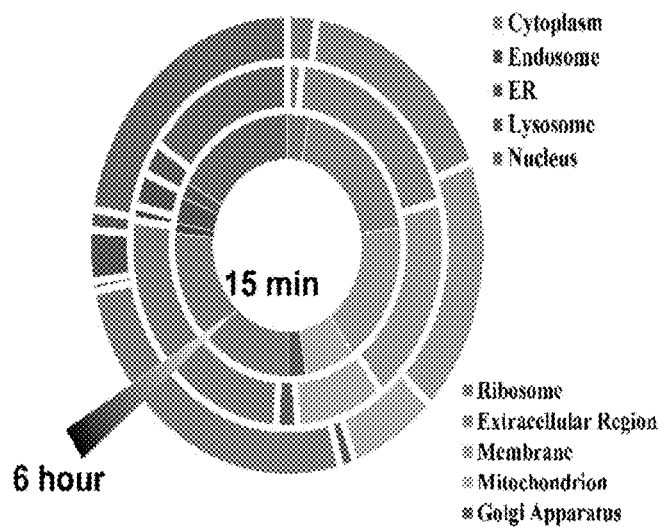
Figure 3E:
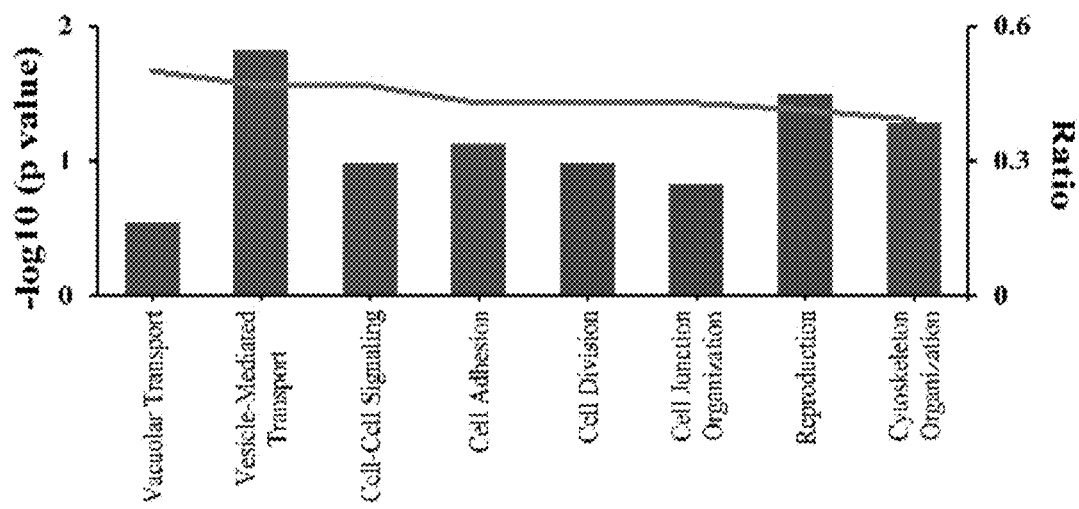
Figure 3F:
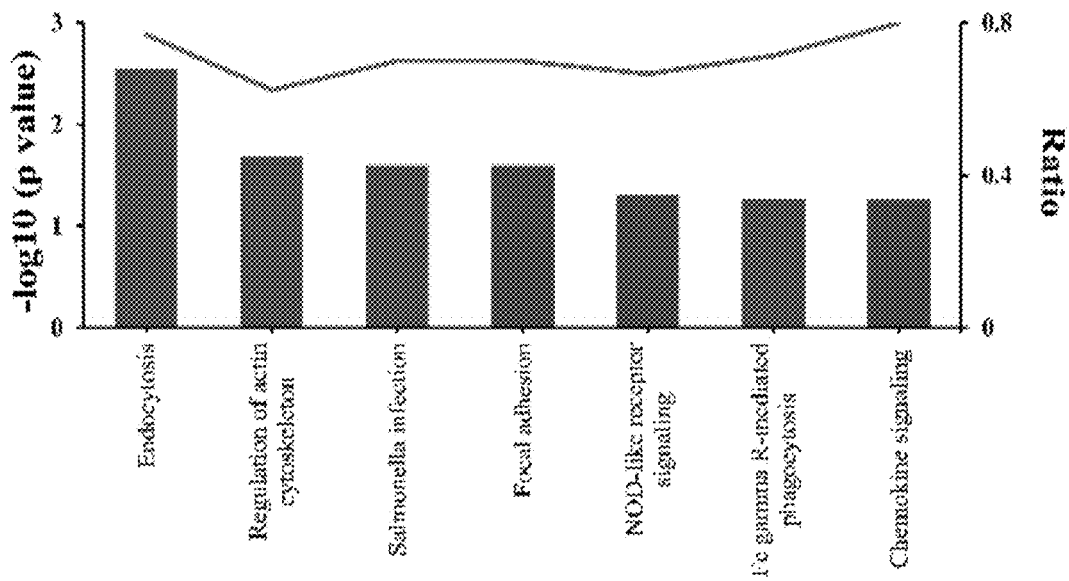

In total, we identified 442 crosslinked proteins in two biological replicates over the three time points during Salmonella internalization into macrophage cells. Proteins identified from samples and controls in each time point is shown in FIG. 3A. Among them, 292 (66%), 232 (52%), and 136 (31%) proteins were exclusively captured at 15 min, 1 hour, and 6 hours, respectively (FIG. 3B). High technical and biological reproducibility were achieved, as two independent biological replicates and three technical replicates correlated well in each time point (FIG. 3C). The correlation analysis also revealed that the 15 min and 1 hour results were more closely related, as both of these two time points are within the relatively early endocytosis process. The three time points clearly separated in the principal component analysis (PCA) plot, also with the 15 min and 1 hour sharing more similarity. We then analyzed the proteomics data to see whether these proteins can fall into distinct biological processes or pathways. GOCC analysis showed the proteins with the highest levels of enrichment originated from extracellular regions (including vesicles, organelles, and exosomes) or from membrane-bound vesicles or organelles, especially at 0.5 and 1 h (FIG. 3D). The GOCC results agree with the infection process, as adhesion to the host cell surface is important for many bacteria to initiate infection, and further fuse with the cellular membrane to form SCV. We identified more nuclear proteins in 6 hour samples than the other two time points. We assumed that the reason may be the SCV membrane gets damaged in the late endocytosis process and the pathogen may escape into the host cell cytosol and become associated with nuclear proteins. The functional analysis indicates many proteins identified in these three time points are related to biological processes implicated in endocytosis, Salmonella infection, regulation of actin cytoskeleton as well as focal adhesion (FIG. 3E) and pathway analysis shows that these proteins are involved in a number of biological processes linked to vacuolar transport, cell-cell signaling and vesicle mediated transport (FIG. 3F).

Among specific proteins identified in each time point (FIG. 4A), at the very early time point of 15 min infection, Salmonella was internalized by phagocytic cells using the actin polymerization pathway, and proteins involved in this process are expected to crosslink with Salmonella. Indeed, Arpc 2, Arpc 4 and F-actin capping proteins were identified, which agrees with the fact that actin polymerization is stimulated in the initial steps of the internalization.[18] Other known interactions were also identified, for example Cdc 42, which is known to be activated by Salmonella effector SopB/SigD;[19] and Cd14, which is reported as the receptor for Salmonella.[20] Early SCV markers, Rab 5 and Trfc are also present in the 15 min sample. In the 1 hour sample, several proteins identified are overlapped with the 15 min samples, including Rab5, Rab7, Trfc, Cd14, Cd147, Cd180 and et al., while Cdc42 disappeared. In the 6 h sample, early and intermediate SCV matures into late SCV by loss of early endosomal proteins and simultaneous acquisition of selective late endosomal and lysosomal proteins including LAMP1,[21] while proteins that participate in the early SCV formation all disappeared, including abovementioned Cd family proteins and early SCV markers Rab5. Overall, these identified proteins include not only known SCV markers but also known receptors and adaptors for Salmonella, like Cd14. Cd14 has been recognized as a co-receptor (along with the Toll-like receptor TLR4 and MD-2) for the recognition of lipopolysaccharide from Salmonella surface.[22] Here, we identified Cd14 in the early infection stage but not in the stage of intermediate and late SCV, proving the direct interaction between Salmonella and Cd14 during the infection. Meanwhile, proteins from Salmonella that are known to interact with the host cells and help the uptake of Salmonella including SifA, SipB, SipC, SopA, SopD, SopE, SopE2 were identified,[13,18] further indicating the capability of this method to identify interaction between pathogen and host. Together, these results demonstrate that the HAPTIP strategy enabled us to trace the entry of Salmonella into host cells and identify the specific interacting proteins at different SCV formation processes (FIG. 4B). Pathway analyses revealed the known interaction between the identified proteins from the host cell and our results further provided the new information on the network among host cell and pathogen proteins (FIG. 4C).

In addition to proteins those are previously reported to interact with Salmonella, we also discovered several proteins from macrophage that previously are not known to interact with Salmonella during early stages of infection, such as Cd98, Cd180, Cd147 and Cd11b. Some of these were reported as receptor or ligands for LPS in other bacteria but have not been reported in the Salmonella-macrophage system. For example, the lipid raft-associated protein Cd98 is required for vaccinia virus endocytosis,[23] while the immunoglobulin superfamily member Cd147 is a critical host receptor for the meningococcal pilus components PilE and PilV.[24] Among them, we chose an interacting protein, Cd11b, to further verify its interaction with Salmonella. Cd11b was previously reported to bind LPS and promote TLR4 signaling and importantly, may participate in LPS uptake into cells.[25] But its role has not been clearly described in the process of Salmonella entry. To verify the interaction between Cd11b and macrophages in vitro, we applied a biotin switch method using a commercially available crosslinking reagent. Salmonella was first labeled by (Sulfosuccinimidyl-2-[6-(biotinamido)-2-(p-azidobenzamido) hexanoamido] ethyl-1,3'-dithiopropionate) (Sulfo-SBED) and the whole bacteria extract then was incubated with the lysate of macrophage. The mixture was irradiated by the same UV as described before and the crosslinked proteins were purified by NeutrAvidin beads. The recovered proteins were treated with the gel-loading buffer that contains the reduction reagent dithiothreitol to reduce the disulfide bond on the crosslinking reagent, which resulted in the transfer of biotin group to Salmonella-interacting proteins in host cells to facilitate their pull-down by NeutrAvidin beads. The western blot result confirmed the crosslinked Cd11b after UV crosslinking, while a much weaker signal was observed without UV crosslinking (FIG. 4D). The interaction between Cd11b and Salmonella was further confirmed by a standard pull-down experiment. Together, the HAPTIP strategy allowed us to identify novel interaction between Salmonella and macrophages, which provided leads for future exploration on understanding the molecular mechanism of bacterial infection process.

The interaction between host cells and pathogens are highly dynamic and complex with many questions to be answered. It is extremely valuable to provide a dynamic picture of such interactions during the infection process. Towards this goal, we developed a novel time-resolved chemical proteomics strategy. It is conceivable that the general strategy of HAPTIP can be applicable to many bacteria or virus, thus contributing to the discovery and understanding of host-pathogen interactions in multiple infection systems.

Figure 13:
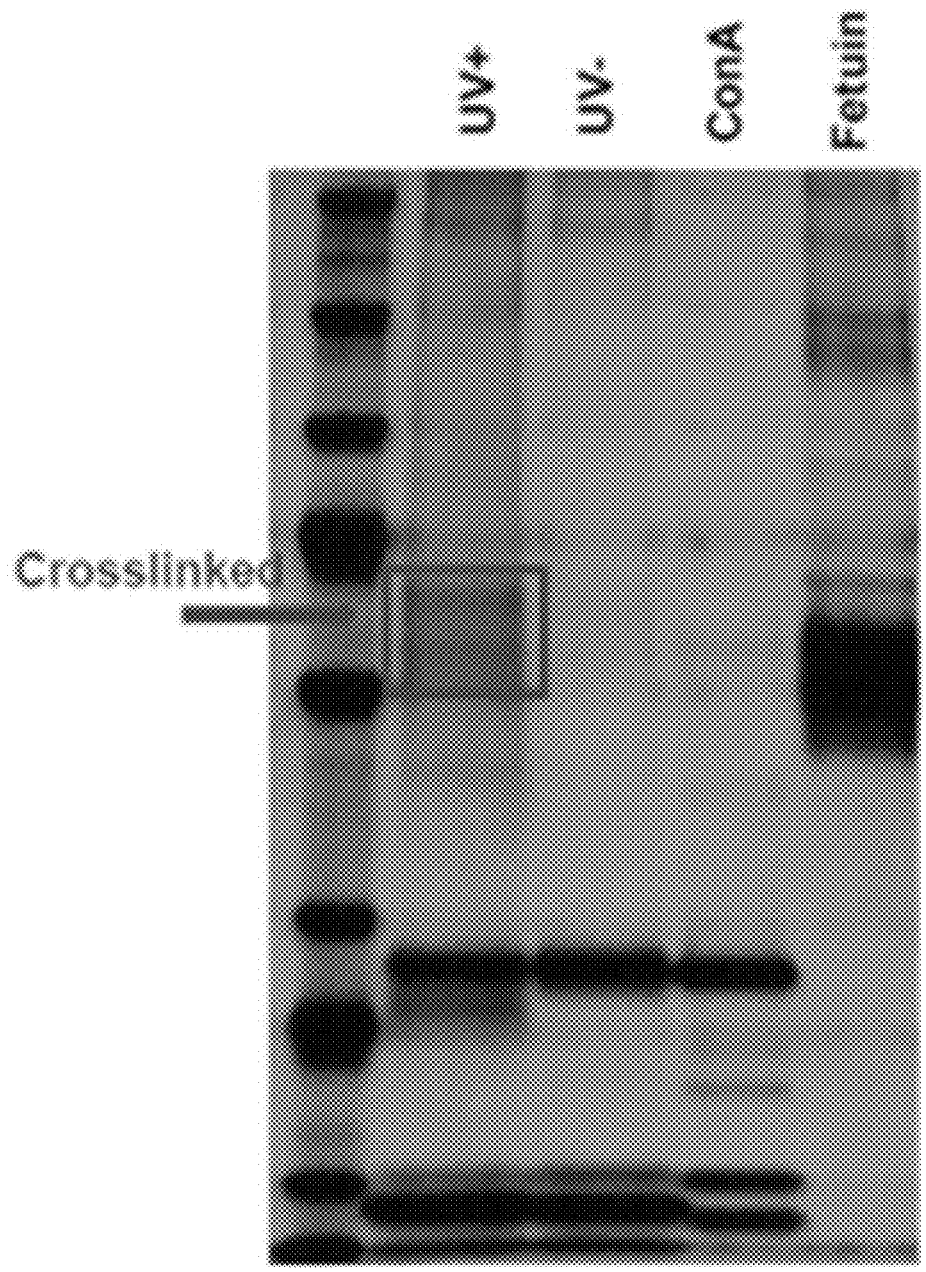
FIG. 13 shows the feasibility of crosslink using two proteins (Concanavalin A and Fetuin) with known interaction.
Figure 14A:
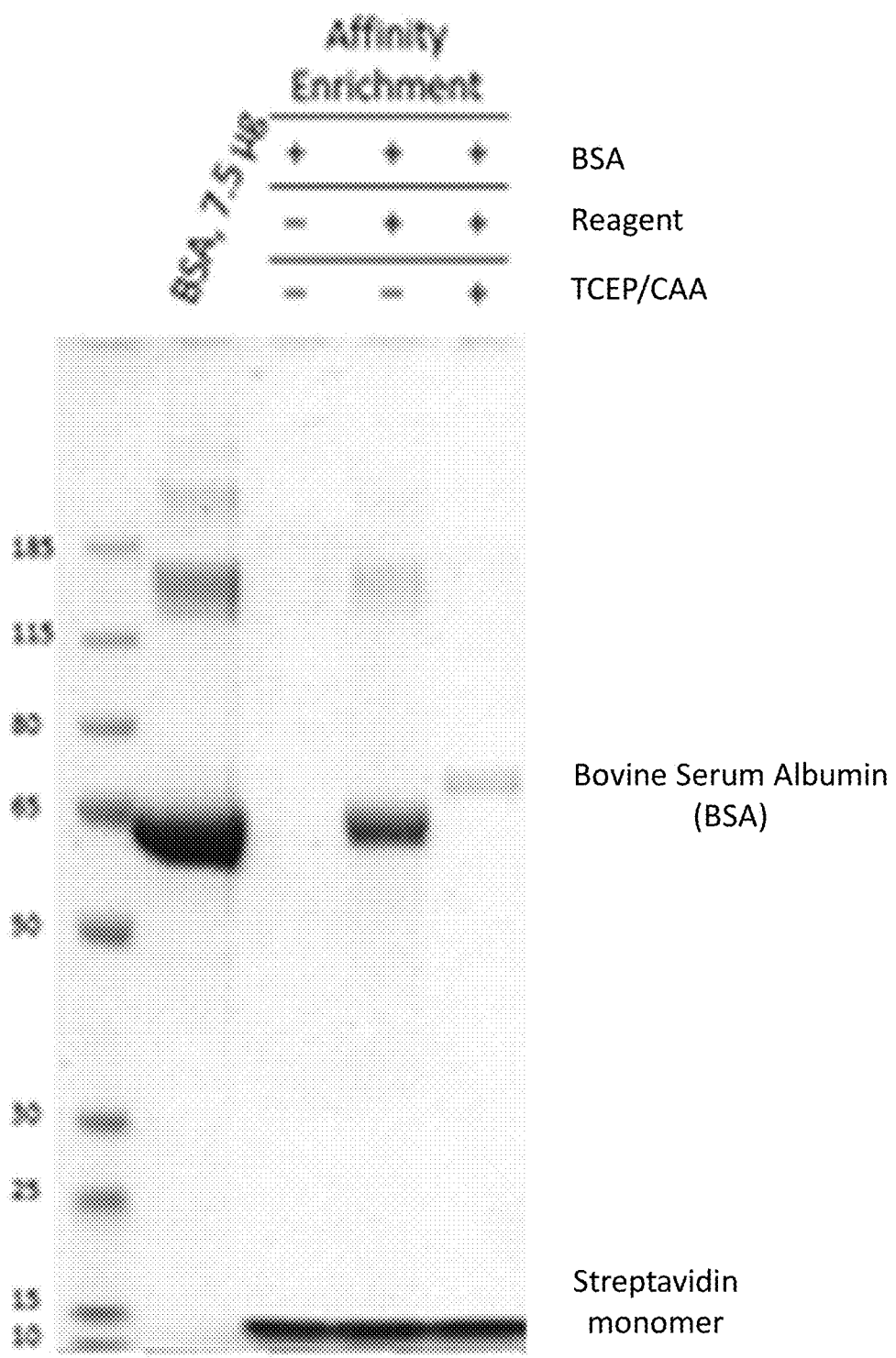
FIGS. 14A-14D show protein labeling by a chemical probe.
Figure 14B:
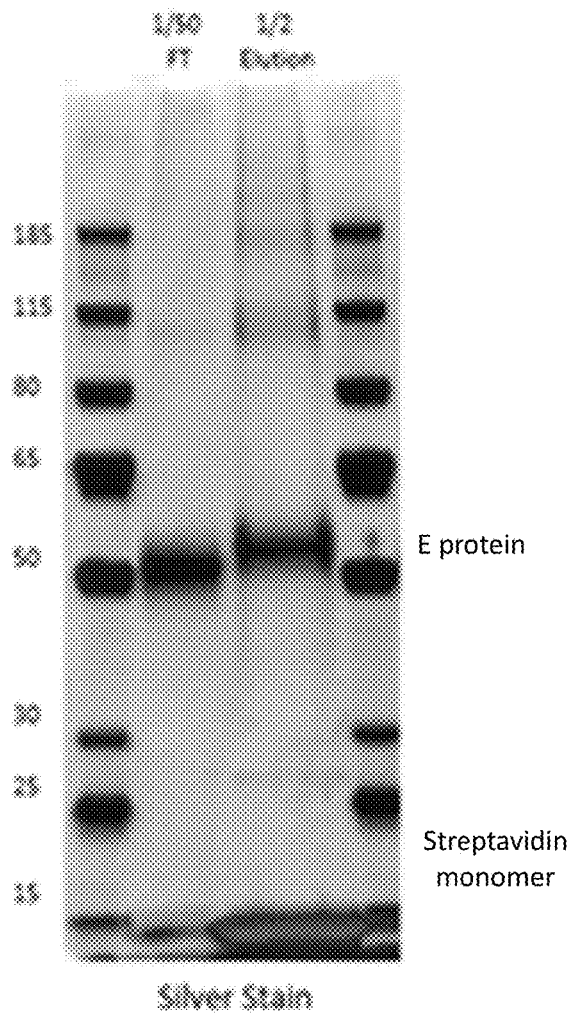
Figure 14C:
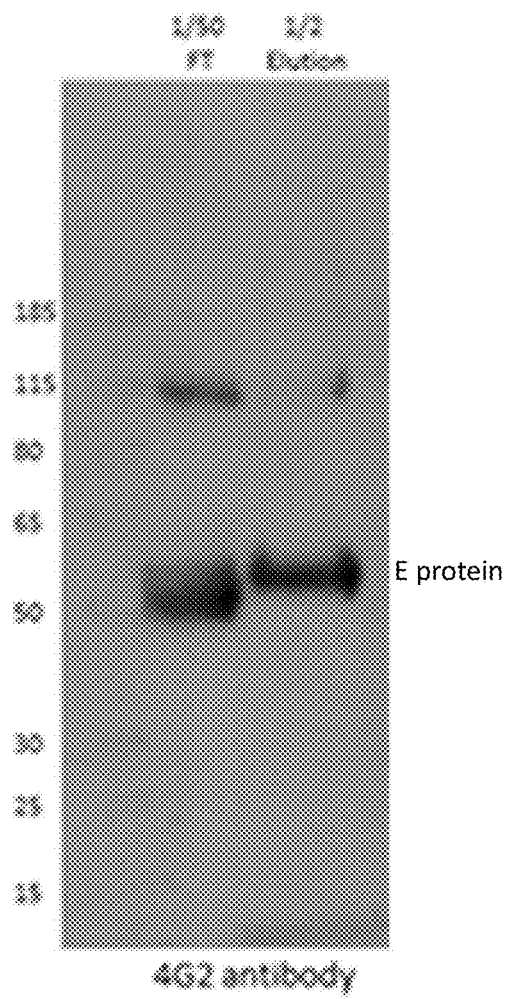
Figure 14D:
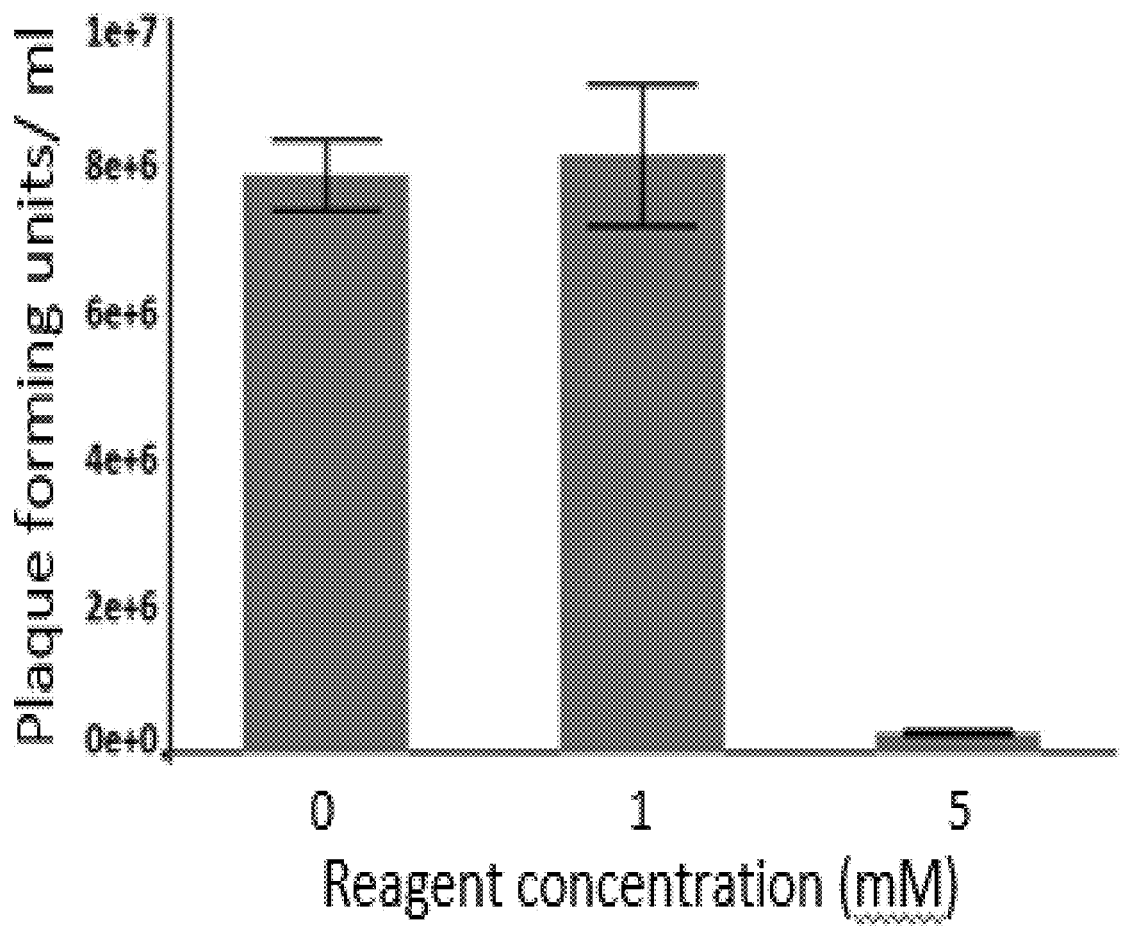
Figure 15A:
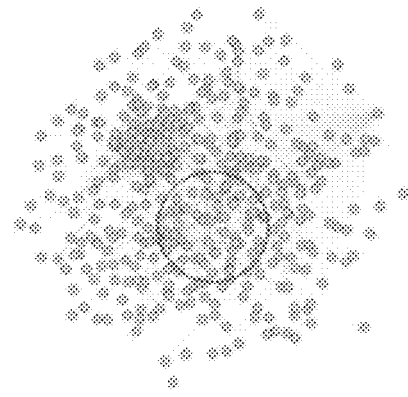
FIGS. 15A-15D show network analysis using STRING showing the protein-protein interactions at different time points of infection. Visualization was performed by Cytoscape. The interactions (or edges) were shown in different colors for the three time points: Yellow for 0 min (FIG. 15A), Blue for 4 min (FIG. 15B), and Red for 8 min (FIG. 15C) of Zika infection.
Figure 15B:
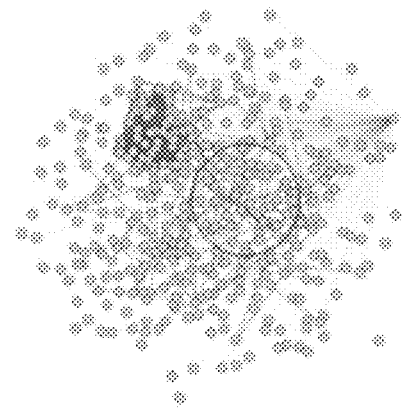
Figure 15C:
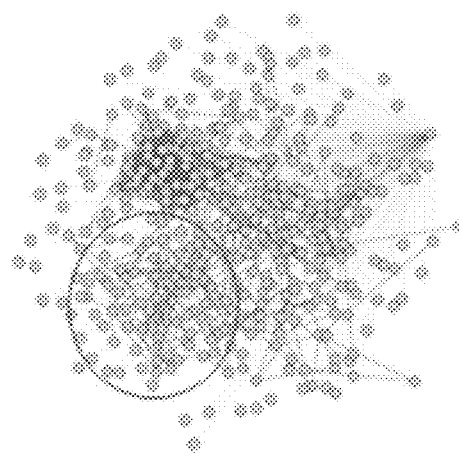
Figure 15D:
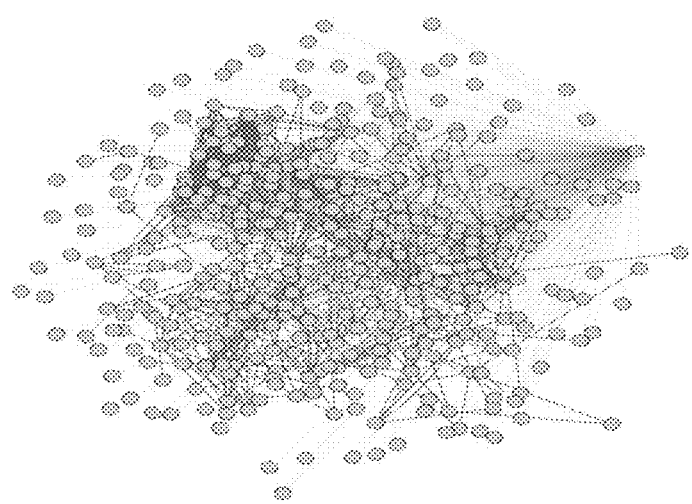
Figure 16:
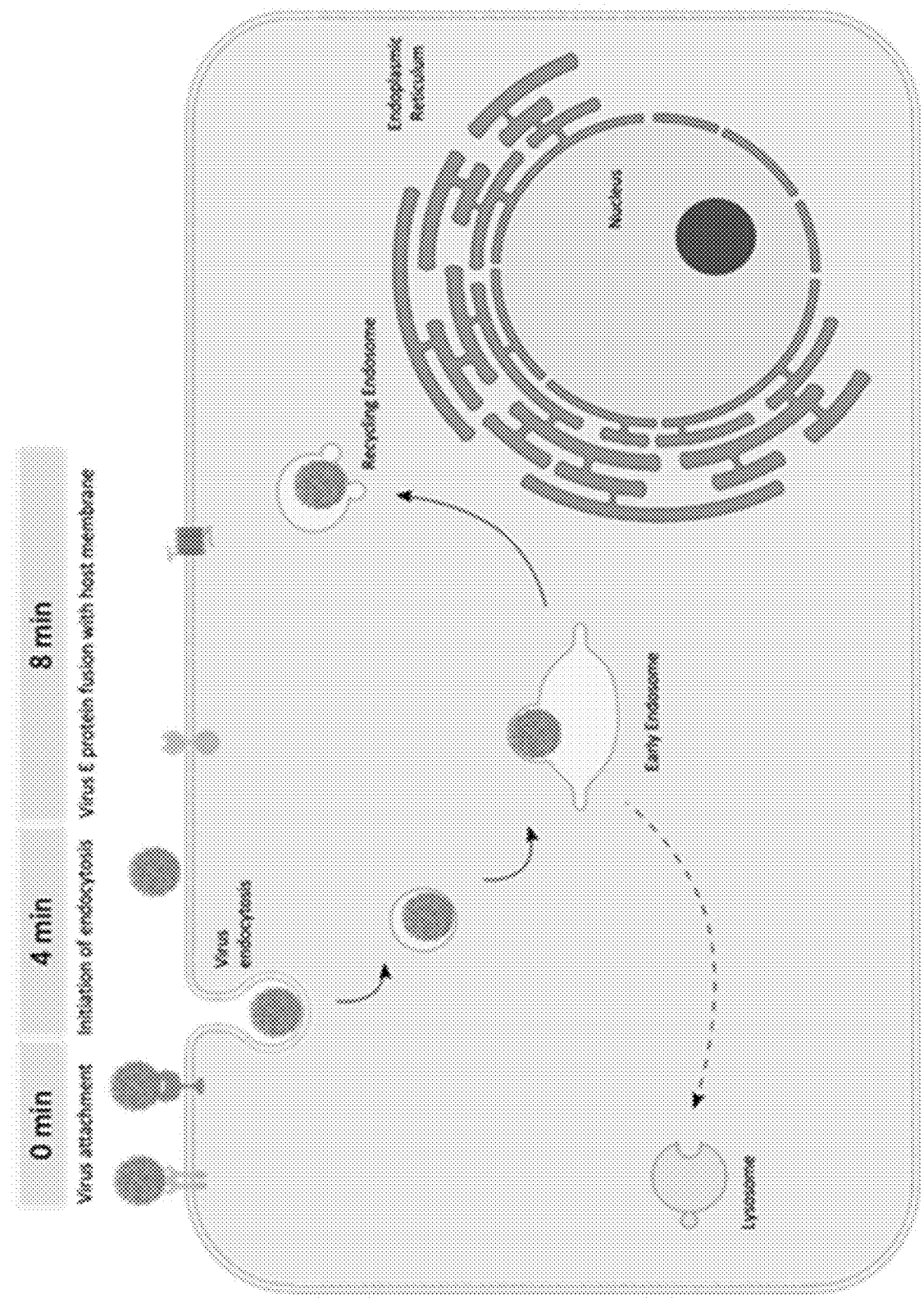
FIG. 16 represents different subcellular localizations of Zika virus during its entry into Vero cells. ZIKV binds to the cell surface proteins at 0° C. and 0 minutes of Virus entry. After incubation at 37° C., the viruses are rapidly internalized to early endosomes, where it fuses with the host membrane to release genomic material into the cytoplasm. This quick and temporal localization of ZIKV in early endosome and the virus fusion process are in accordance with the results for expression of RAB5 dominant negative protein as published earlier (Meertens et al., 2017). Interestingly, at 8 minutes, ZIKV was found to interact with RABi1 suggesting it's localization in the recycling endosome.

The design and synthesis of the multifunctional probe is shown in Scheme 1 shown below. Moreover, we checked the feasibility of crosslink using two proteins (Concanavalin A and Fetuin) with known interaction (FIG. 13). Additionally, we demonstrated the applicability of this technology in the study of virus infection below.

The outbreak of Zika in early 2016 created worldwide urgency and demanded rapid development in research pertaining to Zika virus. Till date, this has led to the elucidation of structure of Zika virus, development of neutralizing antibodies, and exploration of the host factors involved in Zika entry into various cell lines. The later, though, is not completely unraveled, primarily due to the lack of a robust and high-throughput method to study the enveloped virus internalization. Here, we present a novel technology to trace the early stage entry of Zika virus into host cells. Zika virus was labeled on its surface with a chemical probe, which carries a UV-photocrosslinker to covalently link any virus-interacting proteins on UV exposure, and a biotin tag for subsequent enrichment and mass spectrometric identification. The 'surface modified' virus was allowed to either attach or enter Vero cells, followed by UV-photocrosslinking at certain time points, to reveal the receptor or other host proteins critical for virus internalization. We identified Neural Cell Adhesion Molecule (NCAM1) as the potential attachment factor/receptor for Zika virus, which we validated using antibody inhibition in Vero cells and overexpression into HEK 293T cells. Furthermore, using the technology we isolated other direct interactors of Zika virus, which might be critical for its pathogenesis. The method could serve as a universal tool to map the entry pathway of other enveloped virus, including Dengue and West Nile from the family Flaviviridae.

Zika was first discovered in the Zika valley of Uganda in 1947, however, only after the recent outbreak in South Americas it was declared a health emergency. Early cases were observed with skin rash, fever and other mild symptoms, but later a close relation between Zika infection and microcephaly in newborns and Guillain-Barré syndrome (GBS) in adults were reported. The primary mode of transmission to humans is through an infected mosquito, *Aedes aegypti*.

Zika belongs to Flaviviridae, the same family as dengue virus (DENV), West Nile virus (WNV), Japanese encephalitis virus (JEV), and yellow fever virus (YFV). It is a positive-strand RNA virus with a genome of about 11,000 nucleotides, which are translated into a single polyprotein, further processed by viral and host proteases to form three structural and seven non-structural proteins. Like other flavivirus, a mature Zika virus is composed of a nucleocapsid enclosed in an icosahedral shell containing 180 copies (90 dimers) each of the envelop E and membrane M proteins. E protein is the key surface glycoprotein involved in receptor-binding and membrane fusion with the host cell.

Zika virus has been the focus of immense investigation since the recent epidemic. Initial studies on Zika structure revealed its structural similarity with other virus from Flaviviridae, besides the peculiar Asn154 glycosylation site present on each of the E proteins, the thermal stability, and the compact surface of the virus. Progress has also been made towards developing therapeutics, by isolating neutralizing monoclonal antibodies from infected human subjects. However, a much deeper understanding of the immune response elicited and the various virus-host interactions are required for the rapid development of antiviral agents, both of which are limited due to lack of available high-throughput methods. Furthermore, mapping the host factors critical for viral infection will highlight the molecular pathways manipulated by the virus to maneuver to its benefits.

Figure 8A:
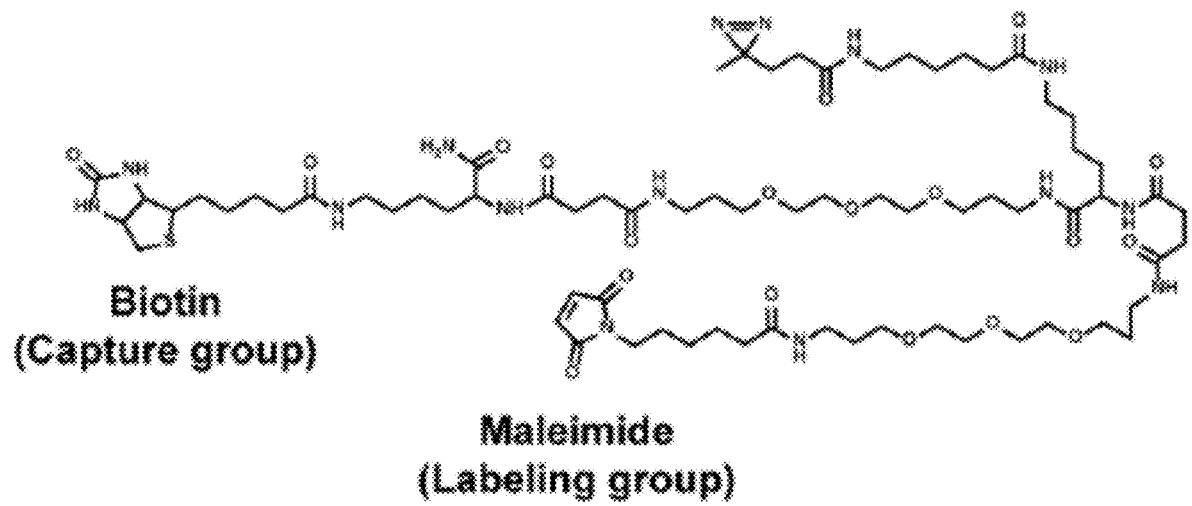
FIGS. 8A-8C show chemically labelling ZIKV surface E proteins and capturing virus-interacting proteins.
Figure 8B:
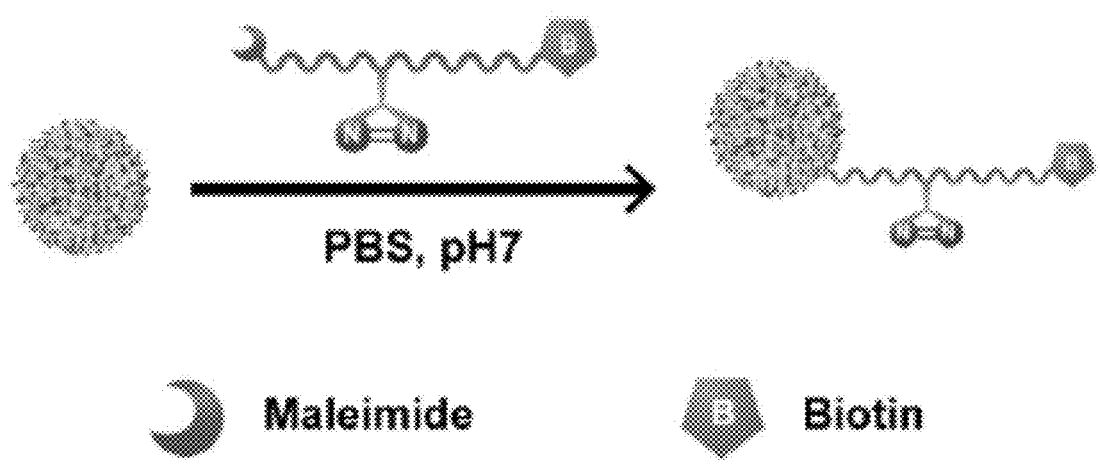
Figure 8C:
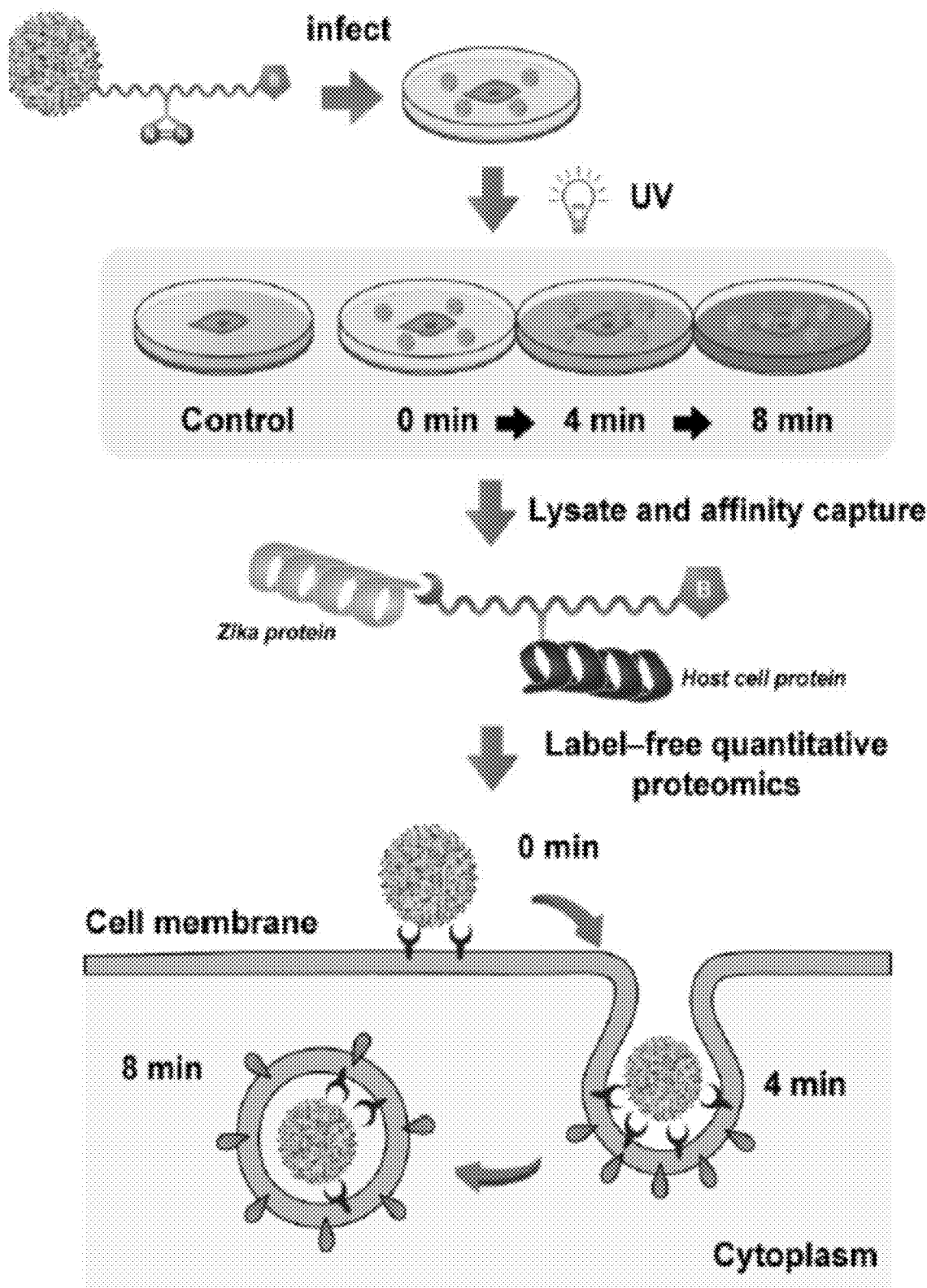

Here, we present a novel chemical proteomic technology to trace the virus entry and identify virus-interacting proteins. The virus 'surface proteins' were chemically labeled using a probe that bears UV-photocrosslinker and a biotin handle (FIG. 8B). The trifunctionalized probe contains a cysteine-reactive maleimide group to label the virus surface proteins, a diazirine for covalently crosslinking the virus-interacting proteins on exposure to UV light, and a biotin tag for enrichment and downstream mass spectrometric analysis (FIG. 8A). The three functionalities are separated by a polyethylene glycol (PEG)-like linker to confer membrane impermeability so as to allow endocytic viral entry, while offering the flexibility for efficient crosslinking and enrichment. The labeled Zika was used to infect Vero cells and proteins were crosslinked at fixed time points to identify the virus receptors and elucidate the virus entry mechanism (FIG. 8C). Vero cells were chosen due to the well-established high infectivity of Zika, and the diazirine group was selected due to its high selectivity in protein crosslinking. The diazirine group allows tracing the virus movement in 'real-time', which is challenging due to the highly dynamic nature of the process and the transient virus-host protein interactions. Moreover, the crosslinking chemistry permits the identification of receptors, which otherwise being a hydrophobic membrane protein, presents its own challenges. Compared to the previously reported mass spectrometric method for identification of receptors, specific to glycoproteins, our method offers the additional advantage of covalently linking proteins at different time points, thus serving the dual purpose of identification of receptors and other host factors involved in different stages of virus entry. Lastly, this novel technology can be applied to relatively unstable enveloped viruses, owing to the minimal labeling by cysteine-reactive maleimide group.

Example of Virus Labeling.

Our understanding of ZIKV internalization and cellular trafficking would greatly benefit from a systematic, temporal characterization of major proteins involved in the dynamic virus entry. Real-time fluorescence microscopy has been used to study the transport, acidification, and fusion of single virus. The movement of single virus demonstrated an intriguing and dynamic process. The molecular information, in particular protein machinery involved in the process, is typically limited to labeled molecules in the amazing technique. On the other hand, affinity and chemical proteomics studies identified virus-interacting proteins. The molecular mechanisms and dynamic virus-host interactions responsible for the internalization of ZIKV, however, have remained unresolved.

We think a systematic quantitative measurement of temporal changes in virus-protein interactions is extremely valuable for the identification of host molecules as potential therapeutic targets. We have previously used chemical proteomics strategies and modified a nanoparticle, polyamidoamine generation 3 (PAMAM G3) dendrimer, to understand the endocytic pathways of a nanoparticle. Here, we expand the concept and hypothesize that chemical modification of ZIKV would not significantly affect its infectivity and would allow us to track the virus entry into living cells and identify virus-interacting proteins by mass spectrometry (MS), revealing the spatiotemporal distribution of the key proteins involved in the pathways for ZIKV entry and trafficking.

We devised and synthesized a multifunctional chemical probe (FIG. 8A) bearing a labeling group that conjugates the probe to the ZIKV surface, a photo-reactive group that allows for covalent cross-linking of ZIKV proteins to interacting host cell proteins upon UV exposure, and an isolation tag (e.g. biotin) for purifying the interacting proteins for quantitative MS analysis, thus facilitating the investigation of host-pathogen interactomes in a time-resolved manner (FIG. 8B). We chose the maleimide group to label the virus through its specific conjugation with thiol groups on the virus surface proteins at physiological condition to form a stable thioether linkage. As sulfhydryls thiols are present in most proteins but are not as abundant as primary amines, we expect it would have a minimal labeling effect on the ZIKV activity. ZIKV, like other flaviviruses and enveloped viruses in general, is quite unstable and prone to undergo structural changes under external influence. Considering the virus stability and infectivity, we preferred minimal labeling of virus through the maleimide-thiol conjugation under mild conditions at neutral pH. The three functionalities are separated by a polyethylene glycol (PEG)-like linker to improve water solubility, while offering the flexibility for efficient crosslinking and enrichment.

The labeling was first examined with a standard protein and then with intact ZIKV. Bovine serum albumin (BSA) was incubated with 1 mM of reagent in phosphate buffer pH 7 at 4° C. and the labeled protein was enriched on streptavidin beads and analyzed by SDS-PAGE. The labeling efficiency was estimated to be 25-30% (FIGS. 14A, 14B, and 14C). Next, we examined the effect of labeling purified ZIKV with several concentrations and labeling time points by the plague assay. No loss of infectivity was observed under labeling conditions for 1 mM reagent concentration (FIG. 14D). After labeling, modified ZIKV was lysed, and the labeled ZIKV surface proteins were purified on streptavidin beads and assessed by silver stain (FIG. 17B), Western Blotting (FIG. 17C) using the 4G2 antibody against the E protein and MS analyses (FIG. 14D). Multiple unique peptides from E protein were identified and quantified across the three time points of labeling by MS (FIGS. 15A-15D). We did not identify any peptide from virus membrane (M) protein, capsid, or any of the non-structural proteins of ZIKV, further confirming the exclusive tagging of virus surface with the reagent. This result is primarily owing to the membrane impermeable attribute of the reagent imparted by the PEGylated linkers. Hence, we concluded that the 'minimal' labeling of virus achieved by cysteine-reactive maleimide group does not perturb the infectivity of the virus.

We used the labeled ZIKV to infect Vero cells and interacting proteins were crosslinked at fixed time points to identify the virus host factors and elucidate the virus entry mechanism (FIG. 8C). Flavivirus are quite promiscuous in their selection of receptors for entry to different cells. The complex entry mechanism might involve multiple receptor interactions to help virus internalize. Though some previous studies have identified AXL, a TAM family tyrosine kinase, as a putative receptor for ZIKV, some conflicting evidence suggests that the virus might employ multiple different classes of receptors for entry. Furthermore, while most of the viruses are believed to enter cells by clathrin-mediated endocytosis, there is no evidence suggesting the absence of any parallel mode of virus entry. The complexity of the flavivirus entry mechanism hints at the presence of varied virus-protein interactions after membrane recruitment of host cellular proteins to initiate viral infection. In order to identify ZIKV receptors, we allowed the virus to attach to the cells at 4° C. for 1 hour, followed by UV photocrosslinking on ice. For the virus entry, we chose 4 and 8 minutes according to a previous study that indicates the membrane fusion of a similar flavivirus at 512 seconds post-binding, during its entry into Vero cells. After crosslinking proteins at designated time points of attachment (designated as 0 min) or entry (4 and 8 min), cells were harvested and proteins were extracted, followed by the enrichment using avidin beads. We reasoned that the chemical probe on the virus surface only reacts with proteins in direct contact with ZIKV, which can subsequently withstand vigorous washing conditions. Specifically, covalent crosslinking and strong biotin-avidin interaction can withstand washing with 0.1% SDS to remove non-specifically bound proteins. The tryptic peptides derived from enriched samples were then analyzed by nanoflow HPLC coupled to high-resolution mass spectrometry. Proteins were identified by a shotgun proteomic strategy and quantitated using the label-free method to distinguish crosslinked proteins from nonspecifically bound proteins and to measure their relative abundance across three time points.

In total, we identified around 300 crosslinked proteins across three time points, out of which more than 70 proteins are previously implicated in virus infection (FIG. 11A). Each experiment was performed in biological triplicates. The principal component analysis (PCA) shows that all biological replicates are tightly together and each time point is well-separated, meaning the samples cluster by the nature of sample but not the batch (FIG. 11B). The PCA analysis also indicates that distinctive proteins were crosslinked at three different time points, suggesting that the strategy was able to reveal the temporal distribution of the interacting proteins crosslinked with ZIKV during the virus' early entry. Gene ontology (GO) analysis, as expected, indicated proteins annotated as extracellular, membrane, and vesicles were significantly overrepresented in the crosslinked proteins across all time points (FIG. 11C).

To further investigate whether the strategy was also capable of correlating spatial information with the virus-crosslinked proteins, we performed the ANOVA test and Cytoscape to determine whether there is statistical overrepresentation of specific genes or proteins in the sample at specific time points and identify proteins specific at the attachment or cellular entry stages (FIG. 11D and FIG. 15). We have shown that a number of proteins, previously reported as the receptors in other systems, were identified at the attachment stage (0 min). Notably, neural cell adhesion molecule (NCAM1), which was reported as a receptor for rabies virus[28], was only identified at 0 minutes. Integrins are highly conserved transmembrane glycoproteins which serve as receptors for a broad range of viruses[29, 30] and we identified integrin alpha-3 (ITGA3) at 0 and 4 minutes, and integrin beta-1 (ITGB1) at 8 minutes of infection. CD81, a known co-receptor for Hepatitis C virus (HCV)[31] and shown to interact with the viral envelope protein E2[32], was also identified with high confidence at 0 minute. A few other noticeable proteins crosslinked specifically at 0 minute include AP2M1 and calmodulin 1 (CALM1). It is the μ2 subunit of adaptor protein-2 (AP-2) complex that recognizes the tyrosine-rich sorting signals on the cytoplasmic tail of receptor proteins and directly interacts with them[33]. Our crosslinking experiment validates the complex's structural assembly on the membrane and only AP2M1 was selectively crosslinked at 0 minutes of infection, while no other AP-2 subunits were observed. AP2M1 has further been shown to modulate early-stage infectious entry of HCV, in its phosphorylated form. CALM1 is a clathrin adaptor protein recruited to the membrane and involved in endocytosis and interestingly, a recently published study identifies Calmodulin-like protein (CALML5) as a ZIKV host factor.

We further demonstrated that the strategy allowed us to identify clusters of proteins representing a temporal shift of ZIKV subcellular localizations and in many cases, the subcellular localizations and functions of crosslinked proteins highly correlate to the temporal information (FIG. 16). Following the initiation of receptor-mediated entry into host cells, we observed that ZIKV encounters an acidic environment in the endosomes, which was previously reported[16]. Vacuolar ATPases (v-ATPases) are known to be required in order to maintain the acidic condition inside these endosomes. We identified multiple v-ATPases, ATP6V0D1, ATP6V1H, and ATP6V1G1, at the three time points, highlighting the importance of an acidic environment in ZIKV endocytosis. More importantly, ATP6V1B2, a key mediator of viral fusion with the endosomal membrane and RNA release in SINV, DENV, WNV, YFV infections, was cross-linked exclusively at 8 mins of infection, implying that ZIKV RNAs are released into cytoplasm at this time point. At 8 minutes of infection, we also identified an isoform of a key component of recycling endosomes, RAB11A. The role of RAB11A in transport of viral ribonucleoprotein (vRNP) or core proteins to plasma membrane for the generation of new virus particles of influenza and HCV, respectively, is well documented. However, some virus may also utilize the recycling endosomal pathway to evade lysosomal degradation. Our study suggests the use of the recycling pathway by ZIKV after entry. Besides RAB11, we also observed RAB5A at 8 minutes. Previous studies have established the importance of RAB5 in the entry of ZIKV, DENV, and WNV[37]. The identification of RAB5 and RAB1 in our chemical proteomics experiment at a late time point of entry is consistent with the published data on JEV, a neurovirulent pathogen from the flavivirus genus structurally similar to the ZIKV. Other proteins exclusively identified at 8 minutes of infection include HSPA8, also known as Hsc70 (heat shock cognate 70), known for its role in vesicle uncoating in the later stage of endocytosis.

We also observed certain proteins enriched in all three time points such as STAT1, a key mediator of Type-I Interferon Signaling. It has been reported that ZIKV suppresses the host immune response by inhibiting the type-I interferon signaling pathway. Previous studies also have suggested the mechanism of blocking immune response by ZIKV as either the degradation of STAT2 (Signal Transducer and Activator of Transcription), or antagonism of STAT1 and STAT2 phosphorylation. We identified STAT1 across all the three time points. The receptor-activated C kinase (RACK1), which mediates the interactions between IFN receptor and STAT1, was also identified as a ZIKV-interacting protein. Previously, a different class of virus was shown to interact with RACK1, thus initiating the dissociation of RACK1-STAT1 complex and inhibition of interferon signaling by the virus 4. Our study emphasizes the involvement of both RACK1 and STAT1 in the immune response elicited by the ZIKV infection, suggesting ZIKV might employ a similar approach to suppress the host immune response.

Figure 9:
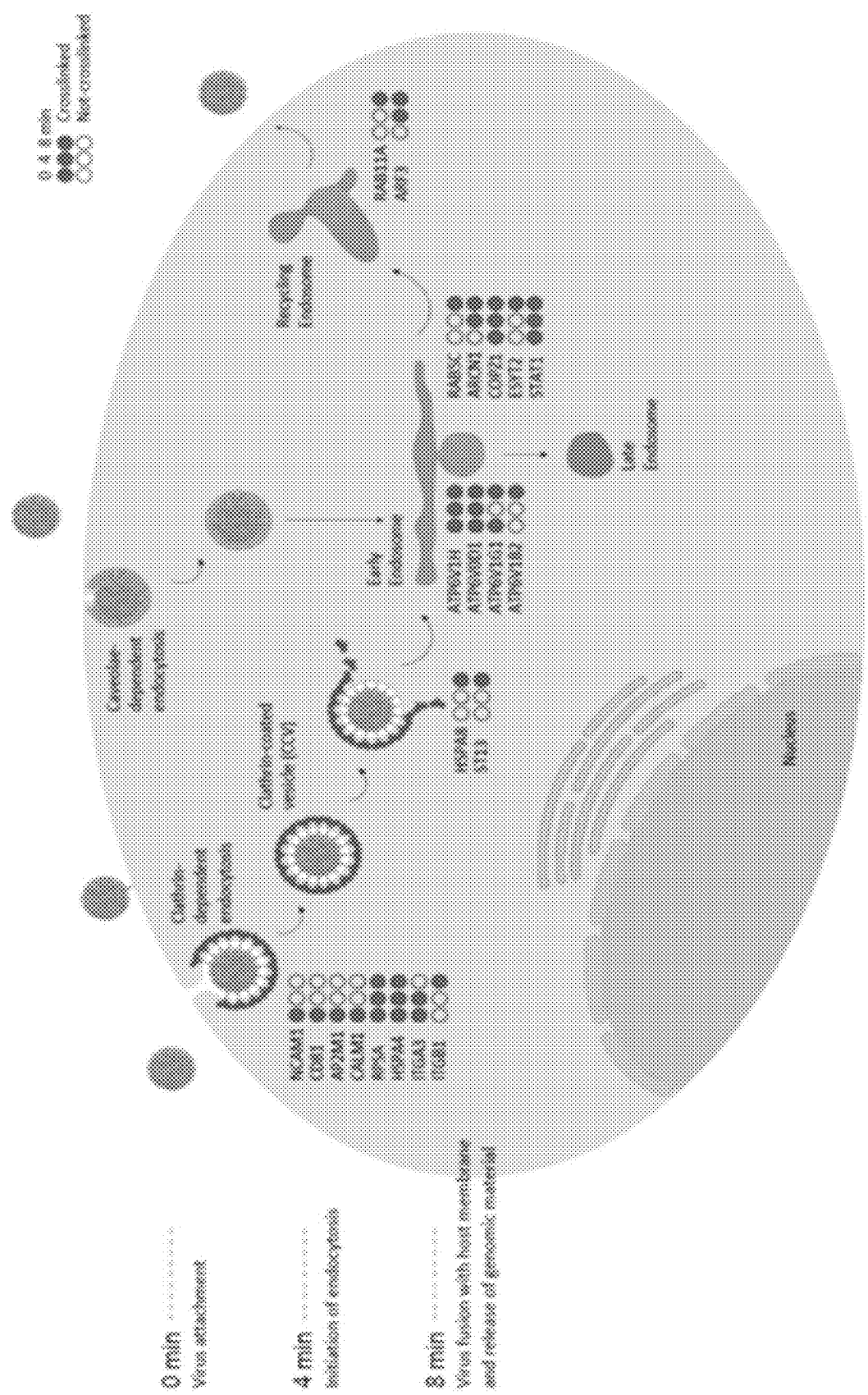
FIG. 9 shows a proposed endocytosis pathway of ZIKV entry into host cells, highlighting proteins crosslinked at different time points of infection.

To identify any parallel mode of virus entry mechanisms, we examined temporally ZIKV-crosslinked proteins against protein components involved in major endocytic mechanisms for ZIKV internalization (FIG. 9). Prior studies showed ZIKV infection could be prevented by lysosomotropic agents which neutralize the normally acidic pH of endosomal compartments and was also blocked by chlorpromazine, suggesting the requirement of clathrin-mediated endocytosis and low pH for ZIKV infection. In our study, ITGB1, AP2M1, HSPA8, RAB5C, CDC42, RAC1, and RAB11 were crosslinked, confirming the clathrin-mediated pathway employed by the virus to infect Vero cells. Furthermore, identification of COPZ1, ARCN1, ITGA3, FLNA, FLNB, and FLNC also indicated the utilization of a caveolar-mediated pathway by ZIKV for endocytosis.

Figure 10A:
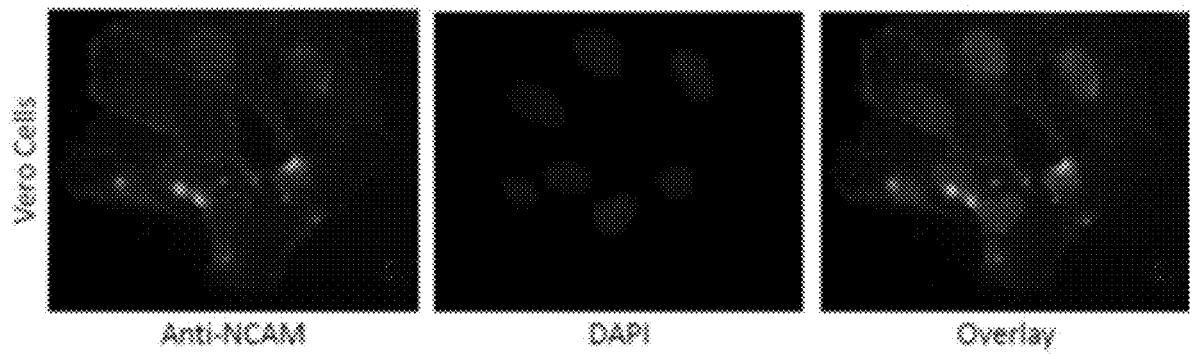
FIGS. 10A-10D show identification of NCAM as potential host receptor for ZIKV.
Figure 10B:
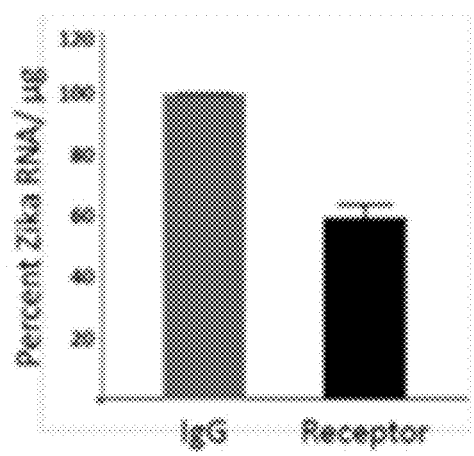
Figure 10C:
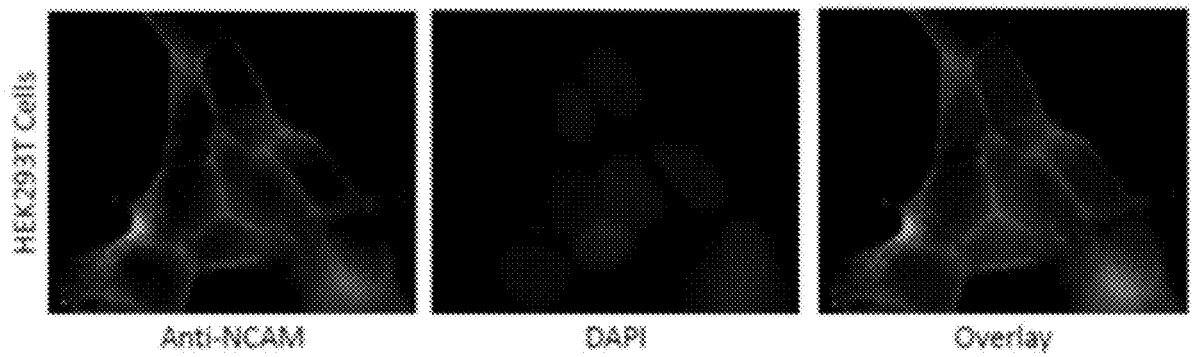
Figure 10D:
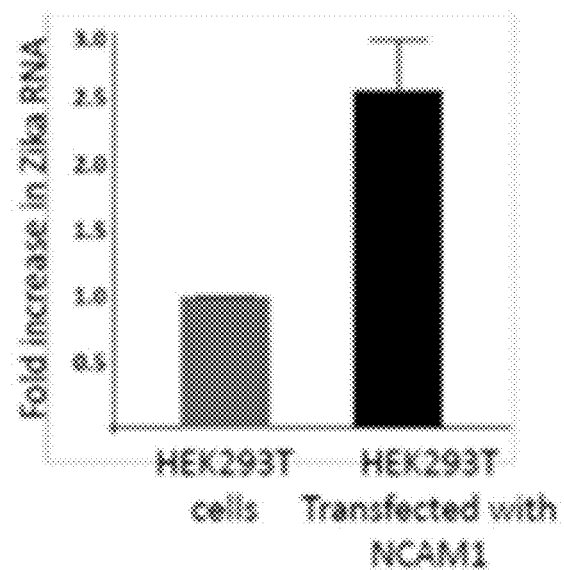
Figure 11A:
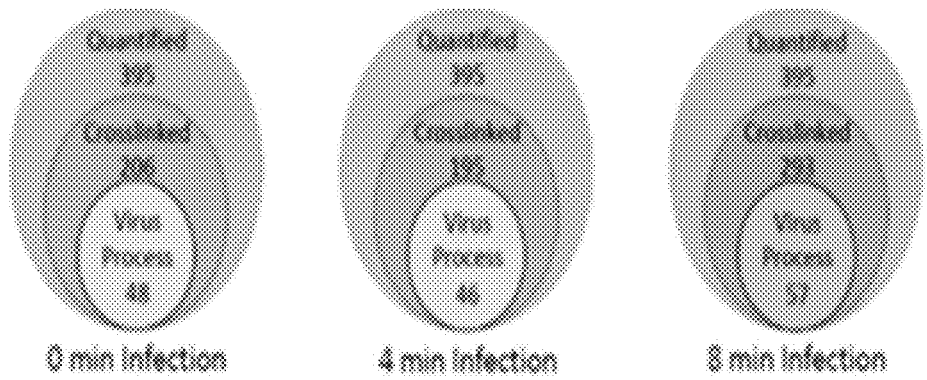
FIGS. 11A-11D demonstrate proteins crosslinked at different time points of ZIKV infection.
Figure 11B:
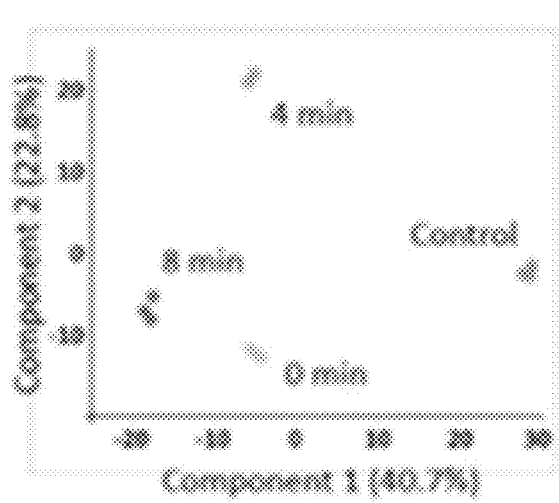
Figure 11C:
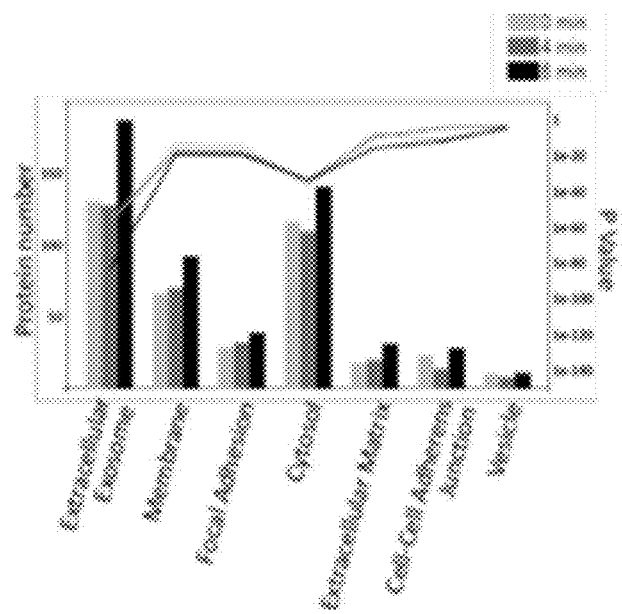
Figure 11D:
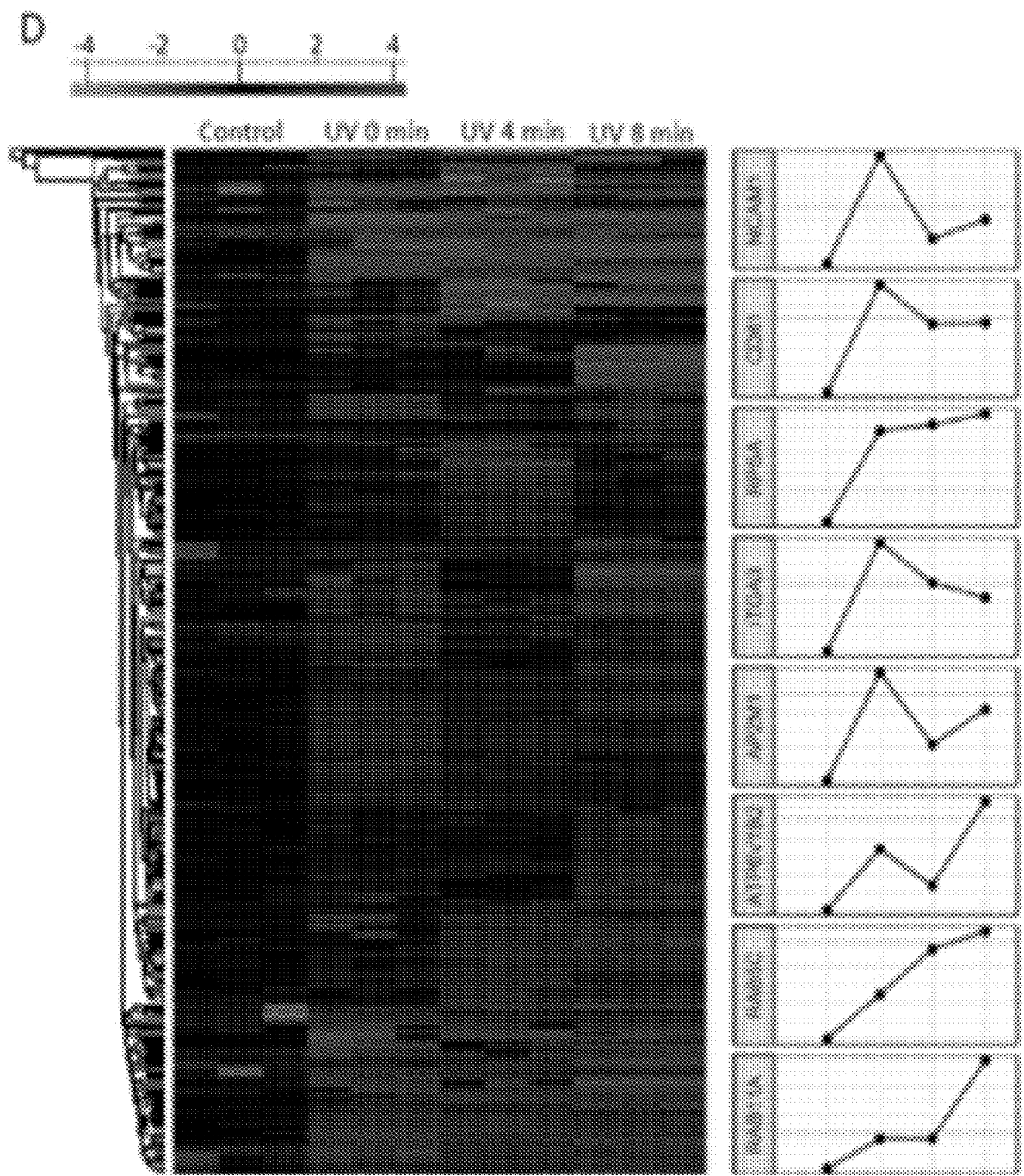
Figure 12:
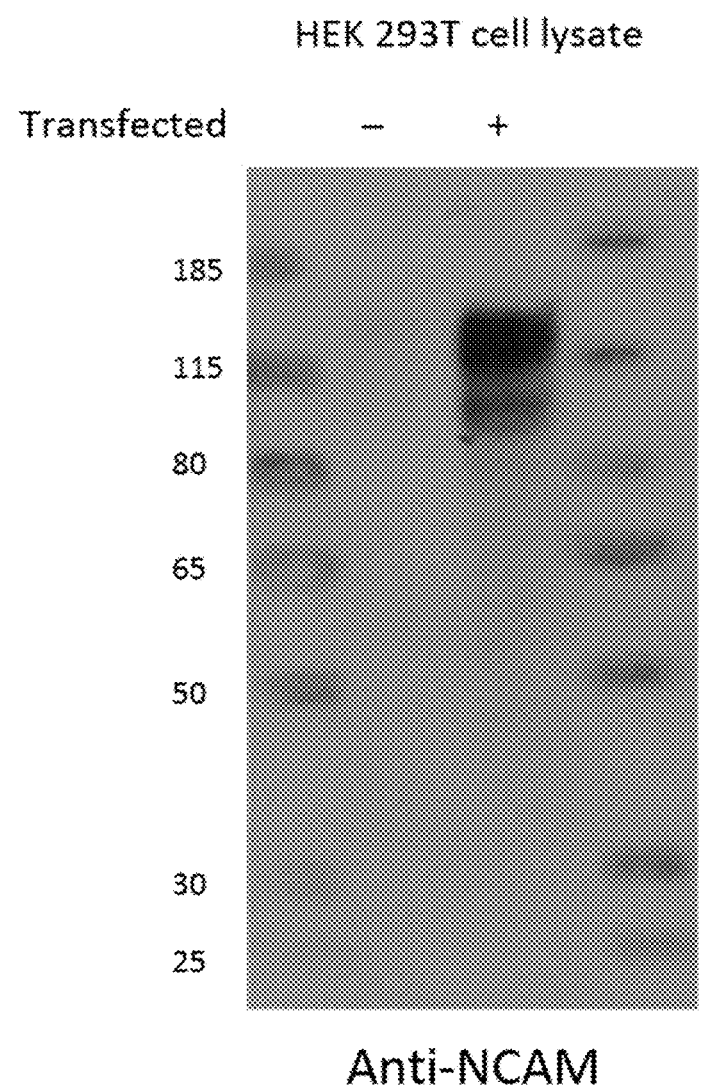
FIG. 12 shows Western blot for overexpressed NCAM1 in HEK293T cells. 48 hours post transfection, cells were collected and lysed, and probed against anti-NCAM followed by anti-mouse IgG HRP-conjugated secondary antibody. A strong signal was observed in 10 µg lysate after NCAM overexpression, while no significant band was observed for 10 µg of non-transfected HEK293T cell lysate.
Figure 17A:
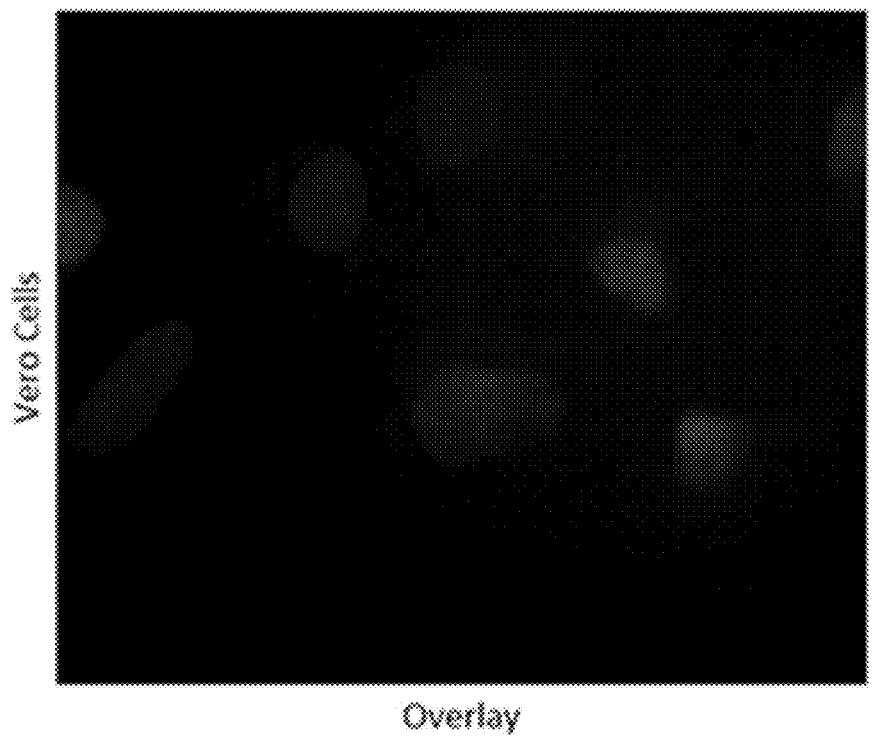
FIGS. 17A-17B show immunofluorescence for the control cells for anti-NCAM inhibition of Vero cells and NCAM overexpression in HEK293T cells.
Figure 17B:
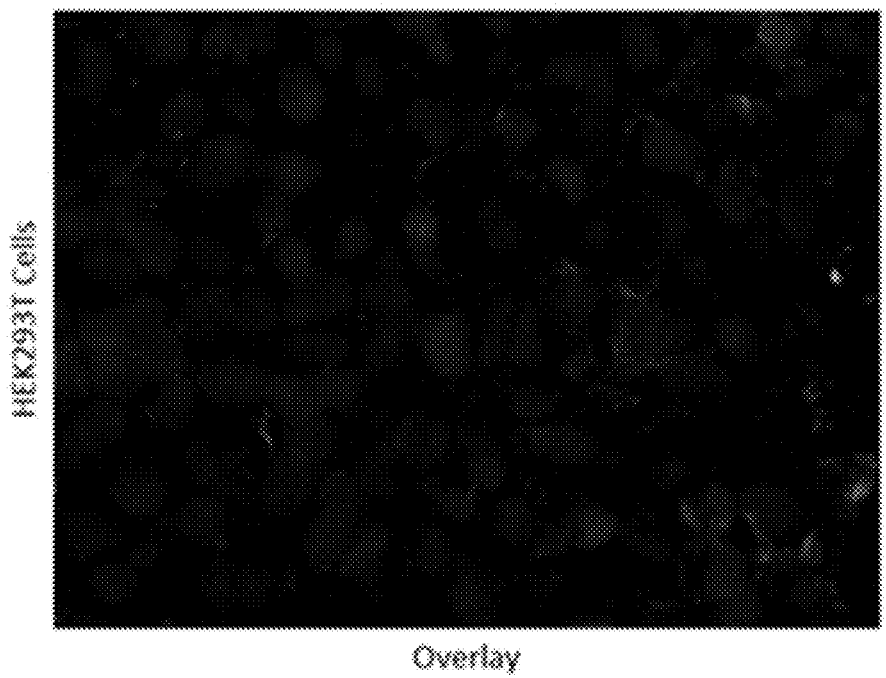
Figure 18A:
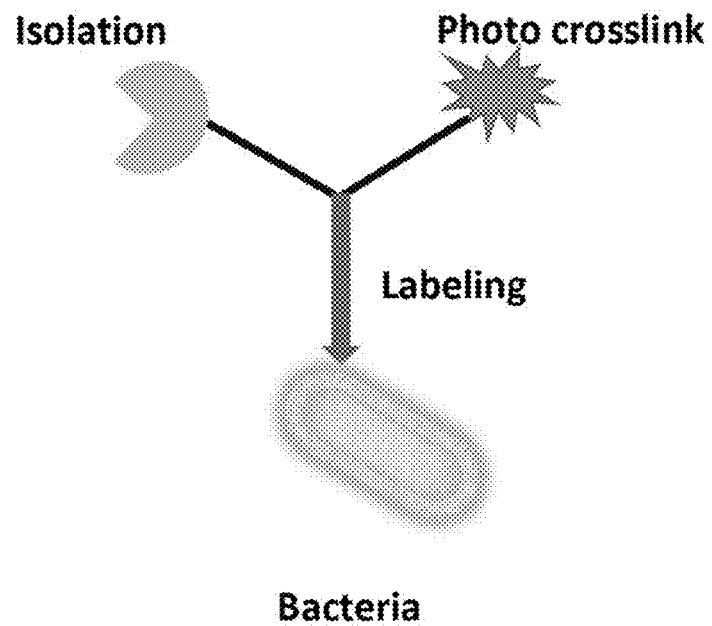
FIG. 18A shows diagram of labeling bacteria to investigate bacteria interacting proteins during infection.
Figure 18B:
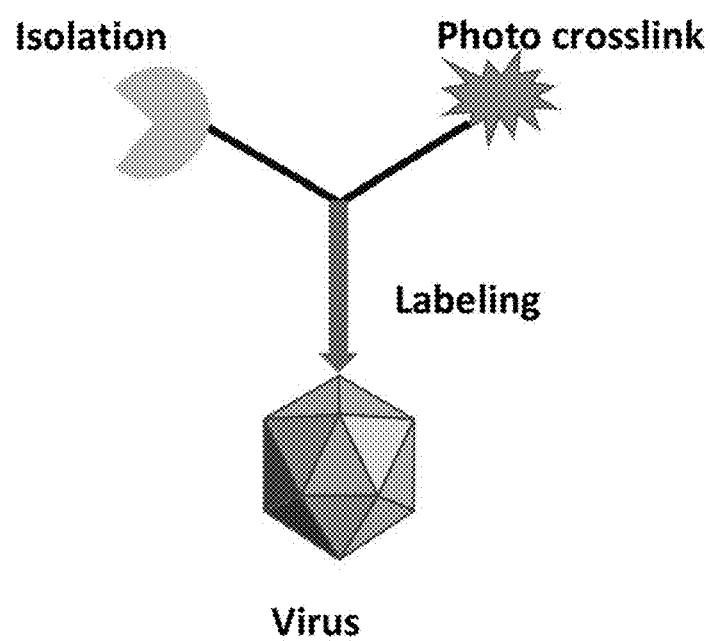
FIG. 18B shows diagram of labeling virus.
Figure 19:
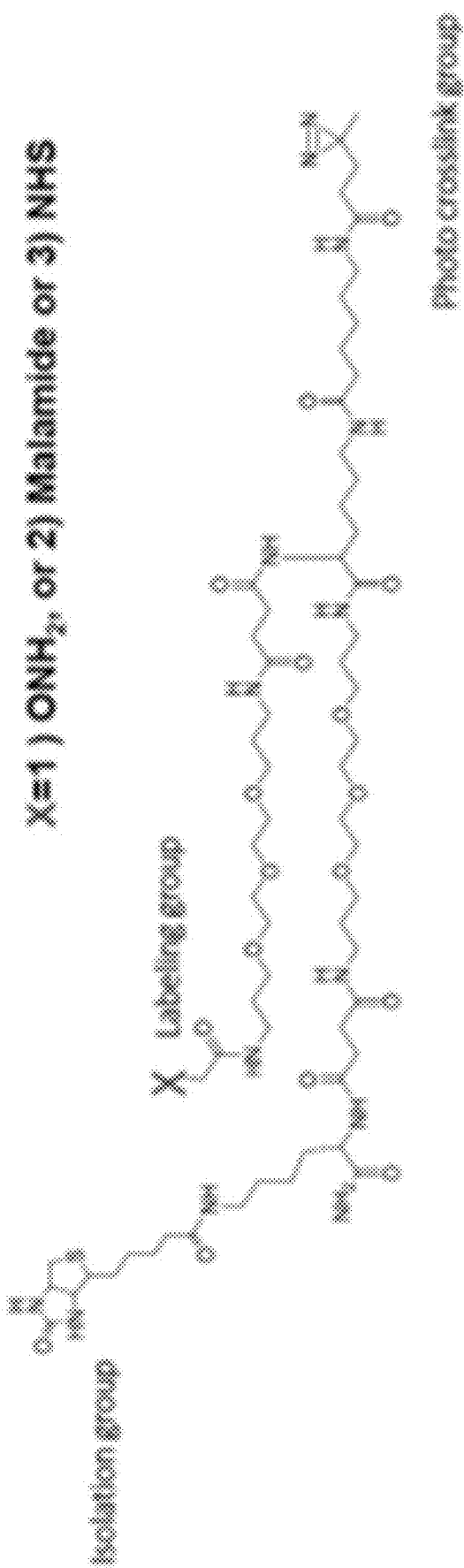
FIG. 19 shows diagram of labeling reagents on bacteria and virus to analyze interacting proteins during infection.
Figure 20:
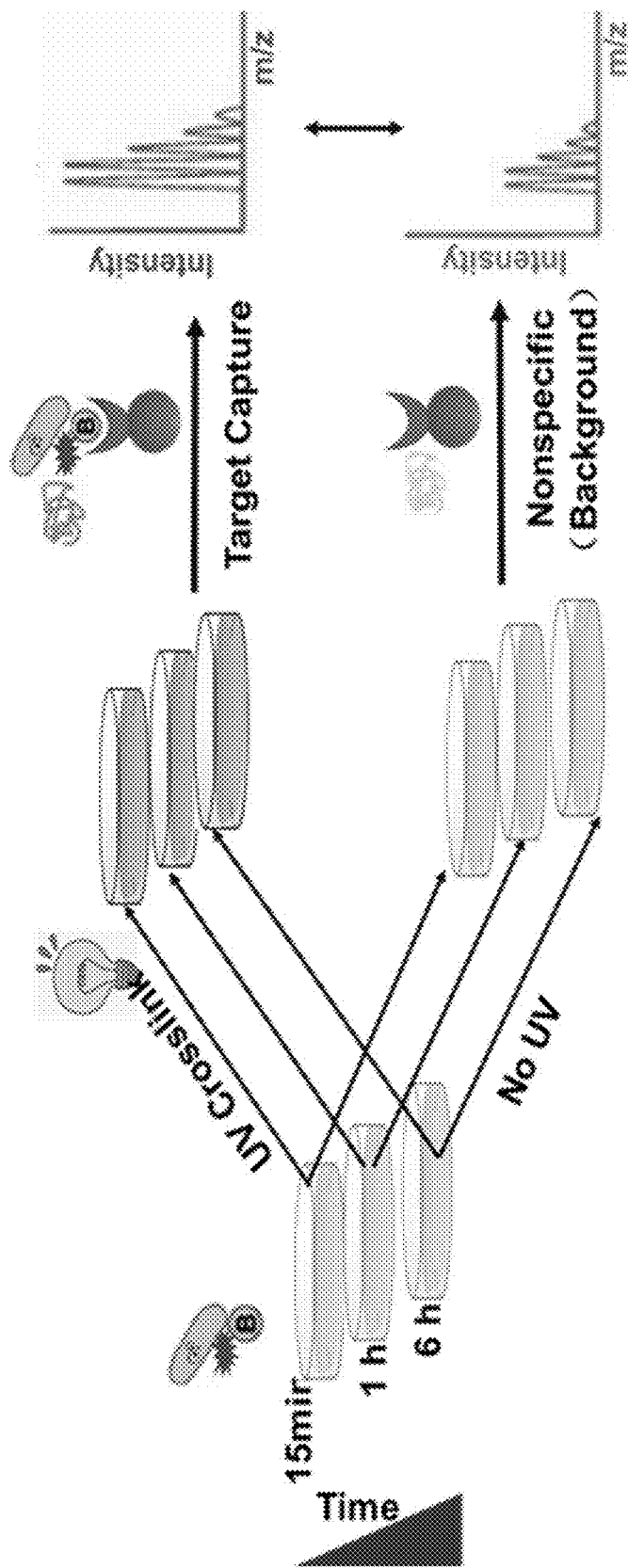
FIG. 20 shows illustration of capturing bacteria-interaction proteins at different infection time point for mass spectrometry analyses.

Finally, considering NCAM1 was exclusively crosslinked at 0 minute and NCAM is abundantly expressed in brain, we further examined whether NCAM1 is a potential receptor for ZIKV infection leading to neurological disorders. In the first validation experiment, we investigated if antibody blocking of NCAM causes reduction in ZIKV infectivity. For this purpose, we employed CD56 antibody which binds to the extracellular immunoglobulin-like domains present in all three isoforms of NCAM. We first tested the ability of the antibody to bind to the Vero cell membrane using immunofluorescence without membrane permeabilization, and observed a strong fluorescence signal (FIG. 10A and FIG. 17). Then, we incubated Vero cells with CD56 or IgG as control for 45 minutes at room temperature, prior to infection by ZIKA at Multiplicity of infection (MOI) of 0.1. Cellular RNAs were extracted after 24 hours infection and were quantitated using qRT-PCR. We noticed a significant reduction in internalized ZIKA RNAs across three biological replicates, indicating NCAM as a likely host receptor in ZIKV infection (FIG. 10B). To further confirm the receptor activity of NCAM, we overexpressed NCAM1 in HEK 293T cells and performed attachment assays with ZIKV. HEK 293T cells lack NCAM protein and have minimal infectivity by ZIKV, which makes them an ideal system to test the receptor activity for ZIKV. HEK 293T cells were transfected with expression plasmid encoding NCAM1 and the expression of NCAM1 was confirmed by Western Blotting 48 hours post-transfection (FIG. 10C and FIG. 12). The immunofluorescence image revealed that NCAM1 is located on the membrane of the transfected HEK 293T cells. HEK 293T cells and transfected cells were incubated with ZIKV for 1 hour at 4° C. Cells were washed and harvested, and qRT-PCR was used to quantitate ZIKV RNAs. We found a two- to three-fold increase of ZIKV RNA in the transfected cells (FIG. 10D).

In conclusion, we have developed a chemical proteomic approach in which virus were chemically tagged with a biocompatible probe, to reveal the virus-host interactions in real-time. In this study, we applied the technology to ZIKV and identified multiple ZIKA-interacting proteins that indicate ZIKV subcellular localizations and potential entry mechanisms, among which a new ZIKV receptor was discovered and validated through virus attachment and entry assays. Inhibition of NCAM by antibody reduced the ZIKV entry into Vero cells, while its overexpression in HEK 293T cells increased viral binding. The strategy highlighted its unique feature that allowed us to track the virus movement in 'real-time', which is challenging due to the highly dynamic nature of the process and the transient virus-host protein interactions 9. Moreover, the crosslinking chemistry permits the identification of potential receptors which present analytical challenges to identify the interaction on cell membrane[50, 51]. Compared to the previously reported mass spectrometric methods for the identification of receptors specific to glycoproteins[10, 11], our method offers the additional advantage of covalently linking proteins at different time points, thus serving the dual purpose of identification of receptors and other host factors involved at different stages of virus entry. Lastly, this novel technology can be applied to relatively unstable enveloped viruses, owing to the minimal labeling by cysteine-reactive maleimide group.

Experimental Procedures for Virus Labeling

Cells and Reagents: Vero (African green monkey kidney) and HEK 293T (human embryonic kidney) cells were maintained in DMEM media supplemented with heat-inactivated 10% FBS, at 37° C. and under 5% $CO_2$. Low passage cells were used for the virus propagation and all other infection experiments. The anti-NCAM monoclonal antibody for blocking cell surface protein and immunofluorescence assay was purchased from BD Biosciences (Cat. No. 559043), while the antibody for Western blot was obtained from Cell Signaling (Cat. No. 3576). Streptavidin-HRP antibody was bought from R&D Systems (Cat. No. DY998), and 4G2 antibody was generously provided by Richard Kuhn, Purdue University. All reagents for synthesis were obtained from Sigma-Aldrich. ChemPep Inc, Peptides International Inc, Novabiochem (EMD Millipore), and Mature Zika Preparation Approximately $1\times10^9$ Vero-Furin cells (15) were infected at a multiplicity of infection (MOI) of 0.1 with Zika virus (strain H/PF/2013) at 37° C. (16). Virus particles were purified from media collected at 60 and 72 hours post infection (hpi) according to the procedure below. Briefly, virus particles were precipitated from the media with 8% polyethylene glycol (PEG) 8000 overnight at 4° C. pelleted at 8891×g for 50 minutes at 4° C. Re-suspended particles were pelleted through a 24% sucrose cushion, re-suspended in 0.5 mL NTE buffer (20 mM Tris pH 8.0, 120 mM NaCl, 1 mM EDTA) and purified with a discontinuous gradient in 5% intervals from 35% to 10% K-tartrate, 20 mM Tris pH 8.0, 1 mM EDTA. Mature virus was extracted from the gradient, concentrated and buffer exchanged into NTE buffer.

Plaque Assay

The plaque assay was performed as described below. Purified Zika virus was diluted serially in the order of ten folds, and incubated with monolayers of Vero cells for 1 hour at room temperature. Cells were layered with agarose, and incubated at 37° C. for 3 days. Plaques were counted following cell staining using Neutral red.

Synthesis and Purification of a Multi-Functional Chemical Probe

The virus-labeling chemical probe was synthesized on the Rink-Amide-AM-Resin (200-400 mesh) 1% DVB manually, using standard solid phase peptide synthesis approach (Scheme 1). A 20% piperidine solution in DMF (N,N-Dimethylformamide) was used to deprotect the fmoc (9-Fluorenylmethoxycarbonyl) groups, while 95% TFA (Trifluoroacetic acid) was used for boc (tert-Butoxycarbonyl) group deprotection. HCTU (O-(1H-6-Chlorobenzotriazole-1-yl)-1,1,3,3-tetramethyluronium hexafluorophosphate) was utilized as an activating agent for the carboxyl group on the incoming reactant, in presence of the base NMM (4-methylmorpholine). The synthesis was performed on the 30 μmol scale and using 2.5-fold excess of the reagents compared to the resin. Each step involved the deprotection of amine group, activation of carboxyl group followed by coupling reaction. The excess reagents were removed by thorough washing of beads by DMF. Ninhydrin test was performed after each deprotection and coupling reaction.

Scheme 1: Synthesis of a Chemo-Proteomic Probe[a]

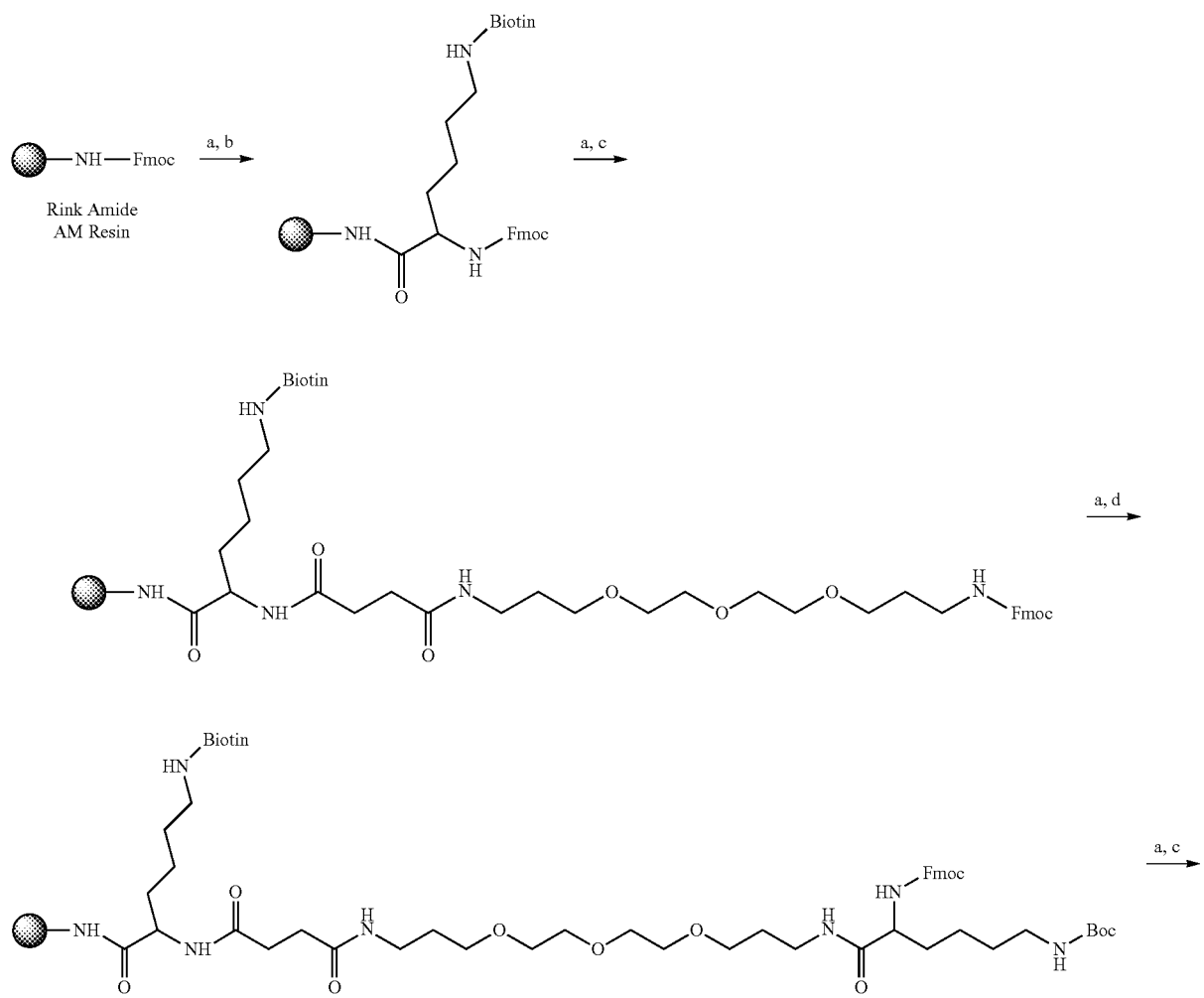

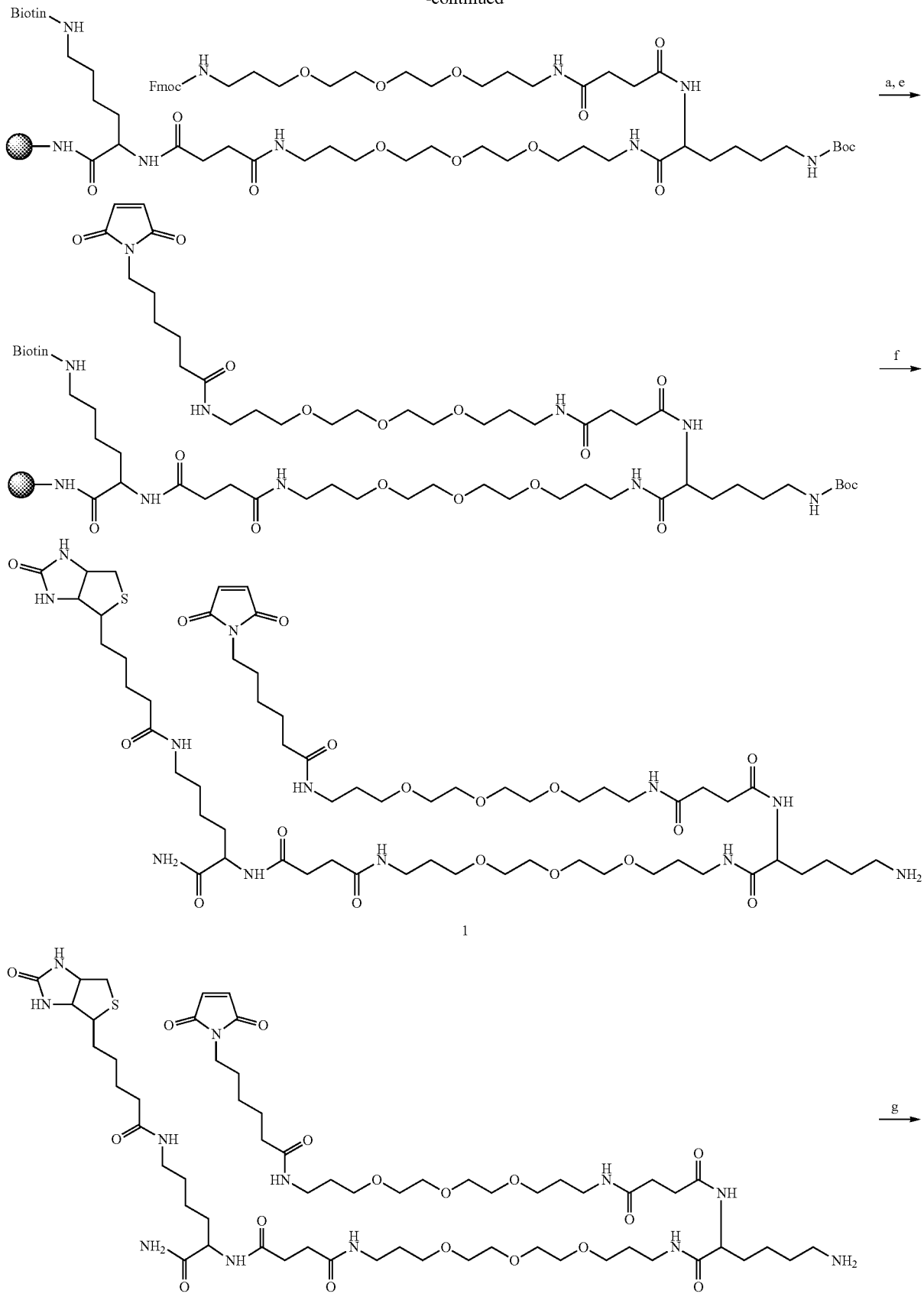

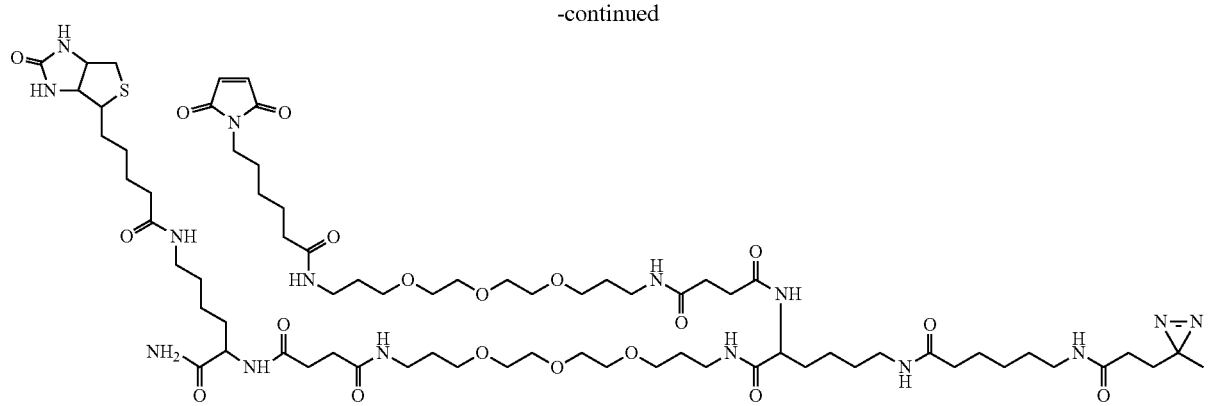

2

<sup>a</sup>Chemical probes and conditions: (a) 20% Piperidine/DMF; (b) Fmoc-Lys(Biotin)—OH, HCTU, NMM, DMF; (c) N—Fmoc-N″-succinyl-4,7,10-trioxa-1,13-tridecanediamine, HCTU, NMM, DMF; (d) Fmoc-Lys(Boc)—OH, HCTU, NMM, DMF; (e) 6-Maleimidohexanoic acid, HCTU, NMM, DMF; (f) TFA/TIS 95:5; (g) succinimidyl-6-(4, 4′-azipentanamido)hexanoate, Phosphate buffer, pH 8.

The synthesis was performed using the strategy, as previously described[5]. 80 mg (30 µmol) of Rink-Amide-AM-Resin was added to the fritted reaction vessel. Beads were conditioned with DMF for 15 minutes. The solution was removed by filtration, and 20% piperidine in DMF was added to the beads for fmoc deprotection. The mixture was end-to-end rotated for 30 minutes, and solution was removed followed by washing of beads with DMF. A reaction mixture of Fmoc-Lys-Biotin-OH (44.60 mg, 75 µmol), HCTU (31.03 mg, 75 µmol), and NMM (16.49 µl, 150 µmol) in DMF was added to the resin, and rotated for 4 hours at room temperature. The resin was washed with DMF, and fmoc deprotection steps were repeated. A solution of N-Fmoc-N″-succinyl-4,7,10-trioxa-1,13-tridecanediamine (40.70 mg, 75 µmol), HCTU (31.03 mg, 75 µmol), and NMM (16.49 µl, 150 µmol) in DMF was rotated with the resin for 4 hours. Excess reagents were removed, and the resin was washed with DMF. Similarly, Fmoc-Lys(Boc)-OH (35.14 mg, 75 µmol), N-Fmoc-N″-succinyl-4,7,10-trioxa-1, 13-tridecanediamine (40.70 mg, 75 µmol), and 6-Maleimidohexanoic acid (15.84 mg, 75 µmol) were coupled to the resin after fmoc deprotection steps. The resin was washed with DMF and dichloromethane, and the molecule was cleaved from the resin using 95:5 mixture of TFA:TIS (Triisopropylsilane) for 1.5 hours. The cleavage step also deprotects the boc group, making available a free amine in the product. The crude product was concentrated and HPLC (Agilent 1100) purified using a gradient of 5-85% B (A: 0.1% TFA/H$_2$O, B: 0.1% TFA/CH$_3$OH) over 30 minutes on Waters XBridge Prep BEH130 C18 column (5 µm, 10×250 mm) to yield 1 (25.68 mg, 19.8 µmol, 66%). MALDI-TOF and NMR were used to characterize the product.

$^1$H NMR (500 MHz, DMSO-d$_6$) δ 7.91 (d, J=8.1 Hz, 1H), 7.86-7.71 (m, 4H), 7.66 (q, J=5.9 Hz, 2H), 7.54 (bs, 3H), 7.26-7.18 (m, 1H), 6.91 (s, 2H), 6.89-6.83 (m, 1H), 6.42-6.20 (m, 2H), 4.28-4.16 (m, 1H), 4.10-3.94 (m, 3H), 3.49-3.18 (m, 24H), 3.04-2.85 (m, 11H), 2.70 (dd, J=15, 5.6 Hz, 1H), 2.71-2.61 (m, 2H), 2.49 (d, J=12.4 Hz, 1H), 2.33-2.16 (m, 8H), 1.94 (dt, J=13.4, 7.4 Hz, 4H), 1.68-1.47 (m, 11H), 1.46-1.32 (m, 11H), 1.31-0.99 (m, 11H).

$^{13}$C NMR (126 MHz, DMSO) δ 174.1, 172.0, 171.8, 171.6, 171.6, 171.5, 171.1, 162.8, 158.2, 158.0, 134.5, 117.4, 115.1, 112.7, 69.8, 69.6, 68.1, 68.1, 61.1, 59.3, 55.5, 52.4, 37.0, 36.0, 35.9, 35.8, 35.3, 35.2, 31.4, 31.2, 30.8, 30.7, 30.6, 29.4, 29.4, 29.3, 29.0, 28.3, 28.1, 27.8, 26.7, 25.8, 25.4, 24.9, 23.0, 22.5. A 1297.358 peak in MALDI was observed corresponding to the expected M+H$^+$.

The pure maleimide-biotin compound 1 (20 mg, 15.42 µmol) was dissolved in DMF and reacted with excess NHS-LC-Diazirine (succinimidyl-6-(4,4′-azipentanamido) hexanoate) in phosphate buffer pH 8, for 2 hours at room temperature. The product was purified by directly injecting into the HPLC and using similar conditions as described above. The chemo-proteomic probe 2 for labeling a virus or a bacterium was obtained as a white powder (14.06 mg, 9.25 µmol, 60%) and characterized by MALDI-TOF, $^1$H and $^{13}$C NMR.

$^1$H NMR (500 MHz, DMSO-d$_6$) δ 8.00-7.88 (m, 2H), 7.88-7.77 (m, 4H), 7.72 (p, J=5.8 Hz, 3H), 7.28 (p, J=2.7, 2.2 Hz, 1H), 6.99 (s, 2H), 6.94 (s, 1H), 6.45-6.31 (m, 2H), 4.32-4.26 (m, 1H), 4.15-4.03 (m, 3H), 3.54-3.41 (m, 17H), 3.40-3.24 (m, 7H), 3.14-2.92 (m, 16H), 2.81 (dd, J=12.4, 5.1 Hz, 1H), 2.56 (d, J=12.4 Hz, 1H), 2.40-2.23 (m, 8H), 2.06-1.96 (m, 6H), 1.96-1.88 (m, 2H), 1.72-1.52 (m, 13H), 1.52-1.40 (m, 10H), 1.40-1.08 (m, 18H), 0.96 (s, 3H).

$^{13}$C NMR (126 MHz, DMSO) δ 174.0, 171.8, 171.6, 171.5, 171.5, 171.4, 171.1, 170.5, 162.7, 134.5, 69.8, 69.5, 68.1, 61.1, 59.2, 55.4, 52.6, 52.4, 37.0, 35.8, 35.7, 35.4, 35.2, 35.2, 31.5, 31.4, 30.7, 29.9, 29.8, 29.4, 29.3, 29.2, 28.9, 28.9, 28.2, 28.0, 27.8, 26.1, 25.8, 25.3, 25.1, 24.8, 23.0, 19.3. MALDI showed a peak at 1492.232 m/z, corresponding to the M–N$_2$+H$^+$. This is due to the loss of N$_2$ from diazirine under MALDI conditions.

Virus Labeling/BSA Labeling

Purified Zika virus or 50 µg Bovine Serum Albumin (BSA) was diluted to 500 µl with PBS pH 7, and mixed with the labeling chemical probe in the final concentration of 1 mM. The labeling was carried out by gentle end-to-end rotation in 4° C. overnight. For the infection experiment, virus labeling was initiated a day before the cells reached <90% confluency for infection. The reaction was quenched by adding three times excess of cysteine.

Virus Infection and Crosslinking of Host-Proteins

Vero cells were first grown in T-150 flasks in DMEM supplemented with 10% FBS, then passaged to the 15 cm plates and grown to <90% confluence. Cells were washed with cold PBS twice, and cooled down to 4° C. The labeled virus was diluted in DMEM and added to the cells at an MOI of 5. Cells were gently rocked for 1 hour in 4° C., to allow for virus attachment. For the receptor crosslinking, the unbound virus was removed, cells were washed once with cold PBS, and directly exposed to the UV light for 15 minutes on ice. All the above operations were performed on ice and using cold PBS to minimize any virus entry. To understand the virus internalization mechanism, additionally virus was allowed to enter cells by incubation in 37° C. for 4 or 8 minutes, following pre-attachment for an hour at 4° C. Subsequent to UV photocrosslinking, cells were collected by scraping in PBS, and stored in −80° C. until further processing. As a control, cells treated with the labeling chemical probe and exposed to UV were included to account for random crosslinking.

Sample Preparation for LC-MS Analysis

Frozen cells were lysed in 1% SDS, 50 mM Tris HCl pH 7.5 supplemented with protease inhibitor on ice, using sonication (10 cycles for 10 seconds each, with an interval of 10 seconds). Cell lysates were cleared by centrifugation at 14000 rpm to pellet down cell debris, and supernatant were used for the biotin-Neutravidin affinity purification. Bicinchoninic acid (BCA) assay (Thermo Fisher Scientific) was performed for protein quantitation, and the lysates equivalent to 1 mg protein for each sample were reduced and alkylated by boiling at 95° C., in 10 mM TCEP (Tris(2-carboxyethyl)phosphine) and 40 mM CAA (chloroacetamide) respectively. The lysates were then diluted to 0.1% SDS and rotated with 50 μl preconditioned Neutravidin beads slurry in 4° C. overnight. The beads were washed three times with 0.1% SDS in Tris-HCl pH 8, and then transferred to the low protein binding eppendorf tubes, where they were further washed three times with 25 mM ammonium bicarbonate (ABC) buffer pH 8. 200 μl ABC buffer was added to the beads, and proteins were digested on-bead at 37° C. using 2 μg Lys-C for 3 hours and 200 ng trypsin for 12 hours. The supernatant containing peptides was collected and beads were washed twice with 50 μl ABC buffer, further pooled with the supernatant. Peptides were acidified and desalted using in-house StageTips with SDB-XC (3M). The peptides were dried in SpeedVac before subjecting to LC-MS/MS analysis.

LC-MS/MS Analysis

The peptides were dissolved in 0.1% formic acid and injected into Easy-nLC 1000 (Thermo Fisher Scientific). The peptides were separated on a 45 cm in-house column (360 μm OD×75 μm ID), packed with C18 resin (2.2 μm, 100 Å, Bischoff Chromatography, Leonberg, Germany) and heated to 60° C. with a column heater (Analytical Sales and Services, Flanders, N.J.). The mobile phase was comprised of 0.1% formic acid in ultra-pure water (solvent A) and 0.1% formic acid in 80% Acetonitrile (solvent B), and the gradient used for separation was 10-30% B over a linear 60 minutes at a flow rate of 250 nl/min. The EASY-nLC 1000 was connected online to the LTQ-Orbitrap Velos Pro mass spectrometer (Thermo Fisher Scientific) by a nanospray source. Data acquisition was performed in the data-dependent mode, in which a full scan (range from m/z 350-1800 with a resolution of 30,000 at m/z 400) was followed by MS/MS scans of top 10 intense ions (normalized collision energy 30%, automatic gain control 3e4, maximum injection time 100 ms) with a dynamic exclusion for 60 s and dynamic list of 500.

LC-MS Data Processing

Raw files were processed with MaxQuant v1.5.5.1[6], and the Label-free Quantitation (LFQ)[7] was performed. The raw data was searched against UniProtKB green monkey (*Chlorocebus sabaeus*) FASTA database with *Andromeda* search engine[8], using standard parameters. The first peptide precursor mass tolerance was set at 20 ppm, and MS/MS tolerance at 0.6 Da. Carbamidomethylation was set as a fixed modification for cysteines, while oxidation of methionine and acetylation at N-terminus were selected as variable modifications. Enzyme specificity was set to trypsin with maximum two missed cleavages. The search was performed with 1% false discovery rate (FDR) at both peptide and protein levels. The identifications were transferred from the sequenced peaks to the unidentified peaks of the same m/z within a time window of 0.7 minutes (match between runs) across samples.

Statistical Analysis

Data was analyzed by Perseus 1.6.1.1[9]. Initially, the LFQ intensities were extracted from the MaxQuant output file. All potential contaminants were removed, along with proteins only identified by site. Proteins with valid values in minimum two out of three replicates in at least one group were only considered, and values were imputed for all missing values based on normal distribution. The t-test was performed to identify significant outliers (permutation-based FDR 5%). Proteins in the significant region with at least 2.5-fold change for UV at different time points vs control were considered as crosslinked proteins, which were further analyzed by Ingenuity Pathway Analysis, DAVID (Database for Annotation, Visualization, and Integrated Discovery)[10, 11], and STRING[12, 13]. Proteins were matched to their homologs from UniProt human database for the analysis. Principal Component Analysis (PCA) was performed with a Benjamin-Hochberg FDR cut-off of 0.05.

Antibody Inhibition of Virus Infection

Antibody inhibition assay was performed according to the protocol described before[14]. Vero cells in six-well plate were preincubated with 30 μg/ml of anti-NCAM or control IgG in DMEM for 45 min at room temperature. Cells were then infected with purified Zika at an MOI of 0.1 in the presence of antibody. Cellular RNA was purified after 24 h, and RT-qPCR was performed to measure viral RNA.

RNA Extraction and RT-qPCR

RNA was extracted using RNeasy mini kit (Qiagen, Valencia, Calif.) as per manufacturer's protocol, and RT-qPCR was performed using SuperScript III Platinum SYBR Green One-Step qRT-PCR kit (Invitrogen, Grand Island, N.Y.). The purified total RNA in water, were normalized and used to generate cDNA. Gene expression was measured using Applied Biosystems 7300 real-time PCR system. The conditions used were 4 minutes at 50° C., 5 minutes at 95° C., and 40 cycles of 15 seconds at 95° C. and 1 minute at 60° C. The number of viral RNA copies was determined using a standard curve.

Overexpression of NCAM in HEK293T Cells

HEK293T cells at the confluency of 60% were transfected with an expression plasmid with NCAM1 (GenScript, OHu00262D), using lipofectamine 2000 reagent. 48 hours post transfection, cells were challenged with Zika virus at MOI of 0.1. The virus was incubated with the cells at 4° C. for 1 hour, and increase in viral attachment was measured using RT-qPCR[15].

Immunofluorescence

Vero cells or HEK293T cells (for transfection with NCAM1) were seeded on cover slips in 24-well plate. Cells were washed with PBS and fixed with 3.7% paraformaldehyde for 10 minutes at room temperature. Cells were again washed with PBS three times and blocked with 2% BSA in PBS for 1 hour. Anti-NCAM antibody in blocking solution was incubated with the cells for 1 hour at room temperature. Cells were washed three times and incubated with anti-mouse FITC or anti-mouse Alexa Fluor 488 for 1 hour at room temperature. DAPI staining was performed for 10 minutes, followed by final three PBS washes. Cover slips were mounted on glass slide and images were captured using Olympus IX81 fluorescence microscope with a 60× oil immersion objective.

Western Blot

Following overexpression of NCAM1 in HEK293T, cells were lysed at 48 hours post transfection. The samples were boiled at 95° C. in gel loading buffer and 1,4-Dithiothreitol (DTT) for 5 minutes. The cell lysates were separated on the precast NuPAGE 4-12% Bis-Tris polyacrylamide gels (Invitrogen) for 90 minutes at constant voltage of 150V. A MOPS solution (50 mM MOPS, 50 mM Tris-base, 1 mM EDTA, 0.1% SDS) was used as a running buffer. The proteins were transferred onto polyvinylidene fluoride membranes in Bicine-Bis-Tris transfer buffer containing 12% methanol, for 75 minutes at a constant current of 275 mA. The membrane was blocked with 2% BSA in TBST, and probed with anti-human NCAM (Cell Signaling) for 1 hour at room temperature. Following washings, anti-mouse IgG HRP-conjugated secondary antibody (Cell Signaling) was utilized for visualization.

Example Bacterium Salmonella Labeling

As illustrated in FIG. 1, to study the temporal interaction profile between salmonella and macrophage, labeled salmonella were added to macrophage cells at the MOI of 50 and incubated for set intervals ranging from 15 min to 6 hours to allow the infection. After washed away the attached salmonella, macrophage samples with different infection time were irradiated with 365 nm UV light for 10 min to covalently crosslink the host proteins directly involved in the SCV formation with salmonella. We reasoned that the probe with a photoreactive diazirine group, which is known to be specific in crosslinking molecules with interaction, in combination with its spacer length of 12.5 Å, only react with proteins that direct contact with the salmonella, thereby avoids crosslinking of other non-specific interacting proteins. The irradiated cells were then harvest and lysated with lysis buffer, and NeutrAvidin beads were used to isolate the putative targets, and the beads was subsequently washed with vigorous washing conditions (1% SDS, 8 M urea, 10×PBS and 25 mM ABC sequentially, three times wash for each buffer) to remove non-specific captured proteins.

Except for extensive washing with different buffers to remove non-specific adsorptions, another important consideration in pathogen-host interaction studies is that protein abundances within a cell would change significantly as trigger significant changes, and the background could be quite different than the one observed in an uninfected cell. Therefore, control isolation is also performed in the same biological context tested. The proteins enriched by NeutrAvidin beads either from samples and controls are digested on-beads sequentially with Lys C and trypsin, and the obtained peptides were characterized and quantified by label-free LC-MS/MS. To increase the confidence level of the cross-linked proteins being true pathogen-interacting proteins, proteins only identified in UV-treated samples were considered as proteins cross-linked with the pathogen.

After subtracting the control hits (infected cells using labeled salmonella but without UV irradiation), in total, we identified 442 cross-linked proteins in two biological replicates over the three time points during salmonella internalization into macrophage cells. Proteins identified from samples and controls in each time point is shown in FIG. 3A. Among them, 292 (66%), 259 (52%), and 136 (31%) proteins were exclusively captured at 15 min, 1 hour, and 6 hours, respectively (FIG. 3B), suggesting that this approach was able to reveal the temporal distribution of the interacting host proteins cross-linked with the pathogen among the three time points. We noticed that both high technical and biological reproducibility are achieved, two independent biological replicates and three technique replicates correlated well for each time point (FIG. 3C). The correlation analysis also revealed that the 15 min and 1 hour results are more closely related, as both of these two time points are within the relatively early endocytosis process. The three time points clearly separated in the principal component analysis (PCA) plot, with the 15 min and 1 hour sharing more similarity.

We then analyzed the proteomics data to see whether this approach was capable of correlating spatial information with the captured cross-linked proteins, and whether these cross-linked proteins can fall into distinct biological processes or pathways. Gene ontology cellular component (GOCC) analysis shows the proteins with the highest levels of enrichment originated from extracellular regions (including vesicles, organelles, and exosomes) or from membrane-bound vesicles or organelles, especially at 0.5 and 1 h (FIG. 3D).

The GOCC results agree with the infection process, as adhesion to the host cell surface is important for many bacteria to initiate infection, and during the entry the salmonella may further fuse with the cellular membrane to form SCV. We identified more nucleus proteins in 6 hour samples than the other two time points. We assumed that the reason is the SCV membrane may damage in the late endocytosis process and the pathogen may escape into the host cell cytosol and become associated with nucleus proteins. The function analysis indicates many of proteins identified in these three time points are related to biological processes implicated in endocytosis, salmonella infection, regulation of actin cytoskeleton as well as focal adhesion (FIG. 3E), and pathway analysis shows that these proteins are involved in a number of biological processes linked to Vacuolar transport, Cell-cell signaling, and Vesicle mediated transport (FIG. 3F).

Figure 4A:
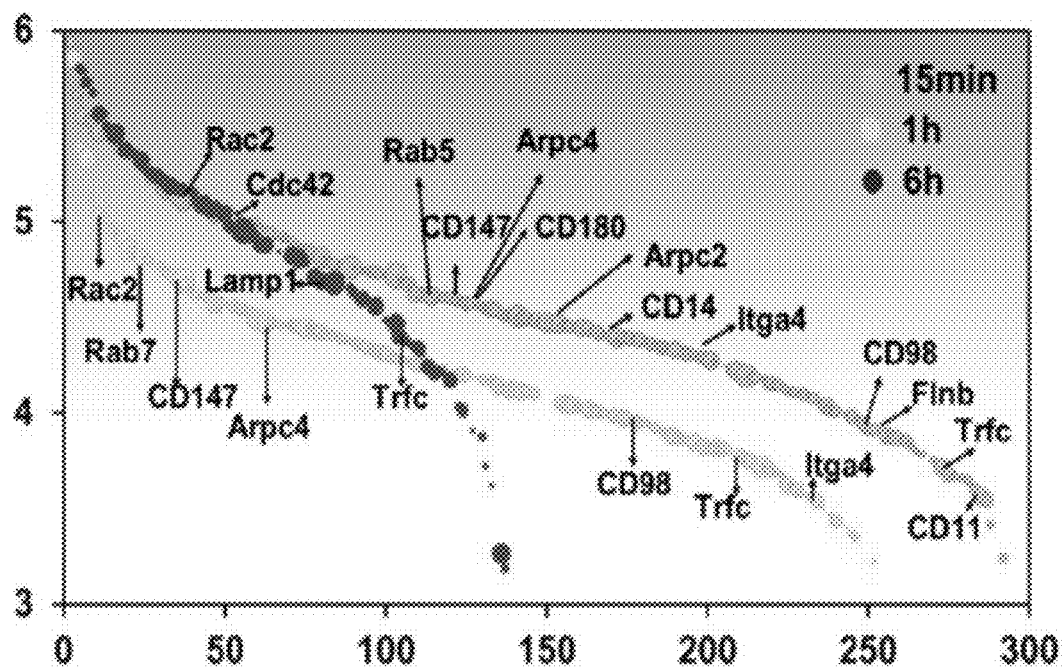
FIG. 4A shows proteins identified in each time point of 15 min, 1 hour and 6 hour.
Figure 4B:
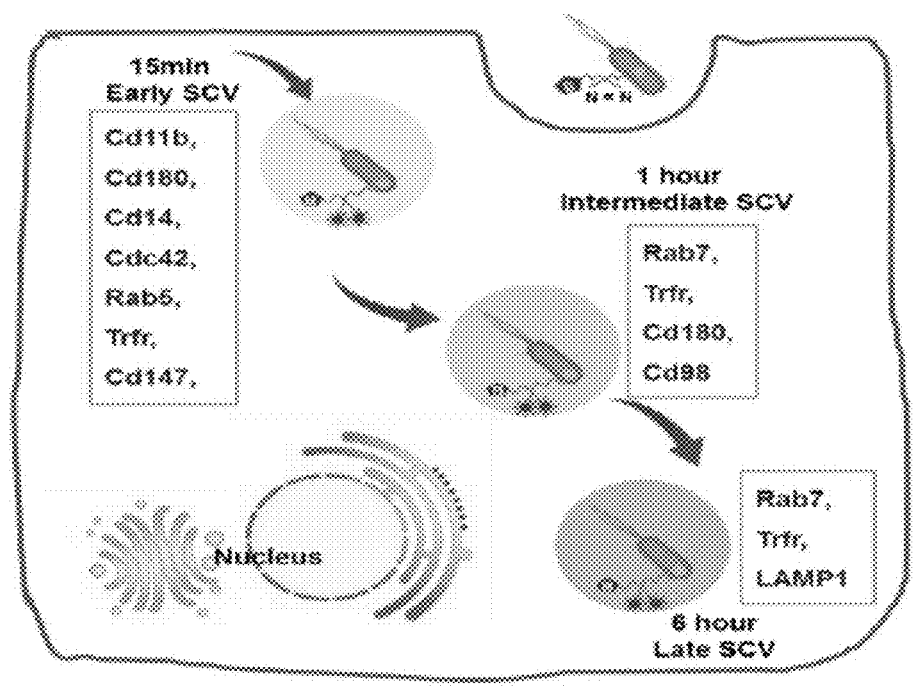
FIG. 4B shows illustration of the entry of salmonella into host cells by revealing the specific interacting proteins at different SCV formation process.
Figure 4C:
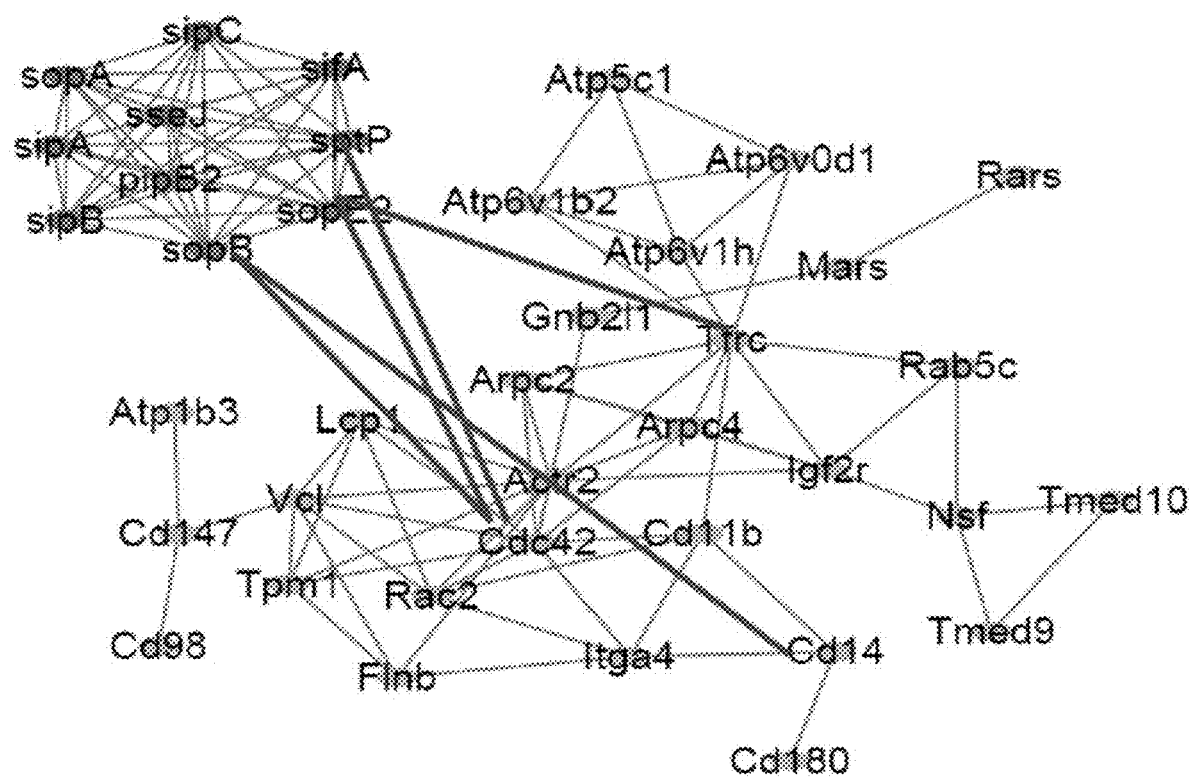
FIG. 4C shows interaction between the identified proteins from the host cell and interaction between the pathogen and the host.
Figure 4D:
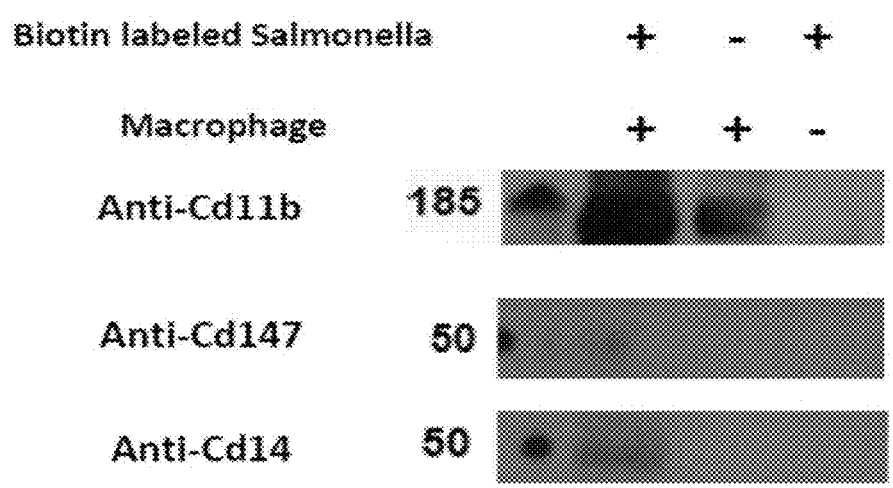
FIG. 4D shows Verification of some of the interacted proteins to confirm the interaction. Among them, the interaction between salmonella and Cd 14 is known, as Cd14 acts as a co-receptor (along with the Toll-like receptor TLR 4 and MD-2) for the recognition of lipopolysaccharide from salmonella surface. Interaction between pathogen and Cd 147, Cd 11b are reported in other pathogen-host interaction system but are not reported in the salmonella-macrophage system, and in this study they are discovered and verified for the first time between salmonella and macrophages, further indicating this approach is useful in discovering new potential interactions.

As this approach provides a temporal profile of the interaction between salmonella and macrophages, which is a particular advantage of this approach, we then further looked into proteins identified in each time point (FIG. 4A). At the very early time point of 15 min infection, salmonella was internalized by phagocytic cells through zipper mechanism, proteins involved in this process are expected to cross-link with the salmonella. For example, Arpc 2, Arpc 4 and F-actin capping protein are identified, which agrees with the fact that actin polymerization is stimulated in the initial steps of the internalization. Other known interactions are also identified, for example Cdc 42, which is known to be bonded and activated by salmonella effector Sop E; and CD147, which is reported as the receptor for salmonella.

Early SCV markers, Rab 5 and Trfc are also presented in the 15 min sample. In addition to identification of proteins that are previous reported to interact with salmonella, we discovered several new surface proteins from macrophage that potentially interact with salmonella during early infection including, Cd98, Cd180, Cd11b and Cd14, some of them are reported as receptor or binding with lipopolysaccharide in other bacteria. In the meanwhile, proteins from salmonella that are known to interact with the host cells and help the uptake of salmonella including Sif A, Sip B, Sip C, Sop A, Sop D, Sop E, Sop E2 are identified, further indicating the capability of this method to identify interaction between pathogen and host. In 1 hour sample, several proteins identified are overlapped with the 15 min samples, including Rab 5, Rab7, Trfc, Cd 14, Cd 147, Cd180 and et al., while Cdc42 disappeared. In the 6 h sample, early and intermediate SCV matures into late SCV by loss of early endosomal proteins and simultaneous acquisition of selective late endosomal and lysosomal proteins including LAMP1, while proteins participate in the early SCV formation all disappeared, including abovementioned CD family proteins and early SCV markers Rab5. Together, these results indicate that this approach can be used to trace the entry of salmonella into host cells by revealing the specific interacting proteins at different SCV formation process (FIG. 4B). Interaction between the identified proteins from the host cell and interaction between the pathogen and the host are shown in (FIG. 4C). The identification of host cell surface proteins that bind and facilitate pathogen entry into cells, as well as of other plasma membrane-resident proteins or host proteins identified in this study may contribute to the understanding of SCV formation and vital replication in the SCV. In light of these results, we further verified some of the interacted proteins to confirm the interaction (FIG. 4D). Among them, the interaction between salmonella and Cd 14 is known, as Cd14 acts as a co-receptor (along with the Toll-like receptor TLR 4 and MD-2) for the recognition of lipopolysaccharide from salmonella surface. Interaction between pathogen and Cd 147, Cd 11b are reported in other pathogen-host interaction system but are not reported in the salmonella-macrophage system, and in this study they are discovered and verified for the first time between salmonella and macrophages, further indicating this approach is useful in discovering new potential interactions.

GO Analysis

Functional annotation of gene ontology and KEGG pathway for each protein were retrieved from UNIPROT database (http://www.uniprot.org). KEGG pathway and GO enrichment analysis of the differentially expressed proteins were conducted according to the information from the KEGG Pathway and GO databases, respectively, using the following formula:

$$p = 1 - \sum_{i=0}^{m-1} \frac{\binom{M}{i}\binom{N-M}{n-i}}{\binom{N}{n}}$$

N is the number of all identified proteins that can be connected with GO or KEGG Pathway analysis information.

n is the number of differential proteins in N.

M is the number of proteins that can be connected with a certain GO term or pathway.

m is the number of differential proteins with certain GO term or KEGG pathway.

The ratio value was defined as the protein number of identified for each functional category normalized by protein number of genome background. The GO term or pathway is considered as a significant enrichment of differential proteins when p value is blow 0.05. Among them, several important biological process and pathway were particularly highlighted with red.

Those skilled in the art will recognize that numerous modifications can be made to the specific implementations described above. The implementations should not be limited to the particular limitations described. Other implementations may be possible.

While the inventions have been illustrated and described in detail in the drawings and foregoing description, the same is to be considered as illustrative and not restrictive in character, it being understood that only certain embodiments have been shown and described and that all changes and modifications that come within the spirit of the invention are desired to be protected.

It is intended that that the scope of the present methods and compositions be defined by the following claims. However, it must be understood that this disclosure may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims.

REFERENCES CITED

[1] W. S. Garrett, Science 2015, 348, 80-86.
[2] P. M. J. Beltran, J. D. Federspiel, X. Sheng, I. M. Cristea, Mol. Syst. Biol. 2017, 13, 922.
[3] M. P. Weekes, P. Tomasec, E. L. Huttlin, C. A. Fielding, D. Nusinow, R. J. Stanton, E. C. Wang, R. Aicheler, I. Murrell, G. W. Wilkinson, P. J. Lehner, S. P. Gygi, Cell 2014, 157, 1460-1472.
[4] P. Scaturro, A. Stukalov, D. A. Haas, M. Cortese, K. Draganova, A. Plaszczyca, R. Bartenschlager, M. Götz, A. Pichlmair, Nature 2018, 561, 253-257.
[5] Y. F. Yang, M. Hu, K. W. Yu, X. M. Zeng, X. Y. Liu Mass spectrometry-based proteomic approaches to study pathogenic bacteria-host interactions. Protein Cell, 2015 6, 265-274.
[6] A. P. Frei, O. Y. Jeon, S. Kilcher, H. Moest, L. M. Henning, C. Jost, A. Plückthun, J. Mercer, R. Aebersold, E. M. Carreira, B. Wollscheid, Nat. Biotech. 2012, 30, 997-1001.
[7] N. Sobotzki, M. A. Schafroth, A. Rudnicka, A. Koetemann, F. Marty, S. Goetze, Y. Yamauchi, E. M. Carreira, B. Wollscheid, Nat. Commun. 2018, 9, 1519.
[8] L. Bar-Peled, E. K. Kemper, R. M. Suciu, E. V. Vinogradova, K. M. Backus, B. D. Horning, T. A. Paul, T. A. Ichu, R. U. Svensson, J. Olucha, M. W. Chang, B. P. Kok, Z. Zhu, N. T. Ihle, M. M. Dix, P. Jiang, M. M. Hayward, E. Saez, R. J. Shaw, B. F. Cravatt, Cell 2017, 171, 696-709.

[9] D. He, X. Xie, F. Yang, H. Zhang, H. M. Su, Y. Ge, H. P. Song, P. R. Chen, *Angew. Chem. Int. Ed.,* 2017, 56, 14521-14525; *Angew. Chem.* 2017, 129, 14713-14717.

[10] M. Broncel, R. A. Serwa, P. Ciepla, E. Krause, M. J. Dallman, A. I. Magee, E. W. Tate, *Angew. Chem. Int. Ed* 2015, 54, 5948-5951; *Angew. Chem.* 2015, 127, 6046-6049.

[11] L. N. Wang, L. Yang, L. Pan, N. R. Kadasala, L. Xue, R. J. Schuster, L. L. Parker, A. Wei, W. A. Tao, *J. Am. Chem. Soc.* 2015, 137, 12772-12775.

[12] A. Haraga, M. B. Ohlson, S. I. Miller, *Nat. Rev. Micro.,* 2008, 6, 53-66.

[13] O. Steele-Mortimer, *Curr. Opin. Microbiol.* 2008, 11, 38-45.

[14] T. H. Greg Bioconjugate Techniques, 2$^{nd}$ Edition, Academic Press, New York, 2008, pp. 171 and 183.

[15] Y. Zeng, T. N. C Ramya, A. Dirksen, P. E. Dawson, J. C. Paulson, *Nat. Meth.,* 2009, 6, 207-209.

[16] H. P. Xiao, S. Suttapitugsakul, F. X. Sun, R. H. Wu, *Acc. Chem. Res.,* 2018, 51, 1796-1806.

[17] Z. Q. Li, P. L. Hao, L. Li, C. Y. J. Tan, X. M. Cheng, G. Y. J. Chen, S. K. Sze, H. M. Shen, S. Q. Yao, *Angew. Chem. Int. Ed.,* 2013, 52, 8551-8556; *Angew. Chem.* 2013, 125, 8713-8718.

[18] S. Schleker, J. C. Sun, B. Raghavan, M. Srnec, N. Muller, M. Koepfinger, L. Murthy, Z. M. Zhao, J. Klein-Seetharaman, *Proteomics Clin. Appl.* 2012, 6, 117-133.

[19] L. D. Rogers, A. R. Kristensen, E. C. Boyle, D. P. Robinson, R. T. Ly, B. B. Finlay, L. J. Foster, *J. Proteomics* 2008, 71, 97-108.

[20] G. J. Rapsinski, T. N. Newman, G. O. Oppong, J. P. van Putten, Ç. Tükel, *J. Biol. Chem.* 2013, 288, 14178-14188.

[21] L. A. Knodler, O. Steele-Mortimer, *Traffic* 2003, 4, 587-599.

[22] I. Zanoni, R. Ostuni, L. R. Marek, S. Barresi, R. Barbalat, G. M. Barton, F. Granucci, J. C. Kagan, *Cell* 2011, 147, 868-880.

[23] N. Schroeder, C. S. Chung, C. H. Chen, Liao, C L, W. Chang, *J. Virol.* 2012, 86, 4868-4882.

[24] S. C. Bernard, N. Simpson, O. Join-Lambert, C. Federici, M. P. Laran-Chich, N. Maissa, H. Bouzinba-Segard, P. C. Morand, F. Chretien, S. Taouji, E. Chevet, S. Janel, F. Lafont, M. Coureuil, A. Segura, F. Niedergang, S. Marullo, P. O. Couraud, X. Nassif, S. Bourdoulous, *Nat. Med.* 2014, 20, 725-731.

[25] J. C. Kagan, *Trends Immunol.* 2017, 38, 696-704.

---

The invention claimed is:

1. A chemo-proteomic probe comprising:
   a) a functional group for conjugating to a surface protein of a live microbe under a physiological condition;
   b) a photo-reactive group for covalent cross-linking to an interacting protein of a host cell; and
   c) a tag for isolating the cross-linked complex of the surface protein of said live microbe and the interacting protein of a host cell for qualitative and quantitative analyses.

2. The chemo-proteomic probe according to claim 1 further comprising a visualization tag for viewing the interactions between the microbe and a host cell in real time.

3. The chemo-proteomic probe according to claim 1, wherein the live microbe is a pathogen to human or an animal comprising a bacterium or a virus.

4. The chemo-proteomic probe according to claim 1, wherein the probe is suitable for studying the temporal interactions between a pathogen and its host cell.

5. The chemo-proteomic probe according to claim 1, wherein the photo-reactive group is a photocrosslinker or a photocleavable caging group.

6. The chemo-proteomic probe according to claim 5, wherein the photocrosslinker is a diazirine or an aryl azide.

7. The chemo-proteomic probe according to claim 1, wherein the probe has a formula:

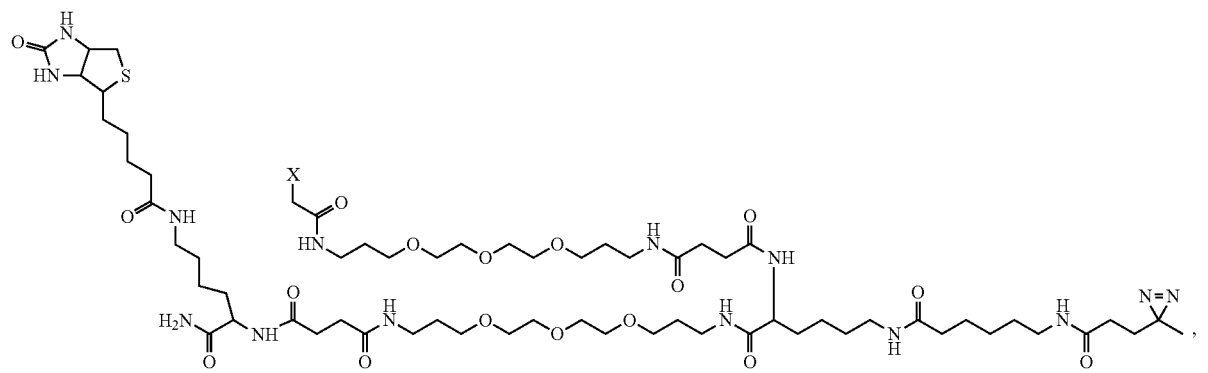

(I)

or an acceptable salt thereof, wherein X is said functional group selected from the group consisting of N-hydroxysuccinimide (NHS), maleimide (MAL), or aminooxy (ONH$_2$).

8. The chemo-proteomic probe according to claim 7, wherein said X is

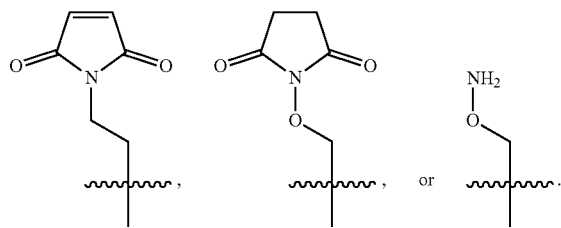

9. The chemo-proteomic probe according to claim 1, wherein the tag for isolating the cross-linked complex of the surface protein of said live microbe and the interacting protein of a host cell for qualitative and quantitative analyses is selected from the group consisting of biotin, thiobiotin, azide-alkyne, aldehyde-hydrazine, aldehyde-hydroxylamine, thiol-iodoacetyl, and a thiobiotin-based affinity tag.

10. The chemo-proteomic probe according to claim 1, wherein the live microbe is a bacterium or a virus and the docking surface reactive group of a host cell for covalent conjugation is a reactive group of glycan.

11. The chemo-proteomic probe according to claim 1, wherein the live microbe is a bacterium or a virus and the docking surface reactive group of a host cell for covalent conjugation is a functional group selected from the group consisting of amino (NH$_2$) and thiol (SH).

12. A method of identifying proteins interactions between a host and a pathogen microbe in real time, comprising the steps of:
  a) providing a chemo-proteomic probe comprising: a functional group for conjugating to a surface protein of a live microbe under a physiological condition; a photo-reactive group for covalent cross-linking to an interacting protein of a host cell; and a tag for isolating the cross-linked complex of the surface protein of said live microbe and the interacting protein of a host cell for qualitative and quantitative analyses;
  b) allowing the microbe to infect the host;
  c) crosslinking at fixed time points so that the interacting proteins of the host cells have sufficiently interacted with the surface proteins of the pathogen microbe;
  d) isolating the cross-linked complex of the surface proteins of said pathogen microbe and the interacting cell proteins of a host utilizing the tag; and
  e) performing qualitative and quantitative analyses of the isolated cross-linked protein complex.

13. The method according to claim 12, wherein the pathogen microbe is a virus or a bacterium.

14. The method according to claim 12, wherein the qualitative and quantitative analysis is to sequence the isolated cross-linked protein complex by mass spectroscopy.

15. The method according to claim 12, wherein the chemo-proteomic probe further comprising a visualization tag to view the microbe-host cell interaction in real time.

16. The method according to claim 15, wherein the photo-reactive group is a diazirine or an aryl azide.

17. The method according to claim 15, wherein the chemo-proteomic probe has a formula:

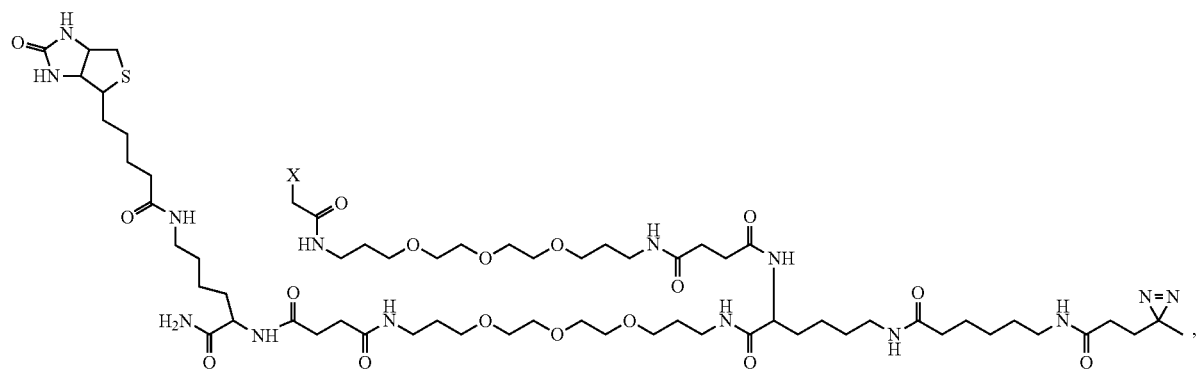

(I)

or an acceptable salt thereof, wherein X is said functional group selected from the group consisting of N-hydroxysuccinimide (NHS), maleimide (MAL), or aminooxy (ONH$_2$).

18. The method according to claim 17, wherein said X is

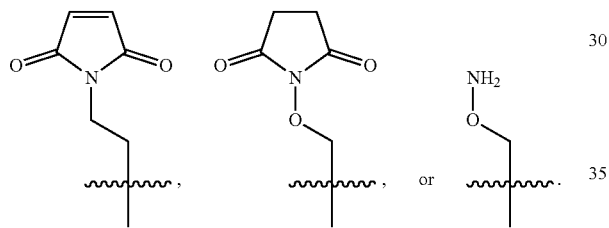

19. The method according to claim 12, wherein the tag for isolating the cross-linked complex of the surface protein of said live microbe and the interacting cell protein of a host for qualitative and quantitative analyses is selected from the group consisting of biotin, thiobiotin, azide-alkyne, aldehyde-hydrazine/hydroxylamine, thiol-iodoacetyl, and a thiobiotin-based affinity tag.

20. A kit for identifying interactions between a host cell and a pathogen microbe in real time, comprising:
  a) a chemo-proteomic probe comprising: a functional group for conjugating to a surface protein of a live microbe under a physiological condition; a photo-reactive group for covalent cross-linking to an interacting cell protein of a host; and a tag for isolating the cross-linked complex of the surface protein of said live microbe and the interacting cell protein of a host for qualitative and quantitative proteomics analyses; and
  b) reagents for enabling said conjugation and crosslinking.

* * * * *

SEQUENCE LISTING

<160> NUMBER OF SEQ ID NOS: 1

<210> SEQ ID NO 1
<211> LENGTH: 500
<212> TYPE: PRT
<213> ORGANISM: Artificial sequence
<220> FEATURE:
<223> OTHER INFORMATION: Zika peptide E sequence

<400> SEQUENCE: 1

```
Ile Arg Cys Ile Gly Val Ser Asn Arg Asp Phe Val Glu Gly Met Ser
1               5                   10                  15

Gly Gly Thr Trp Val Asp Val Val Leu Glu His Gly Gly Cys Val Thr
            20                  25                  30

Val Met Ala Gln Asp Lys Pro Thr Val Asp Ile Glu Leu Val Thr Thr
        35                  40                  45

Thr Val Ser Asn Met Ala Glu Val Arg Ser Tyr Cys Tyr Glu Ala Ser
    50                  55                  60

Ile Ser Asp Met Ala Ser Asp Ser Arg Cys Pro Thr Gln Gly Glu Ala
65                  70                  75                  80

Tyr Leu Asp Lys Gln Ser Asp Thr Gln Tyr Val Cys Lys Arg Thr Leu
                85                  90                  95

Val Asp Arg Gly Trp Gly Asn Gly Cys Gly Leu Phe Gly Lys Gly Ser
            100                 105                 110

Leu Val Thr Cys Ala Lys Phe Thr Cys Ser Lys Lys Met Thr Gly Lys
        115                 120                 125

Ser Ile Gln Pro Glu Asn Leu Glu Tyr Arg Ile Met Leu Ser Val His
    130                 135                 140

Gly Ser Gln His Ser Gly Met Ile Gly Tyr Glu Thr Asp Glu Asp Arg
145                 150                 155                 160

Ala Lys Val Glu Val Thr Pro Asn Ser Pro Arg Ala Glu Ala Thr Leu
                165                 170                 175

Gly Gly Phe Gly Ser Leu Gly Leu Asp Cys Glu Pro Arg Thr Gly Leu
            180                 185                 190
```

-continued

```
Asp Phe Ser Asp Leu Tyr Tyr Leu Thr Met Asn Asn Lys His Trp Leu
        195                 200                 205

Val His Lys Glu Trp Phe His Asp Ile Pro Leu Pro Trp His Ala Gly
    210                 215                 220

Ala Asp Thr Gly Thr Pro His Trp Asn Asn Lys Glu Ala Leu Val Glu
225                 230                 235                 240

Phe Lys Asp Ala His Ala Lys Arg Gln Thr Val Val Val Leu Gly Ser
                245                 250                 255

Gln Glu Gly Ala Val His Thr Ala Leu Ala Gly Ala Leu Glu Ala Glu
                260                 265                 270

Met Asp Gly Ala Lys Gly Arg Leu Phe Ser Gly His Leu Lys Cys Arg
            275                 280                 285

Leu Lys Met Asp Lys Leu Arg Leu Lys Gly Val Ser Tyr Ser Leu Cys
        290                 295                 300

Thr Ala Ala Phe Thr Phe Thr Lys Val Pro Ala Glu Thr Leu His Gly
305                 310                 315                 320

Thr Val Thr Val Glu Val Gln Tyr Ala Gly Thr Asp Gly Pro Cys Lys
                325                 330                 335

Ile Pro Val Gln Met Ala Val Asp Met Gln Thr Leu Thr Pro Val Gly
                340                 345                 350

Arg Leu Ile Thr Ala Asn Pro Val Ile Thr Glu Ser Thr Glu Asn Ser
        355                 360                 365

Lys Met Met Leu Glu Leu Asp Pro Pro Phe Gly Asp Ser Tyr Ile Val
    370                 375                 380

Ile Gly Val Gly Asp Lys Lys Ile Thr His His Trp His Arg Ser Gly
385                 390                 395                 400

Ser Thr Ile Gly Lys Ala Phe Glu Ala Thr Val Arg Gly Ala Lys Arg
                405                 410                 415

Met Ala Val Leu Gly Asp Thr Ala Trp Asp Phe Gly Ser Val Gly Gly
            420                 425                 430

Val Phe Asn Ser Leu Gly Lys Gly Ile His Gln Ile Phe Gly Ala Ala
        435                 440                 445

Phe Lys Ser Leu Phe Gly Gly Met Ser Trp Phe Ser Gln Ile Leu Ile
    450                 455                 460

Gly Thr Leu Leu Val Trp Leu Gly Leu Asn Thr Lys Asn Gly Ser Ile
465                 470                 475                 480

Ser Leu Thr Cys Leu Ala Leu Gly Gly Val Met Ile Phe Leu Ser Thr
                485                 490                 495

Ala Val Ser Ala
            500
```